(12) United States Patent
Sutton et al.

(10) Patent No.: US 8,063,063 B2
(45) Date of Patent: Nov. 22, 2011

(54) IMMUNOPOTENTIATING COMPOUNDS

(75) Inventors: James Sutton, Pleasanton, CA (US);
Nicholas Valiante, Fremont, CA (US)

(73) Assignee: Novartis AG, Basel (CH)

( * ) Notice: Subject to any disclaimer, the term of this patent is extended or adjusted under 35 U.S.C. 154(b) by 328 days.

(21) Appl. No.: 12/294,237

(22) PCT Filed: Mar. 23, 2007

(86) PCT No.: PCT/US2007/064857
§ 371 (c)(1),
(2), (4) Date: Sep. 23, 2008

(87) PCT Pub. No.: WO2007/109812
PCT Pub. Date: Sep. 27, 2007

(65) Prior Publication Data
US 2009/0232844 A1    Sep. 17, 2009

Related U.S. Application Data

(60) Provisional application No. 60/785,539, filed on Mar. 23, 2006.

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)

(52) U.S. Cl. .................. 514/303; 546/118
(58) Field of Classification Search .................. 546/118; 514/303
See application file for complete search history.

(56) References Cited

U.S. PATENT DOCUMENTS

| | | |
|---|---|---|
| 4,689,338 A | 8/1987 | Gerster |
| 4,698,348 A | 10/1987 | Gerster |
| 4,806,352 A | 2/1989 | Cantrell |
| 4,929,624 A | 5/1990 | Gerster et al. |
| 5,011,828 A | 4/1991 | Goodman et al. |
| 5,026,543 A | 6/1991 | Rijke |
| 5,026,546 A | 6/1991 | Hilgers et al. |
| 5,057,540 A | 10/1991 | Kensil et al. |
| 5,238,944 A | 8/1993 | Wick et al. |
| 5,266,575 A | 11/1993 | Gerster et al. |
| 5,268,376 A | 12/1993 | Gester |
| 5,306,492 A | 4/1994 | Porro |
| 5,346,905 A | 9/1994 | Gerster |
| 5,352,784 A | 10/1994 | Nikolaides et al. |
| 5,360,897 A | 11/1994 | Anderson et al. |
| 5,378,814 A | 1/1995 | Houghton et al. |
| 5,385,937 A | 1/1995 | Stemler et al. |
| 5,389,640 A | 2/1995 | Gerster et al. |
| 5,395,937 A | 3/1995 | Nikolaides et al. |
| 5,482,936 A | 1/1996 | Lindstrom |
| 5,494,916 A | 2/1996 | Lindstrom et al. |
| 5,525,612 A | 6/1996 | Gerster |
| 5,658,731 A | 8/1997 | Sproat et al. |
| 5,693,522 A | 12/1997 | Chada et al. |
| 5,846,538 A | 12/1998 | Cheever et al. |
| 5,869,445 A | 2/1999 | Cheever et al. |
| 5,916,588 A | 6/1999 | Popescu et al. |
| 6,015,567 A | 1/2000 | Hudziak et al. |
| 6,083,505 A | 7/2000 | Miller et al. |
| 6,090,406 A | 7/2000 | Popescu et al. |
| 6,110,929 A | 8/2000 | Gerster et al. |
| 6,207,646 B1 | 3/2001 | Krieg et al. |
| 6,239,116 B1 | 5/2001 | Krieg et al. |
| 6,284,772 B1 | 9/2001 | Pitzer et al. |
| 6,299,884 B1 | 10/2001 | Van Nest et al. |
| 6,333,164 B1 | 12/2001 | Takesako |
| 6,352,505 B1 | 3/2002 | Bortz |
| 6,379,301 B1 | 4/2002 | Worthington et al. |
| 6,429,199 B1 | 8/2002 | Krieg et al. |
| 6,440,992 B1 | 8/2002 | Gerster et al. |
| 6,451,325 B1 | 9/2002 | Van Nest et al. |
| 6,500,855 B1 * | 12/2002 | Lam et al. ............... 514/415 |
| 6,551,276 B1 | 4/2003 | Mann et al. |
| 6,571,128 B2 | 5/2003 | Lebel et al. |
| 6,605,617 B2 | 8/2003 | Renhowe et al. |
| 6,627,640 B2 | 9/2003 | Gerster et al. |
| 6,630,161 B1 | 10/2003 | Leesman |
| 6,656,114 B1 | 12/2003 | Poulsen et al. |
| 6,656,938 B2 | 12/2003 | Crooks et al. |
| 6,660,735 B2 | 12/2003 | Crooks et al. |

(Continued)

FOREIGN PATENT DOCUMENTS

EP    0 109 942    5/1984

(Continued)

OTHER PUBLICATIONS

Yoshioka et al. (1996). "Synthesis of the Interferon-α Inducer Imiquimod by Thermal Electrocyclic Reactions of 1- and 2-Azahexatriene Systems," Chemical and Pharmaceutical Bulletin, Pharmaceutical Society of Japan, Tokyo, JP 44(4):709-714.
Minetti, P. et al. "2-n-Butyl-9-methyl-8-[1,2,3]triazol-2-yl-9H-purin-6-ylamine and Analogues as A2A Adenosine Receptor Antagonists . . . " J. Med. Chem., 48(22): 6887-6896 (2005).
Ahmad and Chapnick, Infect Dis Clin North Am (1999) 13:113-133.
Allison and Byars, Res Immunol (1992) 143:519-525.
Andrianov et al., Adv Drug Delivery Review (1998) 31(3):185-196.
Andrianov et al., Biomaterials (1998) 19(1-3):109-115.
Banerjee et al., PNAS USA (2004) 101(34):12652-12657.
Barr et al., Advanced Drug Delivery Reviews (1998) 32:247-271.

(Continued)

*Primary Examiner* — D M Seaman
*Assistant Examiner* — Niloofar Rahmani
(74) *Attorney, Agent, or Firm* — Helen Lee; Otis Littlefield

(57) ABSTRACT

The invention provides novel compositions comprising Imidazopyridine compounds. Also provided are methods of administering the compositions in an effective amount to enhance the immune response of a subject. Further provided are novel compositions and methods of administering the compositions in combination with (an)other agent(s).

10 Claims, No Drawings

U.S. PATENT DOCUMENTS

| | | |
|---|---|---|
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,699,703 B1 | 3/2004 | Doucette-Stamm et al. |
| 6,703,402 B2 | 3/2004 | Gerster et al. |
| 6,743,920 B2 | 6/2004 | Lindstrom et al. |
| 6,756,361 B1 | 6/2004 | Fattom et al. |
| 6,800,624 B2 | 10/2004 | Crooks et al. |
| 6,800,744 B1 | 10/2004 | Doucette-Stamm et al. |
| 6,809,203 B2 | 10/2004 | Gerster et al. |
| 6,884,435 B1 | 4/2005 | O'Hagan et al. |
| 6,888,000 B2 | 5/2005 | Crooks et al. |
| 6,921,826 B2 | 7/2005 | Dellaria et al. |
| 6,924,271 B2 | 8/2005 | Averett et al. |
| 6,924,293 B2 | 8/2005 | Lindstrom |
| 6,959,351 B2 | 10/2005 | Gwilt et al. |
| 2002/0007173 A1 | 1/2002 | Kundig et al. |
| 2003/0158192 A1 | 8/2003 | Crooks et al. |
| 2003/0187016 A1 | 10/2003 | Crooks et al. |
| 2003/0187525 A1 | 10/2003 | Mann et al. |
| 2003/0212379 A1 | 11/2003 | Bylund et al. |
| 2004/0002422 A1 | 1/2004 | Wang et al. |
| 2004/0019048 A1 | 1/2004 | Crooks et al. |
| 2004/0138248 A1 | 7/2004 | Heppner et al. |
| 2004/0176984 A1 | 9/2004 | White et al. |
| 2004/0241192 A1 | 12/2004 | Valiante |
| 2005/0069555 A1 | 3/2005 | Barsanti et al. |
| 2005/0070556 A1 | 3/2005 | Averett et al. |
| 2005/0136065 A1 | 6/2005 | Valiante, Jr. |
| 2005/0215517 A1 | 9/2005 | Rossignol et al. |

FOREIGN PATENT DOCUMENTS

| | | |
|---|---|---|
| EP | 0 273 501 | 6/1990 |
| EP | 0 378 881 | 7/1990 |
| EP | 0 427 347 | 5/1991 |
| EP | 0 471 177 | 2/1992 |
| EP | 0 477 508 | 4/1992 |
| EP | 0 626 169 | 11/1994 |
| EP | 0 689 454 | 1/1996 |
| EP | 0 735 898 | 3/1999 |
| EP | 0 761 231 | 1/2000 |
| EP | 1338295 | 8/2003 |
| EP | 1177802 | 9/2004 |
| GB | 2220211 | 1/1990 |
| GB | 0026333.5 | 12/2000 |
| WO | WO-90/14837 | 12/1990 |
| WO | WO-91/02062 | 2/1991 |
| WO | WO-93/17712 | 9/1993 |
| WO | WO-93/18150 | 9/1993 |
| WO | WO-93/19780 | 10/1993 |
| WO | WO-94/00153 | 1/1994 |
| WO | WO-94/21292 | 9/1994 |
| WO | WO-95/17210 | 6/1995 |
| WO | WO-95/17211 | 6/1995 |
| WO | WO-96/11711 | 4/1996 |
| WO | WO-96/26741 | 9/1996 |
| WO | WO-96/29412 | 9/1996 |
| WO | WO-96/30514 | 10/1996 |
| WO | WO-96/33739 | 10/1996 |
| WO | WO-97/01640 | 1/1997 |
| WO | WO-97/37026 | 10/1997 |
| WO | WO-97/43303 | 11/1997 |
| WO | WO-98/04702 | 2/1998 |
| WO | WO-98/18930 | 5/1998 |
| WO | WO-98/18931 | 5/1998 |
| WO | WO-98/40100 | 9/1998 |
| WO | WO-98/42375 | 10/1998 |
| WO | WO-98/42721 | 10/1998 |
| WO | WO-98/57659 | 12/1998 |
| WO | WO-98/58668 | 12/1998 |
| WO | WO-99/11241 | 3/1999 |
| WO | WO-99/24578 | 5/1999 |
| WO | WO-99/27105 | 6/1999 |
| WO | WO-99/27960 | 6/1999 |
| WO | WO-99/28475 | 6/1999 |
| WO | WO-99/29693 | 6/1999 |
| WO | WO-99/36544 | 7/1999 |
| WO | WO-99/52549 | 10/1999 |
| WO | WO-99/53310 | 10/1999 |
| WO | WO-99/57280 | 11/1999 |
| WO | WO-99/58562 | 11/1999 |
| WO | WO-00/07621 | 2/2000 |
| WO | WO-00/22430 | 4/2000 |
| WO | WO-00/23105 | 4/2000 |
| WO | WO-00/27994 | 5/2000 |
| WO | WO-0029047 | 5/2000 |
| WO | WO-00/37494 | 6/2000 |
| WO | WO 00/38683 | 7/2000 |
| WO | WO-00/38683 | 7/2000 |
| WO | WO-00/56360 | 9/2000 |
| WO | WO-00/67161 | 11/2000 |
| WO | WO-01/08636 | 2/2001 |
| WO | WO-01/21152 | 3/2001 |
| WO | WO-01/21207 | 3/2001 |
| WO | WO-01/37869 | 5/2001 |
| WO | WO-01/52885 | 7/2001 |
| WO | WO-01/95935 | 12/2001 |
| WO | WO-02/02606 | 1/2002 |
| WO | WO-02/18383 | 3/2002 |
| WO | WO-02/18595 | 3/2002 |
| WO | WO-02/26757 | 4/2002 |
| WO | WO-02/34771 | 5/2002 |
| WO | WO-02/079243 | 10/2002 |
| WO | WO-02/085905 | 10/2002 |
| WO | WO-02/094851 | 11/2002 |
| WO | WO-03/002065 | 1/2003 |
| WO | WO-03/011223 | 2/2003 |
| WO | WO-03/011864 | 2/2003 |
| WO | WO 2003/011864 | 2/2003 |
| WO | WO-03/024480 | 3/2003 |
| WO | WO-03/024481 | 3/2003 |
| WO | WO-03/035836 | 5/2003 |
| WO | WO-03/043572 | 5/2003 |
| WO | WO-03/049762 | 6/2003 |
| WO | WO-03047426 | 6/2003 |
| WO | WO-03/068811 | 8/2003 |
| WO | WO-03/082272 | 10/2003 |
| WO | WO-03/093306 | 11/2003 |
| WO | WO-03/097641 | 11/2003 |
| WO | WO-2004/005473 | 1/2004 |
| WO | WO-2004009161 | 1/2004 |
| WO | WO-2004/018455 | 3/2004 |
| WO | WO-2004/041157 | 5/2004 |
| WO | WO-2004/060308 | 7/2004 |
| WO | WO-2004/064715 | 8/2004 |
| WO | WO-2004/064759 | 8/2004 |
| WO | WO-2004/071459 | 8/2004 |
| WO | WO-2004/076677 | 9/2004 |
| WO | WO-2004/087153 | 10/2004 |
| WO | WO-2004/092360 | 10/2004 |
| WO | WO-2005/002619 | 1/2005 |
| WO | WO-2005/032582 | 4/2005 |
| WO | WO-2005/123080 | 12/2005 |
| WO | WO-2006/002422 | 1/2006 |
| WO | WO-2006009832 | 1/2006 |
| WO | 2006029115 * | 3/2006 |
| WO | WO-2006/029115 | 3/2006 |
| WO | WO 2006/029115 | 3/2006 |
| WO | WO-2006/031878 | 3/2006 |
| WO | WO 2006/031878 | 3/2006 |
| WO | WO-2006/115509 | 11/2006 |

OTHER PUBLICATIONS

Beignon et al., Infect Immunity (2002) 70(6):3012-3019.
Bell, Pediatr Infect Dis J (2000) 19:1187-1188.
Bhagat et al., BBRC (2003) 300:853-861.
Bjune et al., Lancet (1991) 338(8775):1093-1096.
Blackwell et al., J Immunol (2003) 170(8):4061-4068.
Buttery and Moxon, J R Coil Physicians Long (2000) 34:163-168.

Carl and Dasch, J Autoimmun (1989) 2 Suppl:81-91.
Chao et al., Biochim Biophys Acta (2004) 1702(2)145-152.
Chaux et al., J Exp Med (1999) 189:767-778.
Cooper, Pharm Biotechnol (1995) 6:559-580.
Costantino et al., Vaccine (1992) 10:691-698.
Costantino et al., Vaccine (1999) 17:1251-1263.
Dale, Infect Disclin Nort Am (1999) 13:227-243.
Dale, Vaccine (1996) 14(10):944-948.
Dale, Vaccine (1999) 17:193-200.
Davis et al., J Leukocyte Biol (2003) 23:3-29.
Del Guidice et al., Molecular Aspects of Medicine (1998) 19:1-70.
Dermine et al., British Medical Bulletin (2002) 62:149-162.
Dick, Conjugate Vaccines, Contrib Microbiol Immunol, Cruse et al., eds., Basel, Karger, 1989, vol. 10, pp. 48-114.
Domenighini et al., Mol Microbiol (1995) 15(6):1165-1167.
Dreesen, Vaccine (1997) 15 Suppl:S2-S6.
Espinoza-Delgado, The Oncologist (2002) 7(Suppl 3):20-33.
Evans et al., Expert Rev Vaccines (2003) 2:219-229.
Ferretti et al., PNAS USA (2001) 98:4658-4663.
Fields et al., Infect Immun (1999) 67(10):5395-5408.
Frey et al., Vaccine (2003) 21:4234-4237.
Fuskasawa et al., Vaccine (1999) 17:2951-2958.
Gaudernack, Immunotechnology (1996) 2:3-9.
Gerber et al., J Virology (2001) 75(10):4752-4760.
Gerlich et al., Vaccine (1990) 8 Suppl: S79-S80 and S93-S94.
Gluck et al., Vaccine (2002) 20:B10-B16.
Gold et al., J Exp Med (1965) 122:467-468.
Goldblatt, J Med Microbiol (1998) 47:563-567.
Grosfeld et al., Infect Immun (2003) 71(1):374-383.
Gustafsson et al.,N. Engl J Med (1996) 334:349-355.
Han et al., *Impact of Vitamin E on Immune Function and Infectious Diseases in the Aged* at Nutrition, Immune functions and Health EuroConference, Paris, Jun. 9-10, 2005.
Hariharan et al., Cancer Res (1995) 55:3486-3489.
Hill et al., Infect Immun (1997) 65(11):4476-4482.
Houghton et al., Hepatology (1991) 14:381-388.
Hsu et al., Clin Liver Dis (1999) 3:901-915.
International Preliminary Report on Patentability for PCT/US2007/064857, issued on Sep. 23, 2008, 14 pages.
International Search Report for PCT/US2007/064857, mailed on Nov. 6, 2007, 5 pages.
Iwarson, APMIS (1995) 103:321-326.
Jedrzejas, Microbiol Mol Biol Rev (2001) 65:187-207.
Johnson et al., Bioorg Med Chem Lett (1999) 9:2273-2278.
Johnstone et al., J Gen Virol (2004) 85(Pt 11):3229-3238.
Jones, Curr Opin Investig Drugs (2003) 4(2):214-218.
Kalman et al., Nature Genetics (1999) 21:385-389.
Kandimalla et al., BBRC (2003) 306:948-953.
Kandimalla et al., Biochem Soc Trans (2003) 31(Part 3):654-658.
Kandimalla et al., Nucleic Acids Research (2003) 31(9):2393-2400.
Krieg, Nature Medicine (2003) 9(7):831-835.
Krieg, TRENDS in Immunol (2002) 23(2):64-65.
Kuroda et al., Lancet (2001) 357(9264):1218-1219 and 1225-1240.
Lawrenz, Clin Microbiol (1999) 37(12):3997-4004.
Lee, "Diffusion-Controlled Matrix Systems," in *Treatise on Controlled Drug Delivery*, Kydonieus, ed., Marcel Dekker, Inc., New York, 1992, pp. 155-198.
Lenz et al., J immunol (2001) 5346-5355.
Liang et al., Infect Immun (2003) 71(10):5498-5504.
Lindberg, Vaccine (1999) 17(Suppl 2):S28-S36.
Livingston et al., Cancer Immunol Immunother (1997) 45:1-6.
Livingston et al., Cancer Immunol Immunother (1997) 45:10-19.
MacKay, "Pocket Pets," Animal Issues, vol. 32, Issue 1, Spring 2001, retrieved online at <http://www.bornfreeusa.org/articles.php?more=1&p=350>.
Mattson and Chan, Science (2003) 301:1847-1849.
McCluskie et al., FEMS Immunol Med Microbiol (2002) 32:179-185.
McMichael, Vaccine (2000) 19(Suppl 1):S101-S107.
Meraldi et al., Vaccine (2003) 21:2485-2491.
Minakawa and Matsuda, Tetrahedron (1993) 49(3):557-570.
Minakawa et al., J Organic Chem (1999) 64(19):7158-7172.
Minnetti et al., J Med Chem (48(22):6887-6896.
Mischler and Metcalfe, Vaccine (2002) 20(Suppl 5):B17-B23.

MMWR Morb Mortal Wkly Rep (1998) 47(1):9 and 12.
Moingeon, Vaccine (2001) 19:1305-1326.
Niikura et al., Virology (2002) 293:273-280.
Noppa et al., Infect Immun (2001) 69(5):3323-3334.
Offringa et al., Curr Opin Immunol (2000) 2:576-582.
O'Hagan and Valiante, Nat. Rev. Drug Discovery (2003) 2(9):727-735.
Old et al., J Exp Med (1998) 187:1163-1167.
Olsen et al., Infect Immun (2004) 72(10):6148-6150.
Ott et al., "MF59—Design and Evaluation of a Safe and Potent Adjuvant for Human Vaccines," in *Vaccine Design: The Subunit and Adjuvant Approach*, Powell and Newman, eds., Plenum Press, New York, 1995, pp. 277-296.
Ouchi et al., J Infect Dis (2000) 181 (Suppl 3): S441-S443.
Pajak et al., Vaccine (2003) 21:836-842.
Partidos et al., Immunol Lett (1999) 67(3):209-216.
Peppoloni et al., Vaccine (2003) 2(2):285-293.
Pine et al., J Control Release (2002) 85(1-3):263-270.
Pinto et al., J Infect Dis (2003) 188:327-338.
Pizza et al., Int J Med Microbiol (2000) 290(4-5):455-461.
Pizza et al., Science (2000) 287:1816-1820.
Pizza et al., Vaccine (2001) 19:2534-2541.
Plante et al., J Infect Dis (2000) 182:848-855.
Podda, Vaccine (2001) 19:2673-2680.
Podda and Del Guidice, Expert Rev Vaccines (2003) 2:197-203.
Price et al., Infect Immun (2004) 71(1):277-283.
Ramsay et al., Lancet (2001) 357(9251):195-196.
Rappuoli et al., TibTech (1991) 9:232-238.
Raz et al., PNAS USA (1994) 91:9519-9523.
Read et al., Nucleic Acids Res (2000) 28:1397-1406.
Ron and Langer, "Erodible Systems," in *Treatise on Controlled Drug Delivery*, Kydonieus, ed., Marcel Dekker, Inc., New York, 1992, pp. 199-224.
Rosenberg, Immunity (1999) 10:281-287.
Rosenberg, Immunol Today (1997) 18:175-182.
Rosenberg, Nature (2001) 411:380-384.
Rosenqvist et al., Dev Biol Strand (1998) 92:323-333.
Ross et al., Vaccine (2001) 19:135-142.
Roy et al., Can J Biochem Cell Biol (1984) 62(5):270-275.
Rubin, Pediatr Clin North Am (2000) 47:269-285.
Ryan et al., Infect Immunity (1999) 67(12):6270-6280.
Sabroe et al., J Immunol (2003) 1630-1635.
Sahin et al., Curr Opin Immunol (1997) 9:709-716.
Scharton-Kersten et al., Infect Immunity (2000) 68(9):5306-5313.
Schuchat, Lancet (1999) 353(9146):51-56.
Signorelli and Hadden, Int Immunopharmacol (2003) 3(8):1177-1186.
Singh et al., J. Cont. Rel. (2001) 70:267-276.
Singh et al., Pharm Res (2004) 21(12):2148-2152.
Sjolander et al., Advanced Drug Delivery Reviews (1998) 32:321-338.
Stanley, Clin Exp Dermatol (2002) 27(7):571-577.
Sutter et al., Pediatr Clin North Am (2000) 47:287-308.
Suzuki et al., Infect Immun (2004) 72(7):3829-3837.
Taylor-Papadimitriou, Immunol Today (1997) 18:105-107.
Tettelin et al., Science (2000) 287:1809-1815.
Theobald et al., PNAS USA (1995) 92:11993-11997.
Thompson et al., J Leukoc Biol (2005) 78:1273-1280.
Thompson et al., Methods in Molecular Medicine (2003) 94:255-266.
U.S. Appl. No. 60/582,654, filed Jun. 24, 2004 [Valiante et al.].
Van Den Eynde et al., Curr Opin Immunol (1995) 7:674-681.
Vasilakos et al., Cell Immunol. (2000) 204:64-74.
Warren et al., Ann. Rev. Immunol. (1986) 4:369-388.
Watson, Pediatr Infect Dis J (2000) 19:331-332.
Wong et al., J Clin Pharmacol (2003) 43(7):735-742.
Wu et al., Antiviral Res. (2004) 64(2):79-83.
Xu et al., Infect Immun (2002) 70(8):4414-4423.
Zhao et al., J Exp Med (1995) 182:67-74.
Zhu et al., Vaccine (2004) 22:660-669.
Zimmerman and Spann, Am Fan Physician (1999) 59:113-118, 125-126.

* cited by examiner

IMMUNOPOTENTIATING COMPOUNDS

CROSS REFERENCE TO RELATED APPLICATIONS

This application is the national phase of PCT application PCT/US2007/064857 having an international filing date of Mar. 23, 2007, which claims the benefit under 35 U.S.C. §119(e) of U.S. Provisional Application Ser. No. 60/785,539, filed on Mar. 23, 2006, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002107700SEQLISTING.txt, date recorded: Sep. 23, 2011, size: 2 KB).

FIELD OF THE INVENTION

The present invention generally relates to small molecule immune potentiators (SMIPs) that are novel imidazopyridine compounds or derivatives thereof that are capable of stimulating or modulating an immune response in a subject. The invention also relates to novel combinations of antigens with the immune potentiators that may be used in vaccine therapies. In some embodiments, the compounds can be used as immunotherapeutic agents for proliferative diseases, infectious diseases, autoimmune diseases, allergies, and/or asthma.

BACKGROUND OF THE INVENTION

Issued U.S. Pat. Nos. 4,689,338, 5,389,640, 5,268,376, 4,929,624, 5,266,575, 5,352,784, 5,494,916, 5,482,936, 5,346,905, 5,395,937, 5,238,944, 5,525,612, and 6,110,929, and WO 99/29693 disclose imidazoquinoline compounds of the general structure (a) for use as "immune response modifiers":

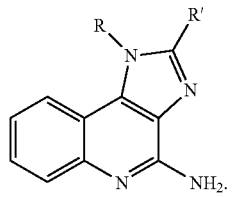

(a)

Each of these references is hereby incorporated by reference in its entirety and for all purposes as if fully set forth herein.

U.S. Pat. No. 6,083,505, describes specific imidazoquinolines for use as adjuvants. WO 03/097641 discloses the use of certain imidazoquinolines and salts thereof for the treatment of certain protein kinase dependent diseases and for the manufacture of pharmaceutical preparations for the treatment of diseases.

Immune response to certain antigens can be enhanced through the use of immune potentiators, known as vaccine adjuvants. Such adjuvants potentiate the immune response to specific antigens and are, therefore, the subject of considerable interest and study within the medical community.

Research has resulted in the development of vaccines possessing antigenic epitopes that were previously impossible to produce. For example, currently available vaccine candidates include synthetic peptides mimicking numerous bacterial and viral antigens. The immune response to these purified antigens can be enhanced by coadministration of an adjuvant. Unfortunately, conventional vaccine adjuvants possess a number of drawbacks that limit their overall use and effectiveness. Moreover, many of the adjuvants currently available have limited utility because they include components that are not metabolized by humans. Additionally, most adjuvants are difficult to prepare and may require time-consuming procedures and, in some cases, the use of elaborate and expensive equipment to formulate a vaccine and adjuvant system.

Immunological adjuvants are described in "Current Status of Immunological Adjuvants", Ann. Rev. Immunol., 1986, 4, pp. 369-388, and "Recent Advances in Vaccine Adjuvants and Delivery Systems" by Derek T O'Hagan and Nicholas M. Valiante. See also U.S. Pat. Nos. 4,806,352; 5,026,543; and 5,026,546 for disclosures of various vaccine adjuvants appearing in the patent literature. Each of these references is hereby incorporated by reference in its entirety and for all purposes as if fully set forth herein.

Efforts have been made to identify new immune modulators for use as adjuvants for vaccines and immunotherapies that would overcome the drawbacks and deficiencies of conventional immune modulators. In particular, an adjuvant formulation that elicits potent cell-mediated and humoral immune responses to a wide range of antigens in humans and domestic animals, but lacking the side effects of conventional adjuvants and other immune modulators, would be highly desirable. This need could be met by small molecule immune potentiators (SMIPs) because the small molecule platform provides diverse compounds for the selective manipulation of the immune response, necessary for increasing the therapeutic index immune modulators.

Novel sole-acting agents with varied capacities for altering levels and/or profiles of cytokine production in human immune cells are needed. Compounds with structural disparities will often elicit a desired response through a different mechanism of action, or with greater specificity to a target, such as a dendritic cell, modulating potency and lowering side effects when administered to a patient.

The immunosuppressive effect of cytostatic substances has rendered them useful in the therapy of autoimmune diseases such as multiple sclerosis, psoriasis and certain rheumatic diseases. Unfortunately, their beneficial effect has to be weighed against serious side effects that necessitate dosages that are too low. Furthermore, interruption of the treatment may be required.

Agents and/or combinations of active substances that result in significantly improved cytostatic or cytotoxic effects compared to conventional cytostatics e.g., vincristin, methotrexate, cisplatin, etc., are needed. With such agents and combinations, chemotherapies may be offered that combine increasing efficiency with a large reduction of side effects and therapeutic doses. Such agents and combination therapies may thus increase the therapeutic efficiency of known cytostatic drugs. In some embodiments, the compounds of the invention are used in combination with compounds that provide significantly improved cytostatic or cytotoxic effect compared to conventional cytostatic agents when administered alone. Additionally, cell lines that are insensitive to conventional chemotherapeutic treatment may also be susceptible to chemotherapy using combinations of active substances.

Improved methods for preparing therapeutics that serve to augment natural host defenses against viral and bacterial infections, or against tumor induction and progression, with reduced cytotoxicity, are needed. The present invention provides such methods, and further provides other related advantages. The current invention provides method of preparing therapeutic and prophylactic agents for treatment of disease states characterized by other immune deficiencies, abnormalities, or infections including autoimmune diseases and viral and bacterial infections responsive to compounds with the capacity to modulate cytokines and/or TNF-α.

BRIEF SUMMARY OF THE INVENTION

The instant invention provides novel immune potentiators, immunogenic compositions, novel compounds and pharmaceutical compositions, and novel methods of administering a vaccine, by administering small molecule immune potentiators alone or in combination with antigens and/or other agents. The invention further provides novel compounds and pharmaceutical compositions, for use in the treatment of cancer, precancerous lesions, autoimmune diseases, infectious diseases, allergies, and asthma. The invention further provides the use of the compounds of the invention in the manufacture of medicaments for use in the treatment of cancer, precancerous lesion, autoimmune diseases, allergies, and asthma.

The imidazopyridine compounds or derivatives thereof used in the methods and compositions of the invention are inexpensive to produce and easy to administer. They have potential for finer specificity compared to existing immunostimulants, thus providing improved efficacy and safety profiles.

As adjuvants, the imidazopyridine compounds or derivatives thereof may be combined with numerous antigens and delivery systems to form an immunogenic composition. In a preferred embodiment, the immunogenic composition can be used in the manufacture of a vaccine or a medicament.

As immunotherapeutics, the imidazopyridine compounds or derivatives thereof are used alone or in combination with other therapies (e.g., anti-virals, anti-bacterials, other immune modulators or in therapeutic vaccine antigens) for treatment of the following: persistent of chronic viral infections such as, e.g., those caused by the human immunodeficiency virus (HIV), the hepatitis C virus (HCV), the hepatitis B virus (HBV), the herpes simplex virus (HSV); persistent or chronic bacterial infections, such as those caused by *chalymidia, pseudomonas, gonorrheae, treponema pallidium* (syphilis), *H. pylori*, tuberculosis, Lyme disease; chronic or persistent fungal infections, chronic or persistent parasitic infections (e.g., malaria); as well as medicaments for the reduction of tumor growth or modulation of abnormal cellular proliferation associated with diseases such as actinic keratosis, atypical or dysplastic nevi, or premalignant lentigos.

The imidazopyridine compounds or derivatives thereof of the present invention may target substrates in the disease state, such as, for example particular kinases including EGFr, c-Kit, bFGF, Kdr, CHK1, CDK, cdc-2, Akt, PDGF, PI3K, VEGF, PKA, PKB, src, c-Met, Abl, Ras, RAF, and MEK, among others.

As immunotherapeutics, the imidazopyridine compounds or derivatives thereof may also be used for the treatment of cancer either alone or in combination with other anti-cancer therapies (e.g., chemotherapeutic agents, (monoclonal antibodies) mAbs or other immune potentiators). In addition, certain imidazopyridines with the capacity to induce Type 1 cytokines (e.g., IL-12, TNF-α or IFN's) may be used for the treatment of allergies and/or asthma due to their capacity to steer the immune response towards more benign sequelae. The imidazopyridine compounds or derivatives thereof may be used, for example, for the treatment of *bacillus* Calmette-Guerin (BCG), cholera, plague, typhoid, hepatitis B infection, influenza, inactivated polio, rabies, measles, mumps, rubella, oral polio, yellow fever, tetanus, diphtheria, *hemophilus influenzae* b, meningococcus infection, and pneumococcus infection. The imidazopyridine compounds or derivatives thereof may be used in an anti cell proliferative effective amount for the treatment of cancer. The imidazopyridine compounds or derivatives thereof may also be used in anti-Th2/Type2 cytokine amount for the deviation of allergic/asthmatic immune responses.

In some embodiments, methods of treating cancer and/or precancerous lesions are provided. In such embodiments, one or more known anticancer agent is combined with one or more imidazopyridine compound to reduce tumor growth in a subject. A number of suitable anticancer agents are contemplated for use in the methods of the present invention and are described more thoroughly in the following detailed description.

In accordance with another embodiment, there is provided a method of inhibiting tumor cell growth in a subject. The method includes administering to a subject an effective dose of a combination comprising at least one compound as described herein, and a monoclonal antibody (mAb). The combination may be more effective at inhibiting such cell growth than when the mAb is administered by itself. In some embodiments of the methods of treating cancer with the combination, an additional imidazopyridine compound as described herein and/or mAb, is administered to the subject.

In some embodiments, the invention provides immunogenic compositions comprising an antigen and an imidazo[4,5-c]pyridine-2,4-diamine effective to stimulate a cell mediated response to said antigen. In some embodiments, the imidazo[4,5-c]pyridine-2,4-diamine compounds have the general Formulas described herein. Accordingly, in some embodiments of the methods and compositions of the invention, the imidazopyridine compound has the Formula (I):

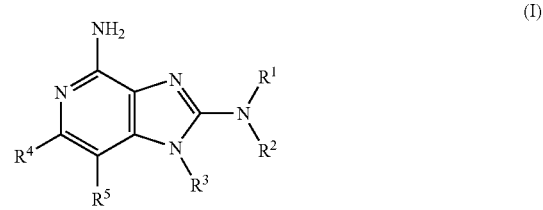

(I)

wherein:
R$^1$ and R$^2$ are each, independently, selected from H, C$_{1-6}$ alkyl, C$_{1-6}$ alkoxy, C$_{1-6}$ alkoxy-C$_{1-6}$ alkyl, C$_{6-10}$ aryl, heterocyclyl, C$_{3-14}$ cycloalkyl, —C(═O)NR$^7$R$^8$, —C(═O)R$^9$, —C(═O)OR$^9$, —S(═O)$_q$R$^{10}$, C$_{6-10}$ aryl-C$_{1-6}$ alkyl, C$_{6-10}$ aryloxy-C$_{1-6}$ alkyl, —(CH$_2$)$_m$CH═CH(CH$_2$)$_n$R$^6$, and —(CH$_2$)$_m$C≡C(CH$_2$)$_n$R$^6$ wherein each of the C$_{1-6}$ alkyl, C$_{1-6}$ alkoxy, C$_{1-6}$ alkoxy-C$_{1-6}$ alkyl, C$_{6-10}$ aryl, heterocyclyl, C$_{3-14}$ cycloalkyl, C$_{6-10}$ aryl-C$_{1-6}$ alkyl and C$_{6-10}$ aryloxy-C$_{1-6}$ alkyl is optionally substituted by up to 10 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^a$, SR$^a$, C(═O)R$^b$, C(═O)NR$^c$R$^d$, C(═O)OR$^a$, C(═S)NR$^c$R$^d$, OC(═O)

$R^b$, $OC(=O)NR^cR^d$, $NR^cR^d$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

or $R^1$ and $R^2$ together with the N atom to which they are attached form a heterocycloalkyl group optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d C(=O)OR^a$, $C(=S)NR^cR^d$, $OC(=O)R^b$, $OC(=O)NR^cR^d$, $NR^cR^d$, $NR^cC(=O)R^d NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

$R^3$ is H, $C_{1-6}$ alkyl, $C_{6-10}$ aryl, heterocyclyl, $C_{3-14}$ cycloalkyl, $-(CH_2)_mCH=CH(CH_2)_nR^6$, $-(CH_2)_mC\equiv C(CH_2)_nR^6$, $-C(=O)NR^7R^8$, $-C(=O)R^9$, $-C(=O)OR^9$, or $-S(=O)_qR^{10}$, wherein each of the $C_{1-6}$ alkyl, $C_{6-10}$ aryl, heterocyclyl, $C_{3-14}$ cycloalkyl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d$, $C(=O)OR^a$, $C(=S)NR^cR^d$, $OC(=O)R^b$, $OC(=O)NR^cR^d$, $NR^cR^d$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

$R^4$ and $R^5$ are each, independently, selected from H, $C_{1-6}$ alkyl, $C_{1-6}$ alkoxy, halogen, trihalomethyl, $-NR^7R^8$, $-OR^9$, $-C(=O)R^9$, $-C(=O)OR^9$, $-C(=O)NR^7R^8$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$ wherein the $C_{1-6}$ alkyl or $C_{1-6}$ alkoxy is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d$, $C(=O)OR^a$, $C(=S)NR^cR^d$, $OC(=O)R^b$, $OC(=O)NR^cR^d$, $NR^cR^b$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

or $R^4$ and $R^5$ together with the two carbon atoms to which they are attached form a 5-7 membered cycloalkyl, a 5-7 membered heterocycloalkyl, or a 5-7 membered heteroaryl group, each optionally substituted by 1, 2, 3, 4 or 5 $R^{12}$;

each $R^6$ is independently H, halo, $C_{1-6}$ alkyl, $C_{2-6}$ alkenyl, $C_{6-10}$ aryl, $C(=O)OH$, or $C(=O)O-(C_{1-6}$ alkyl), wherein each of the $C_{1-6}$ alkyl, $C_{2-6}$ alkenyl and $C_{6-10}$ aryl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}$, $C(=O)R^{b'}$, $C(=O)NR^{c'}R^{d'}$, $C(=O)OR^{a'}$, $C(=S)NR^{c'}R^{d'}$, $OC(=O)R^{b'}$, $OC(=O)NR^{c'}R^{d'}$, $NR^{c'Rd'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

$R^7$ and $R^8$ are each, independently, selected from H, $C_{1-6}$ alkyl, $C_{1-6}$ alkoxy-$C_{1-6}$ alkyl, $C_{6-10}$ aryl, $C_{6-10}$ aryl-$C_{1-6}$ alkyl, $C_{6-10}$ aryloxy-$C_{1-6}$ alkyl, $-(CH_2)_mCH=CH(CH_2)_nR^{11}$, and $-(CH_2)_mC\equiv C(CH_2)_nR^{11}$, wherein each of the $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl and $C_{6-10}$ aryloxy-$C_{1-6}$ alkyl is optionally substituted by up to 10 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}$, $C(=O)R^{b'}$, $C(=O)NR^{c'}R^{d'}$, $C(=O)OR^{a'}$, $C(=S)NR^{c'}R^{d'}$, $OC(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

or $R^7$ and $R^8$ together with the N atom to which they are attached form a heterocyclyl group optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}$, $C(=O)R^{b'}$, $C(=O)NR^{c'}R^{d'}$, $C(=O)OR^{a'}$, $C(=S)NR^{c'}R^{d'}$, $OC(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

each $R^9$ is independently H, $C_{6-10}$ aryl, $C_{3-14}$ cycloalkyl, heterocyclyl, or $C_{1-6}$ alkyl optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}C(=O)R^{b'}$, $C(=O)NR^{c'}R^{d'}$, $C(=O)OR^{a'}$, $C(=S)NR^{c'}R^{d'}$, $OC(=O)R^{b'}C(=O)NR^{c'}R^{d'}$, $NR^{c'}R^{d'}$, $NR^cC(=O)R^{d'}$, $NR^cC(=O)OR^{a'}$, $NR^{c'}S(=O)_2R^{b'}$, $S(=O)R^b$, $S(=O)NR^{c'}R^{d'}$, $S(=O)_2OH$, $S(=O)_2R^{b'}$, and $S(=O)_2NR^cR^d$;

each $R^{10}$ is independently $C_{1-6}$ alkyl, $C_{2-6}$ alkenyl, $C_{6-10}$ aryl, $C_{3-14}$ cycloalkyl, heterocyclyl, $C_{6-10}$ aryl-$C_{1-6}$ alkyl, trihalomethyl, or $-NR^7R^8$, wherein each of the $C_{1-6}$ alkyl, $C_{2-6}$ alkenyl, $C_{6-10}$ aryl, $C_{3-14}$ cycloalkyl, heterocyclyl, and $C_{6-10}$ aryl-$C_{1-6}$ alkyl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}C(=O)R^{b'}$, $C(=O)NR^{c'}R^{d'}$, $C(=O)OR^{a'}$, $C(=S)NR^{c'}R^{d'}$, $OC(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

each $R^{11}$ is independently H, halo, $C_{1-6}$ alkyl, $C_{2-6}$ alkenyl, $C_{6-10}$ aryl, $C(=O)OH$, or $C(=O)O-(C_{1-6}$ alkyl), wherein each of the $C_{1-6}$ alkyl, $C_{2-6}$ alkenyl and $C_{6-10}$ aryl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a''}$, $SR^{a''}$, $C(=O)R^{b''}$, $C(=O)NR^{c''}R^{d''}$, $C(=O)OR^{a''}$, $C(=S)NR^{c''}R^{d''}$, $OC(=O)R^{b''}$, $OC(=O)NR^{c''}R^{d''}$, $NR^{c''}R^{d''}$, $NR^{c''}C(=O)R^{b''}$, $NR^{c''}C(=O)OR^{a''}$, $NR^{c''}S(=O)_2R^{b''}$, $S(=O)R^{b''}$, $S(=O)NR^{c''}R^{d''}$, $S(=O)_2OH$, $S(=O)_2R^{b''}$, and $S(=O)_2NR^{c''}R^{d''}$;

each $R^{12}$ is independently $C_{1-6}$ alkyl, $C_{1-6}$ alkoxy, halogen, trihalomethyl, $-NR^7R^8$, $-OR^9$, $-C(=O)R^9$, $-C(=O)OR^9$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$, or $-C(=O)NR^7R^8$, wherein the $C_{1-6}$ alkyl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d$, $C(=O)OR^a$, $C(=S)NR^cR^d$, $OC(=O)R^b$, $OC(=O)NR^cR^d$, $NR^cR^d$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

$R^a$, $R^{a'}$ and $R^{a''}$ are each, independently, selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl, wherein each of the $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocycloalkyl is optionally substituted by 1, 2 or 3 substituents independently selected from OH, CN, $NO_2$, oxo, $C_{1-6}$ alkoxy, amino, halo, $C_{1-6}$ alkyl, $C_{1-6}$ haloalkyl, $C_{1-6}$ haloalkoxy, aryl, arylalkyl, heteroaryl, heteroarylalkyl, cycloalkyl and heterocycloalkyl;

$R^o$, $R^{o'}$ and $R^{b'}$ are each, independently, selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl, wherein each of the $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl is optionally substituted by 1, 2 or 3 substituents independently selected from OH, CN, NO$_2$, oxo, $C_{1-6}$ alkoxy, amino, halo, $C_{1-6}$ alkyl, $C_{1-6}$ haloalkyl, $C_{1-6}$ haloalkoxy, aryl, arylalkyl, heteroaryl, heteroarylalkyl, cycloalkyl and heterocycloalkyl;

$R^c$ and $R^d$ are each, independently, selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl, wherein each of the $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl is optionally substituted by 1, 2 or 3 substituents independently selected from OH, CN, NO$_2$, oxo, $C_{1-6}$ alkoxy, amino, halo, $C_{1-6}$ alkyl, $C_{1-6}$ haloalkyl, $C_{1-6}$ haloalkoxy, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group;

$R^{c'}$ and $R^{d'}$ are each, independently, selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl, wherein each of the $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl is optionally substituted by 1, 2 or 3 substituents independently selected from OH, CN, NO$_2$, oxo, $C_{1-6}$ alkoxy, amino, halo, $C_{1-6}$ alkyl, $C_{1-6}$ haloalkyl, $C_{1-6}$ haloalkoxy, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group;

$R^{c''}$ and $R^{d''}$ are each, independently, selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl, wherein each of the $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl is optionally substituted by 1, 2 or 3 substituents independently selected from OH, CN, NO$_2$, oxo, $C_{1-6}$ alkoxy, amino, halo, $C_{1-6}$ alkyl, $C_{1-6}$ haloalkyl, $C_{1-6}$ haloalkoxy, aryl, arylalkyl, heteroaryl, heteroarylalkyl, cycloalkyl and heterocycloalkyl;

or $R^{c''}$ and $R^{d''}$ together with the N atom to which they are attached form a 4-, 5-, 6- or 7-membered heterocycloalkyl group;

m and n are each, independently, selected from 0, 1, 2 and 3; and each q is independently 0, 1 or 2;

or a pharmaceutically acceptable sale thereof, a tautomer thereof, or a pharmaceutically acceptable salt of the tautomer.

Methods of manufacturing compounds and compositions described herein are provided and contemplated to fall within the scope of the invention as is the use of the imidazopyridines in methods for manufacturing medicaments for use in the methods of the invention.

In each of the embodiments of the invention, compounds of Formula (I) or (II), can be used in the manufacture of a medicament for enhancing the immune response to an antigen.

Other embodiments provide the use of the compounds of the invention, in the manufacture of medicament for immune stimulation, and another agent, such as an antigen, for simultaneous separate or sequential administration. In another more particular embodiment the use is for treating or preventing a bacterial or viral infection. In another embodiment the use is for treating cancer. In another embodiment the use is for preventing influenza infection.

Other embodiments provide a pharmaceutical preparation or system, comprising (a) a compound of Formula (I) or (II); and (b) an antigen, wherein (a) and (b) are either in admixture or are separate compositions. The agents are for simultaneous separate or sequential administration. In another more particular embodiment the use is for preventing a viral, bacterial, fungal or parasitic infection. In another embodiment the use is for treating cancer.

Further embodiments of the invention include those described in the detailed description.

DETAILED DESCRIPTION OF THE INVENTION

Applicants have discovered methods of stimulating cytokine activity in cells and immunotherapeutics and/or vaccine adjuvants, that will provide effective treatments for disorders such as those described herein and those apparent to one skilled in the art.

In some embodiments, the invention provides a compound of Formula (I):

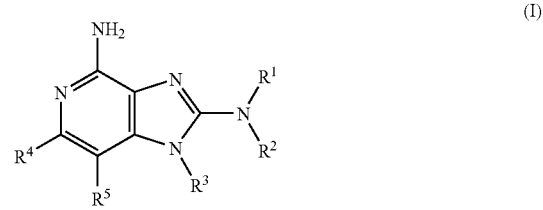

or a pharmaceutically acceptable salt thereof, a tautomer thereof, or a pharmaceutically acceptable salt of the tautomer, wherein:

$R^1$ and $R^2$ are each, independently, selected from H, $C_{1-6}$ alkyl, $C_{1-6}$ alkoxy, $C_{1-6}$ alkoxy-$C_{1-6}$ alkyl, $C_{6-10}$ aryl, heterocyclyl, $C_{3-14}$ cycloalkyl, —C(=O)NR$^7$R$^8$, —C(=O)R$^9$, —C(=O)OR$^9$, —S(=O)$_q$R$^{10}$, $C_{6-10}$ aryl-$C_{1-6}$ alkyl, $C_{6-10}$ aryloxy-$C_{1-6}$ alkyl, —(CH$_2$)$_m$CH=CH(CH$_2$)$_n$R$^6$, and —(CH$_2$)$_m$C≡C(CH$_2$)$_n$R$^6$, wherein each of the $C_{1-6}$ alkyl, $C_{1-6}$ alkoxy, $C_{1-6}$ alkoxy-$C_{1-6}$ alkyl, $C_{6-10}$ aryl, heterocyclyl, $C_{3-14}$ cycloalkyl, $C_{6-10}$ aryl-$C_{1-6}$ alkyl and $C_{6-10}$ aryloxy-$C_{1-6}$ alkyl is optionally substituted by up to 10 substituents independently selected from halo, oxo, imino, guanidino, amidino, CN, NO$_2$, $C_{1-6}$ alkyl, $C_{1-6}$ haloalkyl, $C_{6-10}$ aryl, $C_{3-14}$ cycloalkyl, heterocyclyl, OR$^a$, SR$^a$, C(=O)R$^b$, C(=O)NR$^c$R$^d$, C(=O)OR$^a$, C(=S)NR$^c$R$^d$, OC(=O)R$^b$, OC(=O)NR$^c$R$^d$, NR$^c$R$^d$, NR$^c$C(=O)R$^b$, NR$^c$C(=O)OR$^a$, NR$^c$S(=O)$_2$R$^b$, S(=O)R$^b$, S(=O)NR$^c$R$^d$, S(=O)$_2$OH, S(=O)$_2$R$^b$, and S(=O)$_2$NR$^c$R$^d$;

or $R^1$ and $R^2$ together with the N atom to which they are attached form a heterocycloalkyl group optionally substituted by 1, 2, 3, 4 or 5 substituents independently selected from halo, oxo, imino, guanidino, amidino, CN, NO$_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d$, $C(=O)OR^a$, $C(=S)NR^cR^d$, $OC(=O)R^b$, $OC(=O)NR^cR^d$, $NR^cR^d$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

$R^3$ is H, $C_{1-6}$ alkyl, $C_{6-10}$ aryl, heterocyclyl, $C_{3-14}$ cycloalkyl, $-(CH_2)_mCH=CH(CH_2)_nR^6$, $-(CH_2)_mC\equiv C(CH_2)_nR^6$, $-C(=O)NR^7R^8$, $-C(=O)R^9$, $-C(=O)OR^9$, or $-S(=O)_qR^{10}$, wherein each of the $C_{1-6}$ alkyl, $C_{6-10}$ aryl, heterocyclyl, $C_{3-14}$ cycloalkyl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d$, $C(=O)OR^a$, $C(=S)NR^cR^d$, $OC(=O)R^b$, $OC(=O)NR^cR^d$, $NR^cR^d$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

$R^4$ and $R^5$ are each, independently, selected from H, $C_{1-6}$ alkyl, $C_{1-6}$ alkoxy, halogen, trihalomethyl, $-NR^7R^8$, $-OR^9$, $-C(=O)R^9$, $-C(=O)OR^9$, $-C(=O)NR^7R^8$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$ wherein the $C_{1-6}$ alkyl or $C_{1-6}$ alkoxy is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d$, $C(=O)OR^a$, $C(=S)NR^cR^d$, $OC(=O)R^b$, $OC(=O)NR^cR^d$, $NR^cR^d$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

or $R^4$ and $R^5$ together with the two carbon atoms to which they are attached form a 5-7 membered cycloalkyl, a 5-7 membered heterocycloalkyl, or a 5-7 membered heteroaryl group, each optionally substituted by 1, 2, 3, 4 or 5 $R^{12}$;

each $R^6$ is independently H, halo, $C_{1-6}$ alkyl, $C_{2-6}$ alkenyl, $C_{6-10}$ aryl, $C(=O)OH$, or $C(=O)O-(C_{1-6}$ alkyl), wherein each of the $C_{1-6}$ alkyl, $C_{2-6}$ alkenyl and $C_{6-10}$ aryl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}C(=O)R^{b'}$, $C(=O)NR^{c'}R^{d'}$, $C(=O)OR^{a'}$, $C(=S)NR^{c'}R^{d'}$, $OC(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

$R^7$ and $R^8$ are each, independently, selected from H, $C_{1-6}$ alkyl, $C_{1-6}$ alkoxy-$C_{1-6}$ alkyl, $C_{6-10}$ aryl, $C_{6-10}$ aryl-$C_{1-6}$ alkyl, $C_{6-10}$ aryloxy-$C_{1-6}$ alkyl, $-(CH_2)_mCH=CH(CH_2)_nR^{11}$, and $-(CH_2)_mC\equiv C(CH_2)_nR^{11}$, wherein each of the $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl and $C_{6-10}$ aryloxy-$C_{1-6}$ alkyl is optionally substituted by up to 10 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}$, $C(=O)R^{b'}$, $C(=O)NR^{c'}R^{d'}$, $C(=O)OR^{a'}$, $C(=S)NR^{c'}R^{d'}$, $C(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

or $R^7$ and $R^8$ together with the N atom to which they are attached form a heterocyclyl group optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}$, $C(=O)R^{b'}$, $C(=O)NR^{c'}R^{d'}$, $C(=O)OR^{a'}$, $C(=S)NR^{c'}R^{d'}$, $OC(=O)R^{b'}$, $OC(=O)NR^{c'}R^{c'}$, $NR^{c'}R^{d'}$, $NR^{c}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

each $R^9$ is independently H, $C_{6-10}$ aryl, $C_{3-14}$ cycloalkyl, heterocyclyl, or $C_{1-6}$ alkyl optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a'}C(=O)R^{b'}$, $C(=O)NR^{c'}R^{d'}$, $C(=O)OR^{a'}$, $C(=S)NR^{c'}R^{d'}$, $OC(=O)R^{b'}$ $OC(=O)NR^{c'}R^{d'}$, $NR^{c'}R^{d'}$, $NR^{c'}C(=O)R^{d'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

each $R^{10}$ is independently $C_{1-6}$ alkyl, $C_{2-6}$ alkenyl, $C_{6-10}$ aryl, $C_{3-14}$ cycloalkyl, heterocyclyl, $C_{6-10}$ aryl-$C_{1-6}$ alkyl, trihalomethyl, or $-NR^7R^8$, wherein each of the $C_{1-6}$ alkyl, $C_{2-6}$ alkenyl, $C_{6-10}$ aryl, $C_{3-14}$ cycloalkyl, heterocyclyl, and $C_{6-10}$ aryl-$C_{1-6}$ alkyl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a'}$, $SR^{a}C(=O)R^{b'}$, $C(=O)NR^{c'}R^{d'}$, $C(=O)OR^{a'}$, $C(=S)NR^{c'}R^{d'}$, $OC(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2OH$, $S(=O)_2R^{b'}$, and $S(=O)_2NR^{c'}R^{d'}$;

each $R^{11}$ is independently H, halo, $C_{1-6}$ alkyl, $C_{2-6}$ alkenyl, $C_{6-10}$ aryl, $C(=O)OH$, or $C(=O)O-(C_{1-6}$ alkyl), wherein each of the $C_{1-6}$ alkyl, $C_{2-6}$ alkenyl and $C_{6-10}$ aryl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^{a''}$, $SR^{a''}$, $C(=O)R^{b''}$, $C(=O)NR^{c''}R^{d''}$, $C(=O)OR^{a''}$, $C(=S)NR^{c''}R^{d''}$, $OC(=O)R^{b''}$, $OC(=O)NR^{c''}R^{d''}$, $NR^{c''}R^{d''}$, $NR^{c''}C(=O)R^{b''}$, $NR^{c''}C(=O)OR^{a''}$, $NR^{c''}S(=O)_2R^{b''}$, $S(=O)R^{b''}$, $S(=O)NR^{c''}R^{d''}$, $S(=O)_2OH$, $S(=O)_2R^{b''}$, and $S(=O)_2NR^{c''}R^{d''}$;

each $R^{12}$ is independently $C_{1-6}$ alkyl, $C_{1-6}$ alkoxy, halogen, trihalomethyl, $-NR^7R^8$, $-OR^9$, $-C(=O)R^9$, $-C(=O)OR^9$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$, or $-C(=O)NR^7R^8$, wherein the $C_{1-6}$ alkyl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, $C(=O)R^b$, $C(=O)NR^cR^d$, $R^dC(=O)OR^a$, $C(=S)NR^cR^d$, $OC(=O)R^b$, $OC(=O)NR^cR^d$, $NR^cR^d$, $NR^cC(=O)R^b$, $NR^cC(=O)OR^a$, $NR^cS(=O)_2R^b$, $S(=O)R^b$, $S(=O)NR^cR^d$, $S(=O)_2OH$, $S(=O)_2R^b$, and $S(=O)_2NR^cR^d$;

$R^a$, $R^{a'}$ and $R^{a''}$ are each, independently, selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl, wherein each of the $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocycloalkyl is optionally substituted by 1, 2 or 3 substituents independently selected from OH, CN, $NO_2$, oxo, $C_{1-6}$ alkoxy, amino, halo, $C_{1-6}$ alkyl, $C_{1-6}$ haloalkyl, $C_{1-6}$ haloalkoxy, aryl, arylalkyl, heteroaryl, heteroarylalkyl, cycloalkyl and heterocycloalkyl;

$R^b$, $R^{b'}$ and $R^{b'}$ are each, independently, selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl, wherein each of the $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, heterocyclyl, $C_{6-10}$ aryl-$C_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

R$^c$ and R$^d$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

or R$^c$ and R$^d$ together with the N atom to which they are attached form a 4-, 5-, 6- or 7-membered heterocycloalkyl group;

R$^{c'}$ and R$^{d'}$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

or R$^{c'}$ and R$^{d'}$ together with the N atom to which they are attached form a 4-, 5-, 6- or 7-membered heterocycloalkyl group;

R$^{c''}$ and R$^{d''}$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

or R$^{c''}$ and R$^{d''}$ together with the N atom to which they are attached form a 4-, 5-, 6- or 7-membered heterocycloalkyl group;

m and n are each, independently, selected from 0, 1, 2 and 3; and each q is independently 0, 1 or 2.

In some embodiments, R$^1$ and R$^2$ are each, independently, selected from H, —(CH$_2$)$_m$CH═CH(CH$_2$)$_n$R$^6$, and C$_{1-6}$ alkyl, wherein the C$_{1-6}$ alkyl is optionally substituted by 1, 2, or 3 substituents independently selected from halo, OH, CN, NO$_2$, C$_{1-6}$ alkoxy and C$_{1-6}$ haloalkoxy.

In some embodiments, R$^1$ and R$^2$ are each, independently, selected from H and C$_{1-6}$ alkyl, wherein the C$_{1-6}$ alkyl is optionally substituted by 1, 2, or 3 substituents independently selected from halo, OH, CN, NO$_2$, C$_{1-6}$ alkoxy and C$_{1-6}$ haloalkoxy.

In some embodiments, R$^1$ and R$^2$ are each, independently, selected from H and C$_{1-4}$ alkyl, wherein the C$_{1-4}$ alkyl is optionally substituted by 1, 2, or 3 substituents independently selected from halo, OH, CN, NO$_2$, C$_{1-4}$ alkoxy and C$_{1-4}$ haloalkoxy.

In some embodiments, R$^1$ and R$^2$ are each, independently, selected from H and C$_{1-4}$ alkyl, wherein the C$_{1-4}$ alkyl is optionally substituted by 1, 2, or 3 substituents independently selected from OH and C$_{1-4}$ alkoxy.

In some embodiments, R$^1$ and R$^2$ are each, independently, C$_{1-4}$ alkyl optionally substituted by 1, 2, or 3 substituents independently selected from OH and C$_{1-4}$ alkoxy.

In some embodiments, R$^1$ and R$^2$ are each, independently, C$_{1-4}$ alkyl.

In some embodiments, R$^1$ and R$^2$ are each, independently, selected from methyl, ethyl, n-propyl and n-butyl.

In some embodiments, R$^1$ is methyl and R$^2$ is n-propyl.

In some embodiments, R$^1$ and R$^2$ together with the N atom to which they are attached form a heterocycloalkyl group optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^a$, SR$^a$, C(═O)R$^b$, C(═O)NR$^c$R$^d$, C(═O)OR$^a$, C(═S)NR$^c$R$^d$, OC(═O)R$^b$, OC(═O)NR$^c$R$^d$, NR$^c$R$^d$, NR$^c$C(═O)R$^d$, NR$^c$C(═O)OR$^a$, NR$^c$S(═O)$_2$R$^b$, S(═O)R$^b$, S(═O)NR$^c$R$^d$, S(═O)$_2$OH, S(═O)$_2$R$^b$, and S(═O)$_2$NR$^c$R$^d$.

In some embodiments, R$^1$ and R$^2$ together with the N atom to which they are attached form azepanyl, piperazinyl, morpholino, piperidinyl, pyrrolidinyl, azetidinyl or aziridinyl, each optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^a$, SR$^a$, C(═O)R$^b$, C(═O)NR$^c$R$^d$, C(═O)OR$^a$, C(═S)NR$^c$R$^d$, OC(═O)R$^b$, OC(═O)NR$^c$R$^d$, NR$^c$R$^d$, NR$^c$C(═O)R$^d$, NR$^c$C(═O)OR$^a$, NR$^c$S(═O)$_2$R$^b$, S(═O)R$^b$ S(═O)NR$^c$R$^d$, S(═O)$_2$OH, S(═O)$_2$R$^b$, and S(═O)$_2$NR$^c$R$^d$.

In some embodiments, R$^3$ is C$_{1-6}$ alkyl optionally substituted by 1, 2, 3, 4 or 5 substituents independently selected from halo, CN, NO$_2$, C$_{1-6}$ haloalkyl, C$_{6-10}$ aryl, C$_{3-14}$ cycloalkyl, heterocyclyl, OR$^a$, SR$^a$, C(═O)R$^b$, C(═O)NR$^c$R$^d$, C(═O)OR$^a$, C(═S)NR$^c$R$^d$, OC(═O)R$^b$, OC(═O)NR$^c$R$^d$, NR$^c$R$^d$, NR$^c$C(═O)R$^b$, NR$^c$C(═O)OR$^a$, NR$^c$S(═O)$_2$R$^b$, S(═O)R$^b$ S(═O)NR$^c$R$^d$, S(═O)$_2$OH, S(═O)$_2$R$^b$, and S(═O)$_2$NR$^c$R$^d$.

In some embodiments, R$^3$ is C$_{1-6}$ alkyl optionally substituted by 1, 2 or 3 substituents independently selected from halo, CN, NO$_2$, C$_{1-6}$ haloalkyl, C$_{6-10}$ aryl, C$_{3-14}$ cycloalkyl, heterocyclyl, OR$^a$, SR$^a$, C(═O)R$^b$, C(═O)NR$^c$R$^d$, C(═O)OR$^a$, C(═S)NR$^c$R$^b$, OC(═O)R$^b$, OC(═O)NR$^c$R$^d$, NR$^c$R$^d$, NR$^c$C(═O)R$^b$, NR$^c$C(═O)OR$^a$, NR$^c$S(═O)$_2$R$^b$, S(═O)R$^b$, S(═O)NR$^c$R$^d$, S(═O)$_2$OH, S(═O)$_2$R$^b$, and S(═O)$_2$NR$^c$R$^d$.

In some embodiments, R$^3$ is C$_{1-6}$ alkyl optionally substituted by 1, 2 or 3 substituents independently selected from halo, OH, CN, NO$_2$, C$_{1-6}$ alkoxy and C$_{1-6}$ haloalkoxy.

In some embodiments, R$^3$ is C$_{1-6}$ alkyl optionally substituted by 1, 2 or 3 substituents independently selected from OH and C$_{1-4}$ alkoxy.

In some embodiments, R$^3$ is C$_{1-6}$ alkyl optionally substituted by 1 or 2 OH. In some further embodiments, R$^3$ is C$_{3-6}$ alkyl optionally substituted by OH. In yet further embodiments, R$^3$ is C$_{3-6}$ alkyl substituted by OH. In yet further embodiments, R$^3$ is —CH$_2$CH(CH$_3$)$_2$ or —CH$_2$C(CH$_3$)$_2$(OH). In yet further embodiments, R$^3$ is —CH$_2$C(CH$_3$)$_2$(OH).

In some embodiments, R$^4$ and R$^5$ are each, independently, selected from H, C$_{1-6}$ alkyl, C$_{6-10}$ aryl, heterocyclyl, —NR$^7$R$^8$, —OR$^9$, —C(═O)R$^9$, —C(═O)OR$^9$, and —C(═O)NR$^7$R$^8$, wherein each of the C$_{1-6}$ alkyl, C$_{6-10}$ aryl and heterocyclyl is optionally substituted by 1, 2, 3, 4 or 5 substituents independently selected from halo, CN, NO$_2$, C$_{1-6}$ alkyl, C$_{1-6}$ haloalkyl, C$_{6-10}$ aryl, C$_{3-14}$ cycloalkyl, heterocyclyl, OR$^a$, SR$^a$, C(=O)R$^b$, C(=O)NR$^c$R$^d$, C(=O)OR$^a$, C(=S)NR$^c$R$^d$OC(=O)R$^b$, OC(=O)NR$^c$R$^d$, NR$^c$R$^d$, NR$^c$C(=O)R$^b$, NR$^c$C(=O)OR$^a$, NR$^c$S(=O)$_2$R$^b$, S(=O)R$^b$, S(=O)NR$^c$R$^d$, S(=O)$_2$OH, S(=O)$_2$R$^b$, and S(=O)$_2$NR$^c$R$^d$.

In some embodiments:

R$^4$ and R$^5$ are each, independently, selected from H, C$_{1-6}$ alkyl, C$_{6-10}$ aryl, heterocyclyl, —NR$^7$R$^8$, —OR$^9$, —C(=O)R$^9$, —C(=O)OR$^9$, and —C(=O)NR$^7$R$^8$, wherein each of the C$_{1-6}$ alkyl, C$_{6-10}$ aryl and heterocyclyl is optionally substituted by 1, 2 or 3 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy;

R$^7$ and R$^8$ are each, independently, selected from H, C$_{1-6}$ alkyl, C$_{1-6}$ alkoxy, C$_{1-6}$ alkoxy-C$_{1-6}$ alkyl, C$_{6-10}$ aryl, C$_{6-10}$ aryl-C$_{1-6}$ alkyl, C$_{6-10}$ aryloxy-C$_{1-6}$ alkyl, wherein each of the C$_{1-6}$ alkyl, C$_{1-6}$ alkoxy, C$_{1-6}$ alkoxy-C$_{1-6}$ alkyl, C$_{6-10}$ aryl, C$_{6-10}$ aryl-C$_{1-6}$ alkyl and C$_{6-10}$ aryloxy-C$_{1-6}$ alkyl is optionally substituted by 1, 2, 3, 4 or 5 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy;

or R$^7$ and R$^8$ together with the N atom to which they are attached form a heterocyclyl group optionally substituted by 1, 2, 3, 4 or 5 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy; and each R$^9$ is independently H or C$_{1-6}$ alkyl optionally substituted by 1, 2, 3, 4 or 5 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy.

In some embodiments:

R$^4$ and R$^5$ are each, independently, selected from H, C$_{1-6}$ alkyl, C$_{6-10}$ aryl, heterocyclyl, —NR$^7$R$^8$, and —OR$^9$, wherein each of the C$_{1-6}$ alkyl, C$_{6-10}$ aryl and heterocyclyl is optionally substituted by 1, 2 or 3 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy;

R$^7$ and R$^8$ are each, independently, selected from H, C$_{1-6}$ alkyl, C$_{1-6}$ alkoxy, C$_{1-6}$ alkoxy-C$_{1-6}$ alkyl, C$_{6-10}$ aryl, C$_{6-10}$ aryl-C$_{1-6}$ alkyl, C$_{6-10}$ aryloxy-C$_{1-6}$ alkyl, wherein each of the C$_{1-6}$ alkyl, C$_{1-6}$ alkoxy, C$_{1-6}$ alkoxy-C$_{1-6}$ alkyl, C$_{6-10}$ aryl, C$_{6-10}$ aryl-C$_{1-6}$ alkyl and C$_{6-10}$ aryloxy-C$_{1-6}$ alkyl is optionally substituted by 1, 2, 3, 4 or 5 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy;

or R$^7$ and R$^8$ together with the N atom to which they are attached form a heterocyclyl group optionally substituted by 1, 2, 3, 4 or 5 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy; and R$^9$ is C$_{1-6}$ alkyl, C$_{1-6}$ alkoxy-C$_{1-6}$ alkyl, C$_{6-10}$ aryl, C$_{6-10}$ aryl-C$_{1-6}$ alkyl, or C$_{6-10}$ aryloxy-C$_{1-6}$ alkyl.

In some embodiments:

R$^4$ and R$^5$ are each, independently, selected from H, C$_{1-6}$ alkyl, C$_{6-10}$ aryl, —NR$^7$R$^8$, or —OR$^9$, wherein each of the C$_{1-6}$ alkyl and C$_{6-10}$ aryl is optionally substituted by 1, 2 or 3 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy;

R$^7$ and R$^8$ are each, independently, selected from H, C$_{1-6}$ alkyl, C$_{1-6}$ alkoxy, C$_{1-6}$ alkoxy-C$_{1-6}$ alkyl, C$_{6-10}$ aryl, C$_{6-10}$ aryl-C$_{1-6}$ alkyl, C$_{6-10}$ aryloxy-C$_{1-6}$ alkyl;

or R$^7$ and R$^8$ together with the N atom to which they are attached form a heterocyclyl group, wherein the heterocyclyl group is selected from azepanyl, morpholino, piperidinyl, pyrrolidinyl, azetidinyl, and aziridinyl; and R$^9$ is C$_{1-6}$ alkyl, C$_{1-6}$ alkoxy-C$_{1-6}$ alkyl, C$_{6-10}$ aryl, C$_{6-10}$ aryl-C$_{1-6}$ alkyl, or C$_{6-10}$ aryloxy-C$_{1-6}$ alkyl.

In some embodiments, R$^4$ and R$^5$ are each, independently, selected from H, C$_{6-10}$ aryl, azepanyl, morpholino, piperazinyl, piperidinyl, pyrrolidinyl, azetidinyl, aziridinyl, —NHR$^8$, and —OR$^9$; and R$^8$ and R$^9$ are each, independently, selected from C$_{1-6}$ alkyl, C$_{1-6}$ alkoxy-C$_{1-6}$ alkyl, C$_{6-10}$ aryl, C$_{6-10}$ aryl-C$_{1-6}$ alkyl and C$_{6-10}$ aryloxy-C$_{1-6}$ alkyl.

In some embodiments, R$^4$ and R$^5$ are each, independently, selected from H, C$_{6-10}$ aryl, azepanyl, piperidinyl, pyrrolidinyl, azetidinyl, aziridinyl, —NHR$^8$, and —OR$^9$; and R$^8$ and R$^9$ are each, independently, C$_{1-6}$ alkoxy-C$_{1-6}$ alkyl.

In some embodiments, R$^4$ and R$^5$ are each, independently, selected from H, C$_{6-10}$ aryl, azepanyl, piperidinyl, pyrrolidinyl, azetidinyl, aziridinyl, —NHR$^8$, or —OR$^9$; and R$^8$ and R$^9$ are each, independently, C$_{1-4}$ alkyl substituted by methoxy.

In some embodiments, one of R$^4$ and R$^5$ is H and the other is phenyl, piperidinyl, —NHCH$_2$CH$_2$—OCH$_3$ or —OCH$_2$CH$_2$—OCH$_3$.

In some embodiments, R$^4$ is H and R$^5$ is phenyl, piperidinyl, —NHCH$_2$CH$_2$—OCH$_3$ or —OCH$_2$CH$_2$—OCH$_3$.

In some embodiments, R$^4$ is phenyl, piperidinyl, —NHCH$_2$CH$_2$—OCH$_3$ or —OCH$_2$CH$_2$—OCH$_3$; and R$^5$ is H.

In some embodiments, R$^1$ and R$^2$ are each, independently, selected from methyl, ethyl, n-propyl and n-butyl; R$^3$ is C$_{3-6}$ alkyl optionally substituted by OH; R$^4$ and R$^5$ are each, independently, selected from H, C$_{6-10}$ aryl, azepanyl, piperazinyl, morpholino, piperidinyl, pyrrolidinyl, azetidinyl, aziridinyl, —NHR$^8$, and —OR$^9$; and R$^8$ and R$^9$ are each, independently, selected from C$_{1-6}$ alkyl, C$_{1-6}$ alkoxy-C$_{1-6}$ alkyl, C$_{6-10}$ aryl, C$_{6-10}$ aryl-C$_{1-6}$ alkyl and C$_{6-10}$ aryloxy-C$_{1-6}$ alkyl.

In some embodiments, R$^1$ is methyl; R$^2$ is n-propyl; R$^3$ is C$_{3-6}$ alkyl optionally substituted by OH; R$^4$ and R$^5$ are each, independently, selected from H, C$_{6-10}$ aryl, azepanyl, piperidinyl, pyrrolidinyl, azetidinyl, aziridinyl, —NHR$^8$, and —OR$^9$; and R$^8$ and R$^9$ are each, independently, C$_{1-6}$ alkoxy-C$_{1-6}$ alkyl.

In some embodiments, $R^1$ is methyl; $R^2$ is n-propyl; $R^3$ is $C_{3-6}$ alkyl optionally substituted by OH; one of $R^4$ and $R^5$ is H and the other is selected from $C_{6-10}$ aryl, azepanyl, piperidinyl, pyrrolidinyl, azetidinyl, aziridinyl, —NHR$^8$, and —OR$^9$; and $R^8$ and $R^9$ are each, independently, $C_{1-6}$ alkoxy-$C_{1-6}$ alkyl.

In some embodiments, $R^1$ is methyl; $R^2$ is n-propyl; $R^3$ is $C_{3-6}$ alkyl optionally substituted by OH; $R^4$ is H; $R^5$ is selected from $C_{6-10}$ aryl, azepanyl, piperidinyl, pyrrolidinyl, azetidinyl, aziridinyl, —NHR$^8$ and —OR$^9$; and $R^8$ and $R^9$ are each, independently, $C_{1-6}$ alkoxy-$C_{1-6}$ alkyl.

In some embodiments, $R^1$ is methyl; $R^2$ is n-propyl; $R^3$ is $C_{3-6}$ alkyl optionally substituted by OH; $R^4$ is selected from $C_{6-10}$ aryl, azepanyl, piperidinyl, pyrrolidinyl, azetidinyl, aziridinyl,
—NHR$^8$ and —OR$^9$; $R^5$ is H; and $R^8$ and $R^9$ are each, independently, $C_{1-6}$ alkoxy-$C_{1-6}$ alkyl.

In some embodiments, $R^1$ is methyl; $R^2$ is n-propyl; $R^3$ is —CH$_2$CH(CH$_3$)$_2$ or —CH$_2$C(CH$_3$)$_2$(OH); one of $R^4$ and $R^5$ is H and the other is selected from phenyl, piperidinyl,
—NHCH$_2$CH$_2$—OCH$_3$ and —OCH$_2$CH$_2$—OCH$_3$.

In some embodiments, the compound of the invention has the structure:

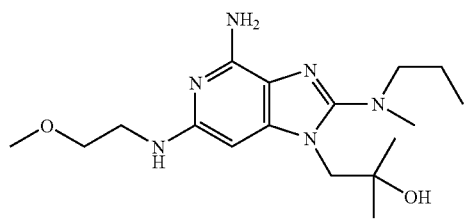

or is a pharmaceutically acceptable salt thereof, a tautomer thereof, or a pharmaceutically acceptable salt of the tautomer.

In some embodiments, the compound of the invention has the structure:

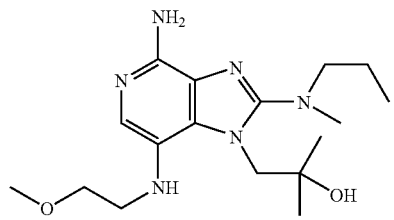

or is a pharmaceutically acceptable salt thereof, a tautomer thereof, or a pharmaceutically acceptable salt of the tautomer.

In some embodiments, the compound of the invention has the structure:

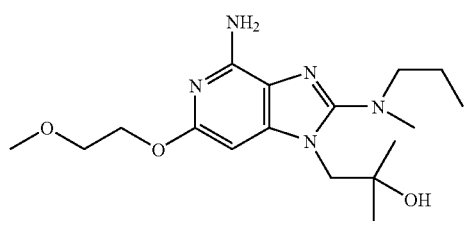

or is a pharmaceutically acceptable salt thereof, a tautomer thereof, or a pharmaceutically acceptable salt of the tautomer.

In some embodiments, the compound of the invention has the structure:

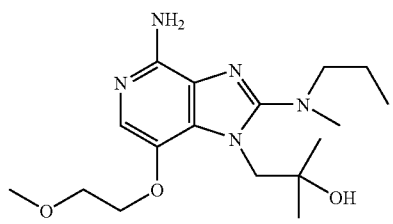

or is a pharmaceutically acceptable salt thereof, a tautomer thereof, or a pharmaceutically acceptable salt of the tautomer.

In some embodiments, the compound of the invention has the structure:

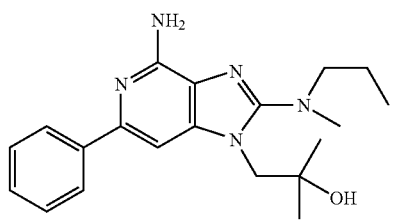

or is a pharmaceutically acceptable salt thereof, a tautomer thereof, or a pharmaceutically acceptable salt of the tautomer.

In some embodiments, the compound of the invention has the structure:

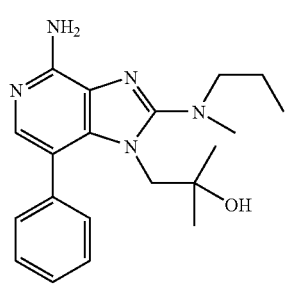

or is a pharmaceutically acceptable salt thereof, a tautomer thereof, or a pharmaceutically acceptable salt of the tautomer.

In some embodiments, the compound of the invention has the structure:

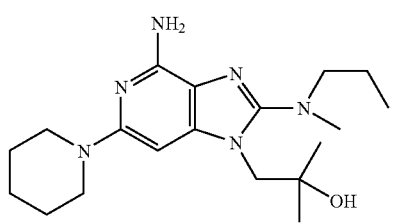

or is a pharmaceutically acceptable salt thereof, a tautomer thereof, or a pharmaceutically acceptable salt of the tautomer.

In some embodiments, the compound of the invention has the structure:

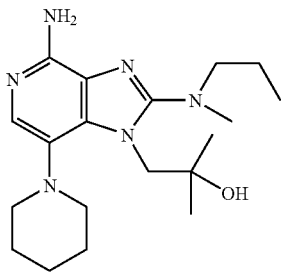

or is a pharmaceutically acceptable salt thereof, a tautomer thereof, or a pharmaceutically acceptable salt of the tautomer.

In some embodiments, $R^4$ and $R^5$ together with the two carbon atoms to which they are attached form a 5-7 membered cycloalkyl, a 5-7 membered heterocycloalkyl, or a 5-7 membered heteroaryl group, each optionally substituted by 1, 2, 3, 4 or 5 $R^{12}$.

In some embodiments, $R^4$ and $R^5$ together with the two carbon atoms to which they are attached form a 5-7 membered cycloalkyl group optionally substituted by 1, 2, 3, 4 or 5 $R^{12}$.

In some embodiments, $R^4$ and $R^5$ together with the two carbon atoms to which they are attached form a 5-7 membered heterocycloalkyl group optionally substituted by 1, 2, 3, 4 or 5 $R^{12}$.

In some embodiments, $R^4$ and $R^5$ together with the two carbon atoms to which they are attached form a 5-7 membered heteroaryl group optionally substituted by 1, 2, 3, 4 or 5

In some embodiments, $R^4$ and $R^5$ together with the two carbon atoms to which they are attached form a 5-6 membered heteroaryl group optionally substituted by 1, 2 or 3 $R^{12}$.

In some embodiments, $R^4$ and $R^5$ together with the two carbon atoms to which they are attached form a 5-6 membered heteroaryl group optionally substituted by 1 or 2 $R^{12}$.

In some embodiments, $R^4$ and $R^5$ together with the two carbon atoms to which they are attached form a 5-6 membered heteroaryl group.

In some embodiments:
each $R^{12}$ is independently $C_{1-6}$ alkyl, $C_{6-10}$ aryl, heterocyclyl, —$NR^7R^8$, —$OR^9$, —$C(=O)R^9$, —$C(=O)OR^9$, or —$C(=O)NR^7R^8$, wherein each of the $C_{1-6}$ alkyl, $C_{6-10}$ aryl and heterocyclyl is optionally substituted by 1, 2 or 3 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy;

$R^7$ and $R^8$ are each, independently, selected from H, $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl, $C_{6-10}$ aryloxy-$C_{1-6}$ alkyl, wherein each of the $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl and $C_{6-10}$ aryloxy-$C_{1-6}$ alkyl is optionally substituted by 1, 2, 3, 4 or 5 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy;

or $R^7$ and $R^8$ together with the N atom to which they are attached form a heterocyclyl group optionally substituted by 1, 2, 3, 4 or 5 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy; and each $R^9$ is independently H or $C_{1-6}$ alkyl optionally substituted by 1, 2, 3, 4 or 5 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy.

In some embodiments:
each $R^{12}$ is independently $C_{1-6}$ alkyl, $C_{6-10}$ aryl, heterocyclyl, —$NR^7R^8$, or —$OR^9$, wherein each of the $C_{1-6}$ alkyl, $C_{6-10}$ aryl and heterocyclyl is optionally substituted by 1, 2 or 3 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy;

$R^7$ and $R^8$ are each, independently, selected from H, $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl, $C_{6-10}$ aryloxy-$C_{1-6}$ alkyl, wherein each of the $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl and $C_{6-10}$ aryloxy-$C_{1-6}$ alkyl is optionally substituted by 1, 2, 3, 4 or 5 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy;

or $R^7$ and $R^8$ together with the N atom to which they are attached form a heterocyclyl group optionally substituted by 1, 2, 3, 4 or 5 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy; and $R^9$ is H or $C_{1-6}$ alkyl optionally substituted by 1, 2, 3, 4 or 5 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy.

In some embodiments:
each $R^{12}$ is independently $C_{1-6}$ alkyl, $C_{6-10}$ aryl, —$NR^7R^8$, or —$OR^9$, wherein each of the $C_{1-6}$ alkyl and $C_{6-10}$ aryl is optionally substituted by 1, 2 or 3 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy;

$R^7$ and $R^8$ are each, independently, selected from H, $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl, $C_{6-10}$ aryloxy-$C_{1-6}$ alkyl;

or $R^7$ and $R^8$ together with the N atom to which they are attached form a heterocyclyl group optionally substituted by 1, 2, 3, 4 or 5 substituents independently selected from halo, OH, CN, $NO_2$, $C_{1-6}$ alkyl, $C_{1-6}$ haloalkyl, $C_{6-10}$ aryloxy, $C_{1-6}$ alkoxy and $C_{1-6}$ haloalkoxy; and $R^9$ is $C_{1-6}$ alkyl, $C_{1-6}$ alkoxy-$C_{1-6}$ alkyl, $C_{6-10}$ aryl, $C_{6-10}$ aryl-$C_{1-6}$ alkyl, or $C_{6-10}$ aryloxy-$C_{1-6}$ alkyl.

In some embodiments:
each $R^{12}$ is independently $C_{1-6}$ alkyl, $C_{6-10}$ aryl, —$NR^7R^8$, or —$OR^9$, wherein each of the $C_{1-6}$ alkyl and $C_{6-10}$ aryl is optionally substituted by 1, 2 or 3 substituents independently selected from halo, OH, CN, $NO_2$, $C_{1-6}$ alkyl, $C_{1-6}$ haloalkyl, $C_{6-10}$ aryl, $C_{3-14}$ cycloalkyl, heterocyclyl, $C_{6-10}$ aryloxy, $C_{1-6}$ alkoxy and $C_{1-6}$ haloalkoxy;

$R^7$ and $R^8$ are each, independently, selected from H, $C_{1-6}$ alkyl, $C_{1-6}$ alkoxy, $C_{1-6}$ alkoxy-$C_{1-6}$ alkyl, $C_{6-10}$ aryl, $C_{6-10}$ aryl-$C_{1-6}$ alkyl, $C_{6-10}$ aryloxy-$C_{1-6}$ alkyl;

or $R^7$ and $R^8$ together with the N atom to which they are attached form a heterocyclyl group, wherein the heterocyclyl group is selected from azepanyl, morpholino, piperidinyl, pyrrolidinyl, azetidinyl, and aziridinyl; and $R^9$ is $C_{1-6}$ alkyl, $C_{1-6}$ alkoxy-$C_{1-6}$ alkyl, $C_{6-10}$ aryl, $C_{6-10}$ aryl-$C_{1-6}$ alkyl, or $C_{6-10}$ aryloxy-$C_{1-6}$ alkyl.

In some embodiments:

each $R^{12}$ is independently $C_{6-10}$ aryl, azepanyl, morpholino, piperazinyl, piperidinyl, pyrrolidinyl, azetidinyl, aziridinyl, —$NHR^8$, or —$OR^9$; and $R^8$ and $R^9$ are each, independently, selected from $C_{1-6}$ alkyl, $C_{1-6}$ alkoxy-$C_{1-6}$ alkyl, $C_{6-10}$ aryl, $C_{6-10}$ aryl-$C_{1-6}$ alkyl and $C_{6-10}$ aryloxy-$C_{1-6}$ alkyl.

54. The compound of claim 1 wherein:

each $R^{12}$ is independently $C_{6-10}$ aryl, azepanyl, piperidinyl, pyrrolidinyl, azetidinyl, aziridinyl, —$NHR^8$, or —$OR^9$;

$R^8$ and $R^9$ are each, independently, $C_{1-4}$ alkyl substituted by methoxy.

In some embodiments, each $R^{12}$ is independently phenyl, piperidinyl, azepanyl, piperidinyl, pyrrolidinyl, azetidinyl, aziridinyl, —$NHCH_2CH_2$—$OCH_3$ or —$OCH_2CH_2$—$OCH_3$.

In some further embodiments, each $R^{12}$ is independently phenyl, piperidinyl, —$NHCH_2CH_2$—$OCH_3$ or —$OCH_2CH_2$—$OCH_3$.

In some embodiments, a compounds of present invention has Formula (II):

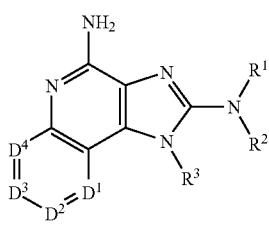

(II)

or is a pharmaceutically acceptable salt thereof, a tautomer thereof, or a pharmaceutically acceptable salt of the tautomer, wherein one of $D^1$, $D^2$, $D^3$ and $D^4$ is N and the others are each independently $CR^{13}$; and each $R^{13}$ is independently selected from H and $R^{12}$.

In some embodiments of the compounds of Formula (II), $D^1$ is N.

In some embodiments of the compounds of Formula (II), $D^2$ is N.

In some embodiments of the compounds of Formula (II), $D^3$ is N.

In some embodiments of the compounds of Formula (II), $D^4$ is N.

In some embodiments of the compounds of Formula (II), at least one $R^{13}$ is H.

In some embodiments of the compounds of Formula (II), at least two $R^{13}$ are H.

In some embodiments of the compounds of Formula (II), all three $R^{13}$ are H.

In some embodiments of the compounds of Formula (II), $R^1$ and $R^2$ are each, independently, selected from methyl, ethyl, n-propyl and n-butyl; $R^3$ is $C_{3-6}$ alkyl optionally substituted by OH; each $R^{12}$ is independently $C_{6-10}$ aryl, azepanyl, piperidinyl, piperazinyl, pyrrolidinyl, azetidinyl, aziridinyl, —$NHR^8$, or —$OR^9$; and $R^8$ and $R^9$ are each, independently, $C_{1-6}$ alkoxy-$C_{1-6}$ alkyl.

In some embodiments of the compounds of Formula (II), $R^1$ is methyl; $R^2$ is n-propyl; $R^3$ is $C_{3-6}$ alkyl optionally substituted by OH; each $R^{12}$ is independently $C_{6-10}$ aryl, azepanyl, piperidinyl, pyrrolidinyl, azetidinyl, aziridinyl, —$NHR^8$, or —$OR^9$; and $R^8$ and $R^9$ are each, independently, $C_{1-6}$ alkoxy-$C_{1-6}$ alkyl.

In some embodiments, the compound of the invention has the structure:

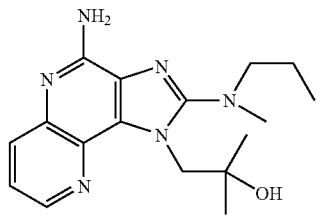

or is a pharmaceutically acceptable salt thereof, a tautomer thereof, or a pharmaceutically acceptable salt of the tautomer.

In some embodiments, the compound of the invention has the structure:

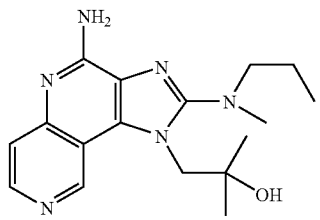

or is a pharmaceutically acceptable salt thereof, a tautomer thereof, or a pharmaceutically acceptable salt of the tautomer.

In some embodiments, the compound of the invention has the structure:

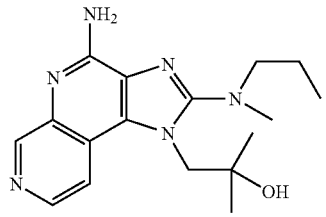

or is a pharmaceutically acceptable salt thereof, a tautomer thereof, or a pharmaceutically acceptable salt of the tautomer.

In some embodiments, the compound of the invention has the structure:

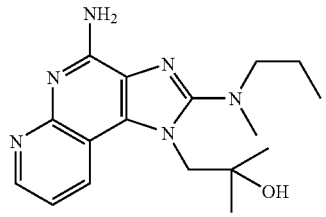

or a pharmaceutically acceptable salt thereof, a tautomer thereof, or a pharmaceutically acceptable salt of the tautomer.

Further provided are compounds of Formula (I) or (II) and mixtures thereof where any asymmetric carbon atom(s) can have either the R or S configuration. Substituents at a double bond or a ring of the compounds of Formula (I) or (II) may be present in either the cis (—Z—) or trans (-E-) configurations.

The compounds may thus be present as mixtures of isomers, diastereomers, and enantiomers or may be present as pure isomers. In some embodiments, the compounds are enantiomerically pure where only one enantiomer is present. In other embodiments, the compound may be present as a mixture of enantiomers which includes more of one enantiomer than it does of the other.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

Generally, a compound of the invention, or a composition comprising such a compound, is considered effective to elicit an immune response at a concentration of 300 μM or less in some embodiments, 200 μM or less in some embodiments, 100 μM or less in some embodiments, or 20 μM or less in some embodiments if the compound of the invention effects (a) the production of TNF-α in an in vitro cell based assay of human peripheral blood mononuclear cells, and (b) a concentration of human peripheral blood mononuclear cells (PBMCS) of about 500,000/mL, when the cells are exposed to the compound for a period of about 18-24 hours, preferably about 24 hours.

The above method of stimulating a local immune response, for example in selected cells or tissues of a patient, includes the stimulation of a local immune response where the selected cells or tissues are infected or cancerous. In some embodiments, the selected cells or tissues are infected with a fungus or bacterium. In some embodiments, the selected tissues are inflamed with an allergen, for example in an asthmatic condition. In other embodiments, the selected cells are infected with a virus, bacteria, fungus or parasite.

Another embodiment provides a method of inducing interferon biosynthesis in a subject. Such methods include administering a compound of Formula (I) or (II) to the subject in an amount sufficient to induce interferon biosynthesis. In some such methods, a vaccine adjuvant of Formula (I) or (II) is administered to the subject in an amount sufficient to induce interferon biosynthesis.

Another embodiment provides a compound of Formula (I) or (II), wherein the compound is co-administered with another agent to a patient in need thereof. In some such embodiments, the agent is an antigen or a vaccine. In embodiments, where the compound of Formula (I) is co-administered to a patient or subject along with another agent, the compound of Formula (I) may be administered to the subject before, during, or after the other agent is administered to the subject. Therefore, in some embodiments, the compound of Formula (I) or (II) is administered to the subject at the same time that the other agent is administered to the subject. The location or site of administration of the compound of Formula (I) or (II) can be the same or different as the location of an antigen when the compound is used with an antigen.

Another embodiment provides a method of modulating an immune response in a subject. Such methods include administering a compound of Formula (I) or (II) to the subject.

Another embodiment provides a method for inducing the production of TNF-α in a subject. Such methods include administering a compound of Formula (I) or (II) to a subject in an amount sufficient to induce the production of TNF-α. In some such embodiment thereof, the compound has an average steady state drug concentration in the blood of less than 20 μM.

Another embodiment provides a method of inducing an immune response in a subject. The embodiment includes administering a compound of Formula (I) or (II) to the subject in an amount sufficient to induce an immune response. In some such embodiments, the immune response involves the production of cytokines or increased production of TNF-α. In some embodiments, the induction of an immune response includes the production of antibodies that may be neutralizing antibodies or antibodies that mediate Antibody Dependent Cell Mediated Cytotoxicity (ADCC antibodies).

Another embodiment provides a method of inducing an immune response in a subject suffering from a microbial (viral, bacterial, fungal or parasitic) infection. The method includes administering a compound of Formula (I) or (TI) to the subject in an amount sufficient to induce an immune response.

Another embodiment provides a method of inducing an immune response in a subject suffering from a viral infection or a disease condition caused by a virus. The method includes administering a compound of Formula (I) or (II) to the subject in an amount sufficient to induce an immune response in the subject. The virus may be selected from one or more of the viral pathogens described in the antigen section below. In some such embodiments, the subject is suffering from a viral infection or disease condition caused by the hepatitis C virus (HCV). In other embodiments, the subject is suffering from a viral infection or disease condition caused by the human immunodeficiency virus (HIV).

Another embodiment provides a method of inducing an immune response in a subject for prevention of a viral infection or a disease condition caused by a virus. The method includes administering a compound of Formula (I) or (II) to the subject in an amount sufficient to induce an immune response in the subject. In some such embodiments, the subject is prevented from a viral infection or disease condition. In other embodiments, the subject is protected from a microbial or other pathogenic infection, such as those described herein.

Another embodiment provides a method of inducing an immune response in a subject suffering from an abnormal cellular proliferation or cancer. The method includes administering a compound of Formula (I) or (II) to the subject in an amount sufficient to induce an immune response. In some embodiments, the compound is administered to a subject that is suffering from a disease associated with abnormal cellular proliferation. In some such embodiments, the disease is selected from neuro-fibromatosis, atherosclerosis, pulmonary fibrosis, arthritis, psoriasis, glomerulonephritis, restenosis, proliferative diabetic retinopathy (PDR), hypertrophic scar formation, inflammatory bowel disease, transplantation rejection, angiogenesis, or endotoxic shock.

Other embodiments provide methods of inducing an immune response in a subject suffering from an allergic disease. Such methods include administering a compound of Formula (I) or (TI) to the subject in an amount sufficient to induce an immune response.

Another embodiment provides a method of inducing an immune response in a subject suffering from asthma. The method includes administering a compound of Formula (I) or (II) to the subject in an amount sufficient to induce an immune response. In some embodiments, asthma may be treated by steering the immune response away from Type 2 cytokine secretion and effector mechanism (e.g., IgE production and/or mast cell/basophil activation).

Another embodiment provides a method of inducing an immune response in a subject suffering from precancerous lesions. The method includes administering a compound of Formula (I) or (II) to the subject in an amount sufficient to induce an immune response. In some such embodiments, the precancerous lesions are actinic keratosis. In other embodiments, the precancerous lesions are selected from actinic keratosis, atypical or dysplastic nevi, or premalignant lentigos. In another embodiment or method, the compound of Formula (I) or (II) is administered topically to a subject.

Other embodiments provide a method of inhibiting a kinase in a subject. Such methods include administering the compound of Formula (I) or (II) to the subject.

Another embodiment provides a method of modulating an immune response in a subject. The method includes administering a compound of Formula (I) or (II) to the subject in an amount sufficient to inhibit a kinase in the subject. In some such embodiments, the kinase is selected from EGFr, c-Kit, bFGF, Kdr, CHK1, CDK, cdc-2, Akt, PDGF, PI3K, VEGF, PKA, PKB, src, c-Met, Abl, Ras, RAF, MEK, or combinations thereof. In another embodiment or method, the compound of Formula (I) is administered topically to a subject.

Another embodiment provides a method of inducing an immune response in a subject, comprising: administering to the subject a compound of Formula (I) or (II) and an antigen, wherein the compound induces or enhances an immune response to the antigen in the subject. More particularly the antigen can be one or more viral, bacterial, fungal, parasitic or tumor antigens or other antigens as described herein.

Another embodiment provides a composition comprising: the compound of Formula (I) or (II) and another agent. In some embodiments, the other agent is an antigen. In further embodiments, the composition of the invention comprises the compound of Formula (I) or (II) with an antigen and a second adjuvant. In another embodiment, the composition of the invention provides a compound of Formula (I) or (TI) and a second adjuvant. In another embodiment, the composition further comprises poly(lactide-co-glycolide) (PLG). In another embodiment, the composition further comprises MF59 or another adjuvant.

Additional embodiments, methods and compositions contemplated to be useful in the instant invention are disclosed in PCT/US2005/032721, PCT/US2005/022769, PCT/US2005/022520 and U.S. Ser. No. 10/814,480, 10/762,873, 60/582,654, 10/405,495, and 10/748,071 which are each hereby incorporated by reference in their entireties and for all purposes as if set forth fully herein.

Another embodiment provides a pharmaceutical composition, comprising: the compound of Formula (I) or (TI) and a pharmaceutically acceptable excipient.

Another embodiment of the present invention provides a method of stimulating TLR-7 production comprising administering a compound of Formula (I) or (II). Another embodiment provides a method of stimulating TLR-8 production comprising administering a compound of Formula (I). Another embodiment provides a method of stimulating TLR-7 and TLR-8 production comprising administering a compound of Formula (I) or (II).

Compounds of the present invention may cause immune potentiation and stimulate production of TLR-7 and TLR-8. Such compounds can be used as polyclonal activators for the production of antigens. More particularly the invention relates to a method of preparing monoclonal antibodies with a desired antigen specificity comprising contacting the compounds of the present invention (such as those of Formula (I) or (II)) with immortalized memory B cells.

The monoclonal antibodies produced there from, or fragments thereof may be used for the treatment of disease, for the prevention of disease or for the diagnosis of disease. Methods of diagnosis may include contacting an antibody or an antibody fragment with a sample. The methods of diagnosis may also include the detection of an antigen/antibody complex.

The memory B cells to be transformed can come from various sources (e.g. from whole blood, from peripheral blood mononuclear cells (PBMCs), from blood culture, from bone marrow, from organs, etc.), and suitable methods for obtaining human B cells are well known in the art. Samples may include cells that are not memory B cells or other blood cells. A specific human memory B lymphocyte subpopulation exhibiting a desired antigen specificity may be selected before the transformation step by using methods known in the art. In one embodiment, the human memory B lymphocyte subpopulation has specificity for a virus e.g. the B cells are taken from a patient who is suffering or has recovered from the virus. In another embodiment, B cells are taken from subjects with Alzheimer's disease and include B cells with specificity for B-amyloid (e.g. Mattson & Chan (2003) Science 301:1 847-9; etc.).

Another embodiment provides a method for producing immortalized B memory lymphocytes, comprising the step of transforming B memory lymphocytes using the Epstein Barr virus in the presence of a compound of the present invention, such as a compound of Formula (I) or (II). See WO 04/76677.

The invention also provides pharmaceutical compositions that include any of the aforementioned compounds or embodiments of Formula (I) or (II). Such compositions may include other pharmaceutically acceptable ingredients such as one or more of excipients, carriers, and the like well-known to those skilled in the art.

It is contemplated that the invention encompasses all possible combinations of the preceding embodiments. In some embodiments of each of the compounds of Formula (I) or (II), and methods described herein, $R^1$ is methyl and $R^2$ is n-propyl.

The imidazopyridine compounds or derivatives thereof can be used with or without an antigen in therapeutic applications, for example to treat cancer or infectious diseases. The imidazopyridine compounds or derivatives thereof may also be used in combination with other therapeutic agents, such as anti-viral agents and monoclonal antibodies in different therapeutic applications.

One embodiment of the method of inducing an immunostimulatory effect in a patient is directed to administering an immunogenic composition comprising an antigen in an amount effective to stimulate an immune response such as a cell-mediated immune response and, as a vaccine adjuvant, an Imidazopyridine compound, in an amount effective to potentiate the immune response such as the cell-mediated immune response to the antigen.

Agents combined with the Imidazopyridine compounds or derivatives thereof, contemplated to be useful in treating the aforementioned diseases include those well known in the art, such as, but not limited to, anesthetics, hypnotic sedatives, anti-anxieties, antiepileptics, antipyretic antiphlogistics, stimulants, wake amines, anti-parkinson drugs, agents for psychoneuroses, agents for central nervous system, skeletal muscle relaxants, agents for autonomic nervous system, antispastic agents, cytotoxic agents, monoclonal antibodies, drugs for eye, drugs for nose and ear, anti-vertiginous drugs, cardiotonics, antiarrhythmic drugs, diuretics, pressure reduction drugs, vasoconstrictors, coronary vaso-dilators, peripheral vasodilating drugs, hyper-lipemia drugs, breath stimulants, antitussive and expectorant drugs, bronchodilators, drugs for allergy, antidiarrheal drugs, drugs for intestinal disorders, peptic ulcer drugs, stomachic digestants, antacids, cholagogouses, pituitary hormone drugs, salivary gland hormones, thyroid hormone drugs, antithyroid drugs, anabolic steroids, corticosteroids, androgen drugs, estrogen drugs, corpus luteum hormone drugs, mixed hormones, urinary/genital organ drugs, anus drugs, surgical sterilizations/antiseptics, wound protectives, externals for purulent diseases, analgesics, antipruritics, astringents, antiphlogistics, externals for parasite skin diseases, skin-softening drugs, caustics, dental/oral drugs, vitamins, inorganic preparations, supplemental liquids, hemostatics, anticoagulation drugs, drugs for liver diseases, antidotes, habitual intoxication drugs, drugs for treatment of gout, enzyme preparations, diabetic drugs, antioncotics, antihistaminics, antibiotics (such as ketolides, aminoglycosides, sulphonamides, and/or beta lactams), chemotherapeutics, biological preparations, anthelmintics, anti-Protozoas, drugs for preparations, X-ray contrast media, and diagnostic drugs.

Further methods of the invention are provided wherein compositions described herein are used for the treatment of cancer and reduction of tumor growth. In one aspect, an imidazopyridine compound of the invention is combined with a known mAb for the treatment of cancer. In one such embodiment, an antibody and an imidazopyridine compound are administered to a subject in need thereof. In some such embodiments, the antibody, individually, has an inhibiting effect upon tumor cell growth, and the imidazopyridine compound induces the production of cytokines.

In accordance with another embodiment of the present invention, a therapeutic composition for inhibiting tumor cell growth in a subject is provided. Such compositions include an effective amount of a combination of at least one imidazopyridine compound of the invention, at least one mAb, and at least one pharmaceutically acceptable carrier. In such embodiments, the combination may be more effective at inhibiting the growth of certain mammalian tumor cells than are any of the agents when individually administered.

In another embodiment, methods of treating cancer are provided in which known anticancer agents are combined with imidazopyridine compounds or derivatives thereof of the invention to reduce tumor growth in a subject. A number of suitable anticancer agents are contemplated for use in such methods. Indeed, the present invention contemplates, but is not limited to, administration of numerous anticancer agents including, but not limited to: fenretinide, vatalanib, SU-11248, SU 5416, SU 6668, oxaliplatin, bortezomib, R 115777, CEP-701, ZD-6474, MLN-518, lapatinib, gefitinib (iressa), erlotinib (tarceva), perifosine, CYC-202, LY-317615, squalamine, UCN-01, midostaurin, irofulven, staurosporine, alvocidib, genistein, DA-9601, avicine, docetaxel, IM 862, SU 101, and tetrathiomolybdate as well as other agents that induce apoptosis, such as, but not limited to polynucleotides (e.g., ribozymes); polypeptides (e.g., enzymes); drugs; biological mimetics; 25 alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons [e.g., IFN-a, etc.] and interleukins [e.g., IL-2, etc.], etc.); adoptive immunotherapy agents; hematopoietic growth factors; agents that induce tumor cell differentiation (e.g., all-trans-retinoic acid, etc.); gene 30 therapy reagents; antisense therapy reagents and nucleotides; tumor vaccines; and inhibitors of angiogenesis, and the like. Numerous other examples of chemotherapeutic compounds and anticancer therapies suitable for co-administration with the disclosed Imidazopyridine compounds or derivatives thereof will be known and apparent to those skilled in the art.

In some embodiments, anticancer agents comprise agents that induce or stimulate apoptosis. Agents that induce apoptosis include, but are not limited to, radiation (e.g., W); kinase inhibitors (e.g., Epidermal Growth Factor Receptor [EGFR] kinase; inhibitor, Vascular Growth Factor Receptor [VGFR] kinase inhibitor, Fibroblast Growth 5 Factor Receptor [FGFR] kinase inhibitor, Platelet-derived Growth Factor Receptor [PGFR] I kinase inhibitor, EGFr and Bcr-Abl kinase inhibitors such as Gleevec, Iressa, and Tarceva]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal Anti-inflammatory drugs I (NSAIDs)]; and cancer chemotherapeutic drugs [e.g., CPT-11, fludarabine (Fludara), dacarbazine (DTIC), dexamethasone, mitoxantrone, Mylotarg, cisplatinum, 5-FU, Doxrubicin, Taxotere or taxol]; cellular signaling molecules; ceramides and cytokines; and the like may also be administered to subjects in conjunction with the Imidazopyridines of Formula (I) or (II).

In other embodiments, methods of treating allergies are provided. Such methods include administering an imidazopyridine compound alone or in combination with another agent known to be effective against allergies. In such embodiments, the combination is more effective in treating an allergic condition than the known agent(s) is/are without the addition of the imidazopyridine compound. In some such embodiments, the known agent is an antihistamine and/or a leukotriene inhibitor. In other embodiments, the allergic condition is asthma. In other embodiments, the allergic condition is selected from allergic rhinitis, dermatosis, or urticaria. In some such embodiments, the combination is administered to the subject enterally, parenterally, intranasally, subcutaneously, or intraarterially.

Compositions contemplated to be within the scope of the present invention may include (an) additional adjuvant(s) and or other immune stimulator compound.

Adjuvants

Vaccines or immunogenic compositions of the invention may be administered in conjunction with other immunoregulatory agents. In particular, compositions can include an adjuvant. Adjuvants for use with the invention include, but are not limited to, one or more of the following set forth below:

Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt (s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

In one embodiment the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2$/g. Alternatively, aluminum phosphate adjuvant ($AlPO_4$) or aluminum hydroxyphosphate, which contains phosphate groups in place of some or all of the hydroxy groups of aluminum hydroxide adjuvant is provided. Preferred aluminum phosphate adjuvants provided herein are amorphous and soluble in acidic, basic and neutral media.

In another embodiment the adjuvant of the invention comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

Oil-Emulsions

Oil-emulsion compositions suitable for use as adjuvants in the invention include squalene-water emulsions, such as MF59 (5% Squalene, 0.5% Tween 80, and 0.5% Span 85, formulated into submicron particles using a microfluidizer). See WO90/14837. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325. Complete Freund's adjuvant (CFA) and incomplete Freund's adjuvant (IFA) may also be used as adjuvants in the invention.

Specific oil-in-water emulsion adjuvants useful with the invention include, but are not limited to:

(1) A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [WO90/14837.-Podda & Del Giudice (2003) *Expert Rev Vaccines* 2:197-203. Podda (2001) *Vaccine* 19: 2673-2680.], as described in more detail in Chapter 10 of ref. *Vaccine Design: The Subunit and Adjuvant Approach* (eds. Powell & Newman) Plenum Press 1995 (ISBN 0-306-44867-X). and chapter 12 of ref. Vaccine *Adjuvants: Preparation Methods and Research Protocols* (Volume 42 of *Methods in Molecular Medicine* series). ISBN: 1-59259-083-7. Ed. O'Hagan. The MF59 emulsion advantageously includes citrate ions e.g. 10 mM sodium citrate buffer.

(2) An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably $\leq 1$ as this provides a more stable emulsion. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

(3) An emulsion of squalene, a tocopherol, and a Triton detergent (e.g. Triton X-100).

(4) An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [Allison & Byars (1992) Res Immunol 143:519-25] (0.05-1% Thr-MDP, 5% squalane, 2.5% Pluronic L121 and 0.2% polysorbate 80). It can also be used without the Thr-MDP, as in the "AF" adjuvant [Hariharan et al. (1995) Cancer Res 55:3486-9] (5% squalane, 1.25% Pluronic L121 and 0.2% polysorbate 80). Microfluidisation is preferred.

The emulsions are preferably mixed with additional agents (such as an antigen) extemporaneously, at the time of delivery. Thus the adjuvant and antigen are typically kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group [Han et al (2005) Impact of Vitamin E on Immune Function and Infectious Diseases in the Aged at Nutrition, Immune functions and Health EuroConference, Paris, 9-10 Jun. 2005]. They also have antioxidant properties that may help to stabilize the emulsions [U.S. Pat. No. 6,630,161]. A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds Saponin Formulations Saponin formulations, may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 L1 Healthy Volunteers Immunized with Recombinant HPV-16 L1 Virus-Like Particles", Journal of Infectious Diseases (2003) 188:327-338; and Gerber et al., "Human Papillomavrisu Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) Vaccine 20 Suppl 5:B17-23} and the INFLUVAC PLUS™ product.

Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689

454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

3dMPL has been prepared from a heptoseless mutant of *Salmonella minnesota*. It activates cells of the monocyte/macrophage lineage and stimulates release of several cytokines, including IL-1, IL-12, TNF-α and GM-CSF (see also ref. Thompson et al. (2005) *J Leukoc Biol* 78: 'The low-toxicity versions of LPS, MPL® adjuvant and RC529, are efficient adjuvants for CD4+ T cells'.). Preparation of 3dMPL was originally described in reference UK patent application GB-A-2220211.

3dMPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position. The group attached to carbon 2 has Formula —NH—CO—CH$_2$—CR$^1$R$^{1'}$. The group attached to carbon 2' has Formula —NH—CO—CH$_2$—CR$^2$R$^{2'}$. The group attached to carbon 3' has Formula —O—CO—CH$_2$—CR$^3$R$^{3'}$. A representative structure is:

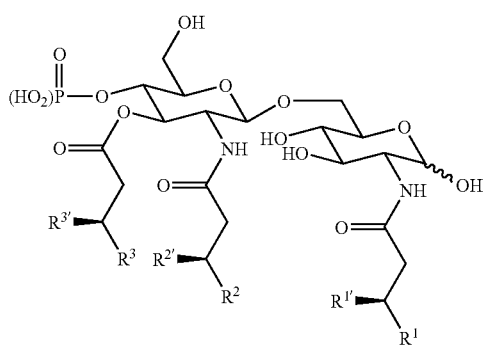

Groups R$^1$, R$^2$ and R$^3$ are each independently —(CH$_2$)$_n$—CH$_3$. The value of n is preferably between 8 and 16, more preferably between 9 and 12, and is most preferably 10. Groups R$^{1'}$, R$^{2'}$ and R$^{3'}$ can each independently be: (a) —H; (b) hydroxy; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, m is preferably 10. At the 3' position, m is preferably 12. Groups R$^{11}$, R$^2$ and R$^{3'}$ are thus preferably —O-acyl groups from dodecanoic acid, tetradecanoic acid or hexadecanoic acid.

When all of R$^{1'}$, R$^{2'}$ and R$^{3'}$ are —H then the 3dMPL has only 3 acyl chains (one on each of positions 2, 2' and 3'). When only two of R$^{1'}$, R$^{2'}$ and R$^{3'}$ are —H then the 3dMPL can have 4 acyl chains. When only one of R$^{1'}$, R$^{2'}$ and R$^{3'}$ is —H then the 3dMPL can have 5 acyl chains. When none of R$^{1'}$, R$^{2'}$ and R$^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g. ≧20%, ≧30%, ≧40%, ≧50% or more. 3dMPL with 6 acyl chains has been found to be the most adjuvant-active form.

Thus the most preferred form of 3dMPL for inclusion in compositions of the invention is:

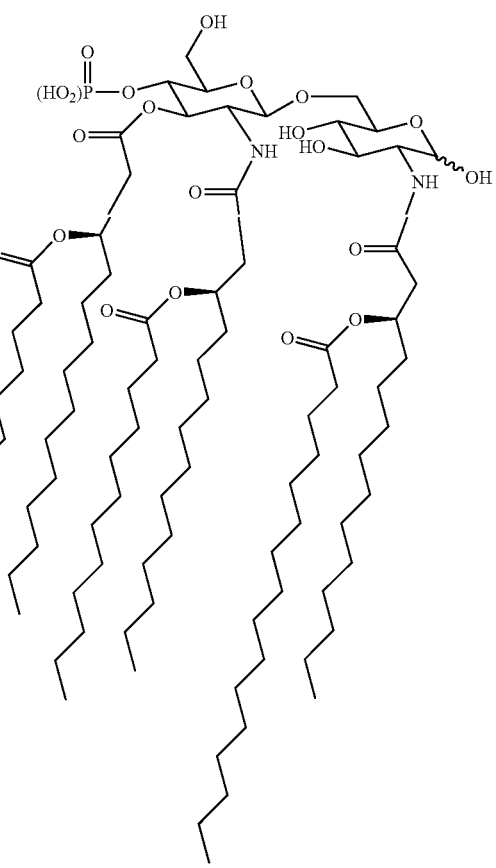

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [WO 94/21292]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g. ≧60%, ≧70%, ≧80%, ≧90%, or more) of the particles will have a diameter within the range x±25%.

3dMPL can advantageously be used in combination with an oil-in-water emulsion. Substantially all of the 3dMPL may be located in the aqueous phase of the emulsion. The 3dMPL can be used on its own, or in combination with one or more further compounds. For example, it is known to use 3dMPL in combination with the QS21 saponin [WO94/00153.] (including in an oil-in-water emulsion [WO95/17210]), with an immunostimulatory oligonucleotide, with both QS21 and an immunostimulatory oligonucleotide, with aluminum phosphate [WO96/26741], with aluminum hydroxide [WO93/19780], or with both aluminum phosphate and aluminum hydroxide.

Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Examples of CpG nucleotides include the following sequences, which may contain phosphorothioate modified internucleotide linkages:

TCC ATG ACG TTC CTG ACG TT (CpG 1826; SEQ ID NO: 1); TCT CCC AGC GTG CGC CAT (CpG1758; SEQ ID NO: 2); ACC GAT GAC GTC GCC GGT GAC GGC ACC ACG (SEQ ID NO: 3); TCG TCG TTT TGT CGT TTT GTC GTT (CpG 2006; SEQ ID NO: 4); and TCC ATG ACG TTC CTG ATG CT (CpG 1668; SEQ ID NO: 5). See WO 05/25614.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31 (part 3):664-658; Bhagat et al., "CpG penta- and hexadeoxyribonucleotides as potent immunomodulatory agents" BBRC (2003) 300:853-861 and WO03/035836.

ADP-Ribosylating Toxins and Detoxified Derivatives Thereof.

Bacterial ADP-ribosylating toxins and detoxified derivatives thereof may be used as adjuvants in the invention. Preferably, the protein is derived from *E. coli* (i.e., *E. coli* heat labile enterotoxin "LT), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon, et al., "The LTR72 Mutant of Heat-Labile Enterotoxin of *Escherichia coli* Enahnces the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol. (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280; Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol. (1995) 15(6):1165-1167.

Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention. E.g. WO99/27960.

Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Liposomes

Examples of liposome formulations suitable for use as adjuvants are described in U.S. Pat. No. 6,090,406, U.S. Pat. No. 5,916,588, and EP 0 626 169.

Polyoxyethylene ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

Small Molecule Immunopontentiators (SMIPs)

Imidazoquinoline Compounds.

Examples of imidazoquinoline compounds suitable for use adjuvants in the invention include Imiquimod and its analogues, described further in Stanley, "Imiquimod and the imidazoquinolines: mechanism of action and therapeutic potential" Clin Exp Dermatol (2002) 27(7):571-577; Jones, "Resiquimod 3M", Curr Opin Investig Drugs (2003) 4(2): 214-218; Wu et al. (2004) Antiviral Res. 64(2):79-83 Vasilakos et al. (2000) Cell Immunol. 204(1):64-74 U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.

Preferred SMIPs include:

N2-methyl-1-(2-methylpropyl)-1H-imidazo[4,5-c]quinoline-2,4-diamine;

N2,N2-dimethyl-1-(2-methylpropyl)-1H-imidazo[4,5-c]quinoline-2,4-diamine;

N2-ethyl-N2-methyl-1-(2-methylpropyl)-1H-imidazo[4,5-c]quinoline-2,4-diamine;

N2-methyl-1-(2-methylpropyl)-N2-propyl-1H-imidazo[4,5-c]quinoline-2,4-diamine;

1-(2-methylpropyl)-N2-propyl-1H-imidazo[4,5-c]quinoline-2,4-diamine;

N2-butyl-1-(2-methylpropyl)-1H-imidazo[4,5-c]quinoline-2,4-diamine;

N2-butyl-N2-methyl-1-(2-methylpropyl)-1H-imidazo[4,5-c]quinoline-2,4-diamine;

N2-methyl-1-(2-methylpropyl)-N2-pentyl-1H-imidazo[4,5-c]quinoline-2,4-diamine;

N2-methyl-1-(2-methylpropyl)-N2-prop-2-enyl-1H-imidazo[4,5-c]quinoline-2,4-diamine;

1-(2-methylpropyl)-2-[(phenylmethyl)thio]-1H-imidazo[4,5-c]quinolin-4-amine;

1-(2-methylpropyl)-2-(propylthio)-1H-imidazo[4,5-c]quinolin-4-amine;

2-[[4-amino-1-(2-methylpropyl)-1H-imidazo[4,5-c]quinolin-2-yl](methyl)amino]ethanol;

2-[[4-amino-1-(2-methylpropyl)-1H-imidazo[4,5-c]quinolin-2-yl](methyl)amino]ethyl acetate;

4-amino-1-(2-methylpropyl)-1,3-dihydro-2H-imidazo[4,5-c]quinolin-2-one;

N2-butyl-1-(2-methylpropyl)-N4,N4-bis(phenylmethyl)-1H-imidazo[4,5-c]quinoline-2,4-diamine;

N2-butyl-N2-methyl-1-(2-methylpropyl)-N4,N4-bis(phenylmethyl)-1H-imidazo[4,5-c]quinoline-2,4-diamine;

N2-methyl-1-(2-methylpropyl)-N4,N4-bis(phenylmethyl)-1H-imidazo[4,5-c]quinoline-2,4-diamine;

N2,N2-dimethyl-1-(2-methylpropyl)-N4,N4-bis(phenylmethyl)-1H-imidazo[4,5-c]quinoline-2,4-diamine;

1-{4-amino-2-[methyl(propyl)amino]-1H-imidazo[4,5-c]quinolin-1-yl}-2-methylpropan-2-ol;

1-[4-amino-2-(propylamino)-1H-imidazo[4,5-c]quinolin-1-yl]-2-methylpropan-2-ol;

N4,N4-dibenzyl-1-(2-methoxy-2-methylpropyl)-N2-propyl-1H-imidazo[4,5-c]quinoline-2,4-diamine.

Nucleoside Analogs.

A nucleoside analog, such as: (a) Isatorabine (ANA-245; 7-thia-8-oxoguanosine):

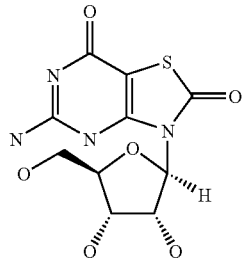

and prodrugs thereof, (b) ANA975; (c) ANA-025-1; (d) ANA380; (e) the compounds disclosed in references U.S. Pat. No. 6,924,271 to US2005/0070556 U.S. Pat. No. 5,658,731; (f) a compound having the Formula:

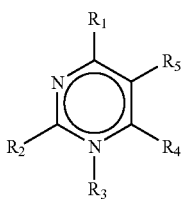

wherein:
R$_1$ and R$_2$ are each independently H, halo, —NR$_a$R$_b$, hydroxy, C$_{1-6}$ alkoxy, substituted C$_{1-6}$ alkoxy, heterocyclyl, substituted heterocyclyl, C$_{6-10}$ aryl, substituted C$_{6-10}$ aryl, C$_{1-6}$ alkyl, or substituted C$_{1-6}$ alkyl;
R$_3$ is absent, H, C$_{1-6}$ alkyl, substituted C$_{1-6}$ alkyl, C$_{6-10}$ aryl, substituted C$_{6-10}$ aryl, heterocyclyl, or substituted heterocyclyl;
R$_4$ and R$_5$ are each independently H, halo, heterocyclyl, substituted heterocyclyl, —C(O)—R$_d$, C$_{1-6}$ alkyl, substituted C$_{1-6}$ alkyl, or bound together to form a 5 membered ring as in R$_{4-5}$:

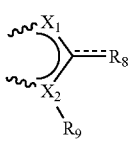

the binding being achieved at the bonds indicated by a ⌇
X$_1$ and X$_2$ are each independently N, C, O, or S;
R$_8$ is H, halo, hydroxy, C$_{1-6}$ alkyl, C$_{2-6}$ alkenyl, C$_{2-6}$ alkynyl, hydroxy, —NR$_a$R$_b$, —(CH$_2$)$_n$—O—R$^c$, —O—(C$_{1-6}$ alkyl), —S(O)$_p$R$_e$, or —C(O)—R$_d$;
R$_9$ is H, C$_{1-6}$ alkyl, substituted C$_{1-6}$ alkyl, heterocyclyl, substituted heterocyclyl or R$_{9a}$, wherein R$_{9a}$ is:

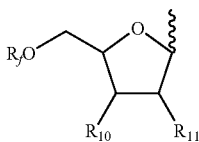

the binding being achieved at the bond indicated by a ⌇
R$_{10}$ and R$_{11}$ are each independently H, halo, C$_{1-6}$ alkoxy, substituted C$_{1-6}$ alkoxy, —NR$_a$R$_b$, or hydroxy;
each R$_a$ and R$_b$ is independently H, C$_{1-6}$ alkyl, substituted C$_{1-6}$ alkyl, —C(O)R$_d$, C$_{6-10}$ aryl;
each R$_c$ is independently H, phosphate, diphosphate, triphosphate, C$_{1-6}$ alkyl, or substituted C$_{1-6}$ alkyl;
each R$_d$ is independently H, halo, C$_{1-6}$ alkyl, substituted C$_{1-6}$ alkyl, C$_{1-6}$ alkoxy, substituted C$_{1-6}$ alkoxy, —NH$_2$, —NH(C$_{1-6}$ alkyl), —NH (substituted C$_{1-6}$ alkyl), —N(C$_{1-6}$ alkyl)$_2$, —N(substituted C$_{1-6}$ alkyl)$_2$, C$_{6-10}$ aryl, or heterocyclyl;
each R$_e$ is independently H, C$_{1-6}$ alkyl, substituted C$_{1-6}$ alkyl, C$_{6-10}$ aryl, substituted C$_{6-10}$ aryl, heterocyclyl, or substituted heterocyclyl;
each R$_f$ is independently H, C$_{1-6}$ alkyl, substituted C$_{1-6}$ alkyl, —C(O)R$_d$, phosphate, diphosphate, or triphosphate;

each n is independently 0, 1, 2, or 3;
each p is independently 0, 1, or 2; or
or (g) a pharmaceutically acceptable salt of any of (a) to (f), a tautomer of any of (a) to (f), or a pharmaceutically acceptable salt of the tautomer;
Loxoribine (7-allyl-8-oxoguanosine) [U.S. Pat. No. 5,011,828].

Thiosemicarbazone Compounds.

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-α.

Tryptanthrin Compounds.

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-α.

Additional SMIPs (i) Compounds disclosed in reference WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [U.S. Pat. No. 6,605,617, WO02/18383], Hydrapthalamide compounds, Benzophenone compounds, Isoxazole compounds, Sterol compounds, Quinazilinone compounds, Pyrrole compounds [WO2004/018455], Anthraquinone compounds, Quinoxaline compounds, Triazine compounds, Pyrazalopyrimidine compounds, and Benzazole compounds [WO03/082272].

(ii) Methyl inosine 5'-monophosphate ("MIMP") [Signorelli & Hadden (2003) *Int Immunopharmacol* 3(8):1177-86.].

(iii) A polyhydroxlated pyrrolizidine compound [WO2004/064715], such as one having Formula:

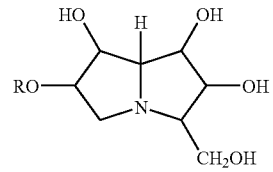

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

(iv) A gamma inulin [Cooper (1995) *Pharm Biotechnol* 6:559-80] or derivative thereof, such as algammulin.

Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable i vaccines. Bacterial toxins and bioadhesives are preferred adjuvants for use with mucosally-delivered vaccines, such as nasal vaccines.

TLR Modulators/Agonists

By "TLR agonist" it is meant a component which is capable of causing a signalling response through a TLR signalling pathway, either as a direct ligand or indirectly through generation of endogenous or exogenous ligand (Sabroe et al, Jl 2003 p 1630-5). TLR agonists of the present invention, include agonists of the following:

(1) TLR1: Tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S) Lys(4)-OH, trihydrochloride (Pam3Cys) LP which mimics the acetylated amino terminus of a bacterial lipoprotein and OspA LP from *Borrelia burgdorfei*);

(2) TLR2: one or more of a bacterial lipopeptide from *M tuberculosis, B burgdorferi. T pallidum*; peptidoglycans from species including *Staphylococcus aureus*; lipoteichoic acids, mannuronic acids, *Neisseria* porins, bacterial fimbriae, *Yersina* virulence factors, CMV virions, measles haemagglutinin, and zymosan from yeast;

(3) TLR3: double stranded RNA, or polyinosinic-polycytidylic acid (Poly IC), a molecular nucleic acid pattern associated with viral infection;

(4) TLR4: one or more of a lipopolysaccharide (LPS) from gram-negative bacteria, or fragments thereof, heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2. In one embodiment the TLR agonist is HSP 60, 70 or 90. In an alternative embodiment, the TLR agonist capable of causing a signalling response through TLR-4 is a non-toxic derivative of LPS. Monophosphoryl lipid A (MPL) and 3D-MPL as described above, is one such non-toxic derivative. Further adjuvants and TLR4 modulators include lipids linked to a phosphate-containing acyclic backbone, such as the TLR4 antagonist E5564 [Wong et al. (2003) *J Clin Pharmacol* 43(7):735-42, US2005/0215517]:

(5) TLR5: including bacterial flagellin;

(6) TLR6: including mycobacterial lipoprotein, di-acylated LP, and phenol-soluble modulin. Further TLR6 agonists are I described in WO2003043572;

(7) TLR7: including loxoribine, a guanosine analogue at positions N7 and C8, isatoribine, ANA-971, ANA-975, or an imidazoquinoline compound, or derivative thereof. In one embodiment, the TLR agonist is imiquimod or resiquimod. Further TLR7 agonists are described in WO02085905;

(8) TLR8: an imidazoquinoline molecule, for example resiquimod (R848); resiquimod is also capable of recognition by TLR-7. Other TLR-8 agonists which may be used include those described in WO2004071459; and/or (9) TLR9: In one embodiment, I the TLR agonist capable of causing a signalling response through TLR-9 is HSP90 or a DNA containing unmethylated CpG nucleotide, in particular sequence contexts described above with CpG motifs.

Preferred TLR modulators are agonists of TLR7 (e.g. imidazoquinolines) and/or TLR9 (e.g. CpG oligonucleotides).

Phospho-Containing Lipids

Compounds disclosed in reference PCT/JS2005/022769.

Phosphatidylcholine derivatives and phosphorylcholine containing molecules.

A compound of Formula (I), (II) or (III), or a salt thereof:

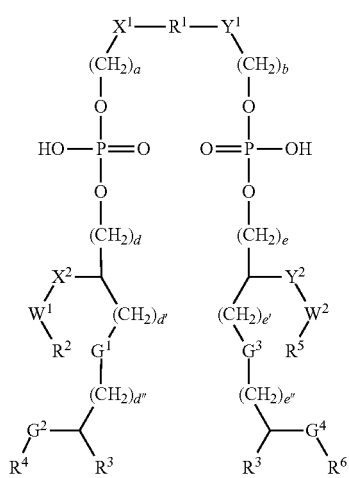

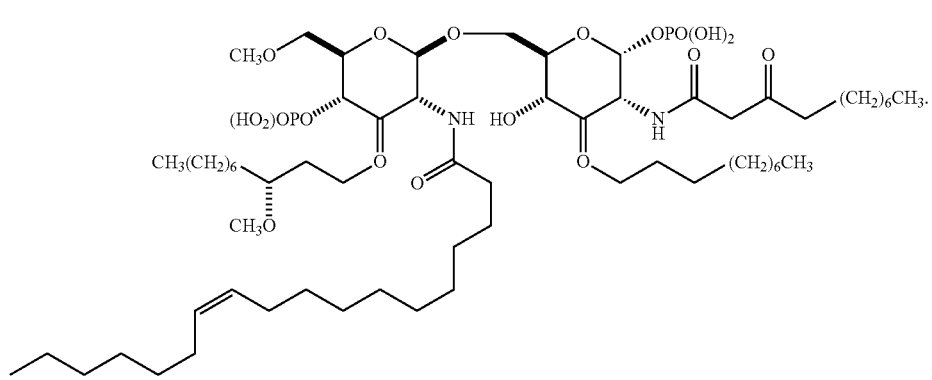

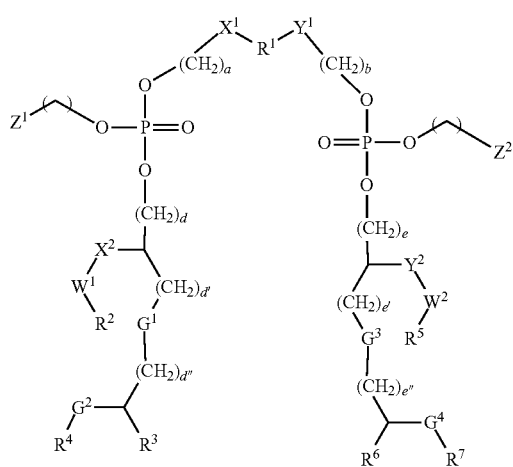
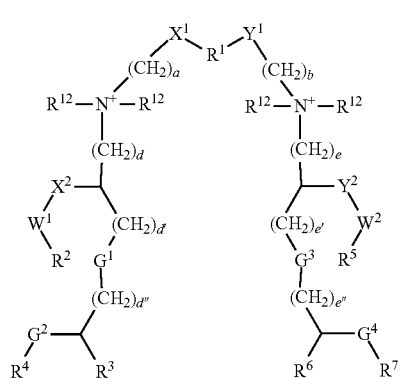
as defined in reference WO03/011223, such as 'ER 803058', 'ER 803732', 'ER 804053', 'ER 804058, 'ER 804059', 'ER 804442', 'ER 804680', '-ER 804764', ER 803022 or 'ER804057' e.g.:
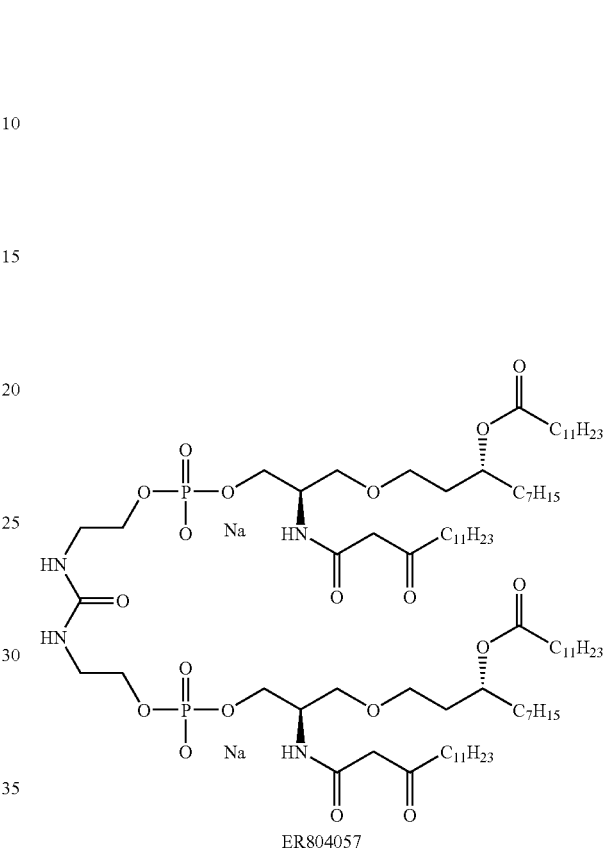
ER804057
ER-803022:
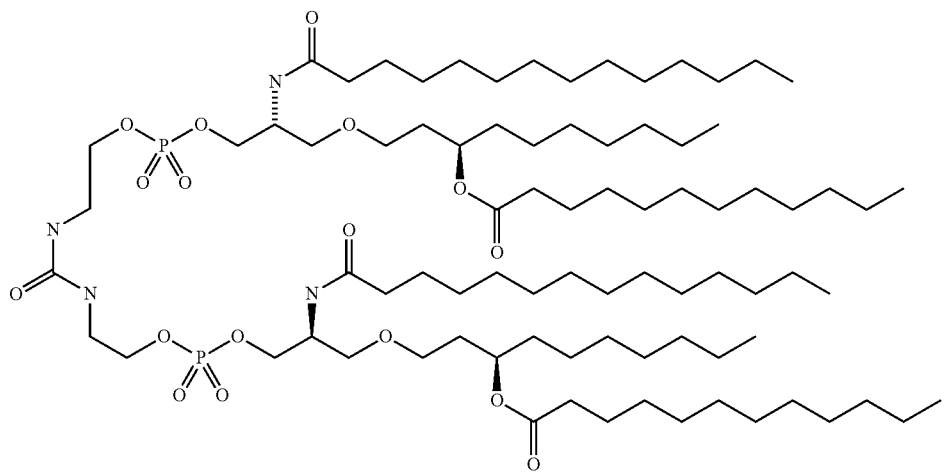

An aminoalkyl glucosaminide phosphate derivative, such as RC-529 [Johnson et al. (1999) *Bioorg Med Chem Lett* 9:2273-2278, Evans et al. (2003) *Expert Rev Vaccines* 2:219-229].

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g. QS21)+3dMPL+IL-12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% Tween 80, 5% pluronic-block polymer L121, and thr-MDP, either microfluidized into a submicron emulsion or vortexed to generate a larger particle size emulsion.

(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dPML).

(9) (9) one or more mineral salts (such as an aluminum salt)+an immunostimulatory oligonucleotide (such as a nucleotide sequence including a CpG motif).

The adjuvants described herein can be added to the composition at various stages during their production. For example, the adjuvant may be within or surround an antigen composition, and this mixture can then be/added to an oil-in-water emulsion. As an alternative, the antigen and/adjuvant may be within an oil-in-water emulsion, in which case the agent can either be added to the emulsion components before emulsification, or it can be added to the emulsion after emulsification. Similarly, the agent may be coacervated within the emulsion droplets. The location and distribution of the adjuvant within the final composition will depend on its hydrophilic/lipophilic properties e.g. the agent can be located in the aqueous phase, in the oil phase, and/or at the oil-water interface.

Further, the adjuvant described herein can be conjugated to a separate agent, such as an antigen (e.g. CRM197) or directly to any amenable composition of the present invention. A general review of conjugation techniques for small molecules is provided in Thompson et al. (2003) Methods in Molecular Medicine 94:255-266. Preferred conjugation methods involve directly coupling through reductive amination or via a linker, such as adipic acid or squarate. As an alternative, the adjuvants may be non-covalently associated with additional agents, such as by way of hydrophobic or ionic interactions.

The invention is also directed to methods of administering the immunogenic compositions of the invention, wherein the immunogenic composition can include in one embodiment one or more adjuvants and antigens as described herein in combination with a compound of Formula (I) or (II). In some embodiments, the immunogenic composition is administered to the subject in an amount effective to stimulate an immune response. The amount that constitutes an effective amount depends, inter alia, on the particular immunogenic composition used, the particular adjuvant compound being administered and the amount thereof, the immune response that is to be enhanced (humoral or cell mediated), the state of the immune system (e.g., suppressed, compromised, stimulated), and the desired therapeutic result. Accordingly it is not practical to set forth generally the amount that constitutes an effective amount of the immunogenic composition. Those of ordinary skill in the art, however, can readily determine the appropriate amount with due consideration of such factors.

The compositions of the invention can be administered to various animals subjects including mammals such as human and non-human subjects, including, for example, pocket pets, fowl, and the like according to conventional methods well-known to those skilled in the art.

The immunogenic compositions of the present invention can be used in the manufacture of a vaccine. Suitable vaccines include, but are not limited to, any material that raises either or both humoral or cell mediated immune response. Suitable vaccines can include live viral and bacterial antigens and inactivated viral, tumor-derived, protozoal, organism-derived, fungal, and bacterial antigens, toxoids, toxins, polysaccharides, proteins, glycoproteins, peptides, and the like, numerous examples of which are described below.

Antigens:

Compositions of the invention may be administered in conjunction with one or more antigens for use in therapeutic, prophylactic, or diagnostic methods of the present invention. Preferred antigens include those listed below. Additionally, the compositions of the present invention may be used to treat or prevent infections caused by any of the below-listed pathogens. In addition to combination with the antigens described below, the compositions of the invention may also be combined with an adjuvant as described herein.

Antigens for use with the invention include, but are not limited to, one or more of the following antigens set forth below, or antigens derived from one or more of the pathogens set forth below:

A. Bacterial Antigens

Bacterial antigens suitable for use in the invention include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides*: Meningitides antigens may include proteins (such as those identified in References 1-7), saccharides (including a polysaccharide, oligosaccharide or lipopolysaccharide), or outer-membrane vesicles (References 8, 9, 10, 11) purified or derived from *N. meningitides* serogroup such as A, C, W135, Y, and/or B. Meningitides protein antigens may be selected from adhesions, autotransporters, toxins, Fe acquisition proteins, and membrane associated proteins (preferably integral outer membrane protein).

*Streptococcus pneumoniae*: *Streptococcus pneumoniae* antigens may include a saccharide (including a polysaccharide or an oligosaccharide) and/or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. No. 6,699,703, U.S. Pat. No. 6,800, 744, WO 97/43303, and WO 97/37026. *Streptococcus pneu-*

*moniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis*: *Moraxella* antigens include antigens identified in WO 02/18595 and WO 99/58562, outer membrane protein antigens (HMW-OMP), C-antigen, and/or LPS.

*Bordetella pertussis*: Pertussis antigens include *petussis* holotoxin (PT) and filamentous haemagglutinin (FHA) from *B. pertussis*, optionally also combination with pertactin and/ or agglutinogens 2 and 3 antigen.

*Staphylococcus aureus*: Staph aureus antigens include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis*: *S. epidermidis* antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as $CRM_{197}$. Additionally antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib antigens include a Hib saccharide antigen.

*Pseudomonas aeruginosa*: *Pseudomonas* antigens include endotoxin A, Wzz protein, *P. aeruginosa* LPS, more particularly LPS isolated from PAO1 (O5 serotype), and/or Outer Membrane Proteins, including Outer Membrane Proteins F (OprF) (*Infect Immun*. 2001 May; 69(5): 3510-3515).

*Legionella pneumophila*. Bacterial antigens may be derived from *Legionella pneumophila*.

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS104, GBS 276 and GBS 322, and including saccharide antigens derived from serotypes Ia, Ib, Ia/c, II, III, IV, V, VI, VII and VIII).

*Neiserria gonorrhoeae*: Gonorrhoeae antigens include Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243).

*Chlamydia trachomatis*: *Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia* trachomas antigens may also include an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): Ducreyi antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori*: *H pylori* antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* Antigens include LPS (*Infect Immun*. 2002 August; 70(8): 4414).

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which can share a common B-component known as protective antigen (PA).

*Yersinia pestis* (plague): Plague antigens include F1 capsular antigen (*Infect Immun*. 2003 January; 71(1)): 374-383, LPS (*Infect Immun*. 1999 October; 67(10): 5395), *Yersinia pestis* V antigen (*Infect Immun*. 1997 November; 65(11): 4476-4482).

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles (Infect Immun. 2004 October; 72(10): 6148), *Mycobacterium tuberculosis* (Mtb) isocitrate dehydrogenase associated antigens (*Proc Natl Acad Sci USA*. 2004 Aug. 24; 101(34): 12652), and/or MPT51 antigens (Infect Immun. 2004 July; 72(7): 3829).

*Rickettsia*: Antigens include outer membrane proteins, including the outer membrane protein A and/or B (OmpB) (*Biochim Biophys Acta*. 2004 Nov. 1; 1702(2):145), LPS, and surface protein antigen (SPA) (*J Autoimmun*. 1989 June; 2 Suppl:81).

*Listeria monocytogenes*. Bacterial antigens may be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* O139, antigens of IEM108 vaccine (*Infect Immun*. 2003 October; 71(10):5498-504), and/or Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, *Infect Immun.* 2001 May; 69(5): 3323-3334), VlsE Antigenic Variation Protein (*J Clin Microbiol.* 1999 December; 37(12): 3997).

*Porphyromonas gingivalis*: Antigens include *P. gingivalis* outer membrane protein (OMP).

*Klebsiella*: Antigens include an OMP, including OMP A, or a polysaccharide optionally conjugated to tetanus toxoid.

Further bacterial antigens of the invention may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens of the present invention may be derived from gram-negative or gram-positive bacteria. The antigens of the present invention may be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897 and *Can J Biochem Cell Biol.* 1984 May; 62(5):270-5. Alternatively, the saccharides can be conjugated through a linker, such as, with succinamide or other linkages provided in *Bioconjugate Techniques,* 1996 and *CRC, Chemistry of Protein Conjugation and Cross-Linking,* 1993.

B. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., *J Gen Virol.* 2004 November; 85(Pt 11):3229). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as *Rubella* virus, are preferred. Togavirus antigens may be selected from E1, E2, E3, C, NSP-1, NSPO-2, NSP-3 or NSP-4. Togavirus antigens are preferably selected from E1, E2 or E3. Commercially available *Rubella* vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). (see, e.g. Hsu et al. (1999) *Clin Liver Dis* 3:901-915). HCV antigens may be selected from one or more of E1, E2, E1/E2, NS345 polyprotein, NS 345-core polyprotein, core, and/or peptides from the nonstructural regions (Houghton et al., *Hepatology* (1991) 14:381). For example, Hepatitis C virus antigens that may be used can include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity (see, e.g. WO03/002065; WO01/37869 and WO04/005473).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens may be derived from Caliciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55 gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LAI}$, $HTV_{MN}$, $HIV\text{-}1_{CM235}$, $HIV\text{-}1_{US4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, µ1, µ2, σ1, σ2, or σ3, or nonstructural proteins σNS, µNS, or σ1s. Preferred Reovirus antigens may be derived from a Rotavirus. Rotavirus antigens may be selected from VP1, VP2, VP3, VP4 (or the cleaved product VP5 and VP8), NSP1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly δ-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomavirus viruses include BK virus and JK virus. Polyomavirus antigens may be selected from VP1, VP2 or VP3.

Further provided are antigens, compositions, methods, and microbes included in *Vaccines*, $4^{th}$ Edition (Plotkin and Orenstein ed. 2004); *Medical Microbiology* $4^{th}$ Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the compositions of the present invention.

C. Fungal Antigens

Fungal antigens for use in the invention may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immi-* tis, *Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marnefei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

D. STD Antigens

The compositions of the invention may include one or more antigens derived from a sexually transmitted disease (STD). Such antigens may provide for prophylactis or therapy for STD's such as chlamydia, genital herpes, hepatits (such as HCV), genital warts, gonorrhoea, syphilis and/or chancroid (See, WO00/15255). Antigens may be derived from one or more viral or bacterial STD's. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli*, and *Streptococcus agalactiae*. Examples of specific antigens derived from these pathogens are described above.

E. Respiratory Antigens

The compositions of the invention may include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis*, and *Moraxella catarrhalis*. Examples of specific antigens derived from these pathogens are described above.

F. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens may be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli*. Examples of specific antigens derived from these pathogens are described above.

G. Antigens Suitable for Use in Elderly or Immunocompromised Individuals

The compositions of the invention may include one or more antigens suitable for use in elderly or immunocompromised individuals. Such individuals may need to be vaccinated more frequently, with higher doses or with adjuvanted formulations to improve their immune response to the targeted antigens. Antigens which may be targeted for use in Elderly or Immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae*, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

H. Antigens Suitable for Use in Adolescent Vaccines

The compositions of the invention may include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

I. Tumor Antigens

One embodiment of the present involves a tumor antigen or cancer antigen in conjunction with the compositions of the present invention. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen. The tumor antigen can further be, for example, a polynucleotide-containing tumor antigen that expresses a polypeptide-containing tumor antigen, for instance, an RNA vector construct or a DNA vector construct, such as plasmid DNA.

Tumor antigens appropriate for the practice of the present invention encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

The tumor antigens can be, for example, (a) full length molecules associated with cancer cells, (b) homologs and modified forms of the same, including molecules with deleted, added and/or substituted portions, and (c) fragments of the same. Tumor antigens can be provided in recombinant form. Tumor antigens include, for example, class I-restricted antigens recognized by CD8+ lymphocytes or class TI-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUMI (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Additional tumor antigens which are known in the art include p15, Hom/MeI-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding proteincyclophilin C-associated protein), TAAL6, TAG72, TLP, TPS, and the like. These as well as other cellular components are described for example in United States Patent Application 20020007173 and references cited therein.

Polynucleotide-containing antigens in accordance with the present invention typically comprise polynucleotides that encode polypeptide cancer antigens such as those listed above. Preferred polynucleotide-containing antigens include DNA or RNA vector constructs, such as plasmid vectors (e.g., pCMV), which are capable of expressing polypeptide cancer antigens in vivo.

Tumor antigens may be derived, for example, from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693,522 and references cited therein.

Additionally, bacterial and viral antigens, may be used in conjunction with the compositions of the present invention for the treatment of cancer. In particular, carrier proteins, such as $CRM_{197}$, tetanus toxoid, or *Salmonella typhimurium* antigen can be used in conjunction/conjugation with compounds of the present invention for treatment of cancer. The cancer antigen combination therapies will show increased efficacy and bioavailability as compared with existing therapies.

Additional information on cancer or tumor antigens can be found, for example, in Moingeon P, "Cancer vaccines," Vaccine, 2001, 19:1305-1326; Rosenberg S A, "Progress in human tumor immunology and immunotherapy," Nature, 2001, 411:380-384; Dermine, S. et al, "Cancer Vaccines and Immunotherapy," British Medical Bulletin, 2002, 62, 149-162; Espinoza-Delgado I., "Cancer Vaccines," The Oncologist, 2002, 7(suppl3):20-33; Davis, I. D. et al., "Rational approaches to human cancer immunotherapy," Journal of Leukocyte Biology, 2003, 23: 3-29; Van den Eynde B, et al., "New tumor antigens recognized by T cells," Curr. Opin. Immunol., 1995, 7:674-81; Rosenberg S A, "Cancer vaccines based on the identification of genes encoding cancer regression antigens, Immunol. Today, 1997, 18:175-82; Offring a R et al., "Design and evaluation of antigen-specific vaccination strategies against cancer," Current Opin. Immunol., 2000, 2:576-582; Rosenberg S A, "A new era for cancer immunotherapy based on the genes that encode cancer antigens," Immunity, 1999, 10:281-7; Sahin U et al., "Serological identification of human tumor antigens," Curr. Opin. Immunol., 1997, 9:709-16; Old L J et al., "New paths in human cancer serology," J. Exp. Med., 1998, 187:1163-7; Chaux P, et al., "Identification of MAGE-3 epitopes presented by HLA-DR molecules to CD4(+) T lymphocytes," J. Exp. Med., 1999, 189:767-78; Gold P, et al., "Specific carcinoembryonic antigens of the human digestive system," J. Exp. Med., 1965, 122:467-8; Livingston P O, et al., Carbohydrate vaccines that induce antibodies against cancer: Rationale," Cancer Immunol. Immunother., 1997, 45:1-6; Livingston P O, et al., Carbohydrate vaccines that induce antibodies against cancer: Previous experience and future plans," Cancer Immunol. Immunother., 1997, 45:10-9; Taylor-Papadimitriou J, "Biology, biochemistry and immunology of carcinoma-associated mucins," Immunol. Today, 1997, 18:105-7; Zhao X-J et al., "GD2 oligosaccharide: target for cytotoxic T lymphocytes," J. Exp. Med., 1995, 182:67-74; Theobald M, et al., "Targeting p53 as a general tumor antigen," Proc. Natl. Acad. Sci. USA, 1995, 92:11993-7; Gaudernack G, "T cell responses against mutant ras: a basis for novel cancer vaccines," Immunotechnology, 1996, 2:3-9; WO 91/02062; U.S. Pat. No. 6,015,567; WO 01/08636; WO 96/30514; U.S. Pat. No. 5,846,538; and U.S. Pat. No. 5,869,445.

Antigen Formulations

In other aspects of the invention, methods of producing microparticles having adsorbed antigens are provided. The methods comprise: (a) providing an emulsion by dispersing a mixture comprising (i) water, (ii) a detergent, (iii) an organic solvent, and (iv) a biodegradable polymer selected from the group consisting of a poly($\alpha$-hydroxy acid), a polyhydroxy butyric acid, a polycaprolactone, a polyorthoester, a polyanhydride, and a polycyanoacrylate. The polymer is typically present in the mixture at a concentration of about 1% to about 30% relative to the organic solvent, while the detergent is typically present in the mixture at a weight-to-weight detergent-to-polymer ratio of from about 0.00001:1 to about 0.1:1 (more typically about 0.0001:1 to about 0.1:1, about 0.001:1 to about 0.1:1, or about 0.005:1 to about 0.1:1); (b) removing the organic solvent from the emulsion; and (c) adsorbing an antigen on the surface of the microparticles. In certain embodiments, the biodegradable polymer is present at a concentration of about 3% to about 10% relative to the organic solvent.

Microparticles for use herein will be formed from materials that are sterilizable, non-toxic and biodegradable. Such materials include, without limitation, poly($\alpha$-hydroxy acid), polyhydroxybutyric acid, polycaprolactone, polyorthoester, polyanhydride, PACA, and polycyanoacrylate. Preferably, microparticles for use with the present invention are derived from a poly($\alpha$-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

Further antigens may also include an outer membrane vesicle (OMV) preparation.

Additional formulation methods and antigens (especially tumor antigens) are provided in U.S. patent Ser. No. 09/581, 772.

Pharmaceutical compositions that include the compounds described herein may include additives such as excipients. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-$\beta$-cyclodextrin, polyvinylpyrrolidinone, low melting waxes, ion exchange resins, and the like, as well as combinations of any two or more of these. Other suitable pharmaceutically acceptable excipients are described in "Remington's Pharmaceutical Sciences," Mack Pub. Co., New Jersey (1991), which is hereby incorporated herein by reference in its entirety and for all purposes as if fully set forth herein.

Pharmaceutical compositions that include the compounds of the invention may be in any form suitable for the intended method of administration, including, for example, as a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more of these. The liquid carrier may include other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, but are not limited to, soybean oil, coconut oil, olive oil, safflower oil, cottonseed oil, and the like. For parenteral administration, the carrier may be an oily ester such as ethyl oleate, isopropyl myristate, and the like. Compositions of the present invention may also be in the form of microparticles, microcapsules, and the like, as well as combinations of any two or more of these.

The compounds and combinations of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form may include, in addition to a compound of the present invention, stabilizers, preservatives, excipients, and the like. Preferred lipids include phospholipids and phosphatidyl cholines (lecithins), both natural and synthetic. Methods of forming liposomes are known in the art. See, for example, Prescott, Ed., *Methods in Cell Biology*, Volume XIV, Academic Press, New York, N.W., p. 33 et seq (1976).

Controlled release delivery systems may also be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, intradermally, by inhalation spray, rectally, or topically in dosage unit formulations that include conventional nontoxic pharmaceutically acceptable carriers, adjuvants, and vehicles as desired. For example, suitable modes of administration include oral, subcutaneous, transdermal, transmucosal, iontophoretic, intravenous, intramuscular, intraperitoneal, intranasal, subdermal, rectal, and the like. Topical administration may also include the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will, therefore, melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also include, as is normal practice, additional substances other than inert diluents, e.g., lubricating agents such as magnesium stearate. In the case of capsules, tablets, and pills, the dosage forms may also include buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

Effective amounts of the compounds of the invention generally include any amount sufficient to detectably treat the disorders described herein.

Successful treatment of a subject in accordance with the invention may result in a reduction or alleviation of symptoms in a subject afflicted with a medical or biological disorder. For example, treatment may halt the further progression of the disorder, or may prevent or retard development of the disorder.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and severity of the particular disease undergoing therapy. The therapeutically effective amount for a given situation can be readily determined by routine experimentation and is within the skill and judgment of the ordinary clinician.

ANTIGEN REFERENCES

The following references include antigens useful in conjunction with the compositions of the present invention:
Antigen references are listed below:
1. International patent application WO 99/24578
2. International patent application WO 99/36544.
3. International patent application WO 99/57280.
4. International patent application WO 00/22430.
5. Tettelin et al. (2000) Science 287:1809-1815.
6. International patent application WO 96/29412.
7. Pizza et al. (2000) Science 287:1816-1820.
8. PCT WO 01/52885.
9. Bjune et al. (1991) Lancet 338(8775).
10. Fuskasawa et al. (1999) Vaccine 17:2951-2958.
11. Rosenqist et al. (1998) Dev. Biol. Strand 92:323-333.
12. Constantino et al. (1992) Vaccine 10:691-698.
13. Constantino et al. (1999) Vaccine 17:1251-1263.
14. Watson (2000) Pediatr Infect Dis J 19:331-332.
15. Rubin (20000) Pediatr Clin North Am 47:269-285, v.
16. Jedrzejas (2001) Microbiol Mol Biol Rev 65:187-207.
17. International patent application filed on 3 Jul. 2001 claiming priority from GB-0016363.4; WO 02/02606; PCT IB/01/00166.
18. Kalman et al. (1999) Nature Genetics 21:385-389.
19. Read et al. (2000) Nucleic Acids Res 28:1397-406.
20. Shirai et al. (2000) J. Infect. Dis 181(Suppl 3):S524-S527.
21. International patent application WO 99/27105.
22. International patent application WO 00/27994.
23. International patent application WO 00/37494.
24. International patent application WO 99/28475.
25. Bell (2000) Pediatr Infect Dis J 19:1187-1188.
26. Iwarson (1995) APMIS103:321-326.
27. Gerlich et al. (1990) Vaccine 8 Suppl:S63-68 & 79-80.
28. Hsu et al. (1999) Clin Liver Dis 3:901-915.
29. Gastofsson et al. (1996) N. Engl. J. Med. 334-:349-355.
30. Rappuoli et al. (1991) TIBTECH 9:232-238.
31. Vaccines (1988) eds. Plotkin & Mortimer. ISBN 0-7216-1946-0.
32. Del Guidice et al. (1998) Molecular Aspects of Medicine 19:1-70.
33. International patent application WO 93/018150.
34. International patent application WO 99/53310.
35. International patent application WO 98/04702.
36. Ross et al. (2001) Vaccine 19:135-142.
37. Sutter et al. (2000) Pediatr Clin North Am 47:287-308.
38. Zimmerman & Spann (1999) Am Fan Physician 59:113-118, 125-126.
39. Dreensen (1997) Vaccine 15 Suppl"S2-6.
40. MMWR Morb Mortal Wkly rep 1998 Jan. 16:47(1):12, 9.
41. McMichael (2000) Vaccine 19 Suppl 1: S101-107.
42. Schuchat (1999) Lancer 353(9146):51-6.
43. GB patent applications 0026333.5, 0028727.6 & 0105640.7.
44. Dale (1999) Infect Disclin North Am 13:227-43, viii.
45. Ferretti et al. (2001) PNAS USA 98: 4658-4663.
46. Kuroda et al. (2001) Lancet 357(9264):1225-1240; see also pages 1218-1219.
47. Ramsay et al. (2001) Lancet 357(9251):195-196.
48. Lindberg (1999) Vaccine 17 Suppl 2:S28-36.
49. Buttery & Moxon (2000) J R Coil Physicians Long 34:163-168.

50. Ahmad & Chapnick (1999) Infect Dis Clin North Am 13:113-133, vii.
51. Goldblatt (1998) J. Med. Microbiol. 47:663-567.
52. European patent 0477508.
53. U.S. Pat. No. 5,306,492.
54. International patent application WO 98/42721.
55. Conjugate Vaccines (eds. Cruse et al.) ISBN 3805549326, particularly vol. 10:48-114.
56. Hermanson (1996) Bioconjugate Techniques ISBN: 012323368 & 012342335X.
57. European patent application 0372501.
58. European patent application 0378881.
59. European patent application 0427347.
60. International patent application WO 93/17712.
61. International patent application WO 98/58668.
62. European patent application 0471177.
63. International patent application WO 00/56360.
64. International patent application WO 00/67161.

DEFINITIONS

As used above and elsewhere herein the following terms and abbreviations have the meanings defined below:
AcH Acetic Acid
ATP Adenosine triphosphate
BCG *Mycobacterium bovis bacillus* Calmette-Guerin
Bn Benzyl
BSA Bovine Serum Albumin
DCM Dichloromethane
DIEA N,N-diisopropyl-ethylamine
EDC 1-(3-Dimethylaminopropyl)-3-ethylcarbodiimide hydrochloride
FHA Filamentous haemaglutinin
GCMS Gas Chromatography/Mass Spectroscopy
*H. Pylori Helicobacter Pylori*
HAV Hepatitis A Virus
HBV Hepatitis B Virus
HBr Hydrogen Bromide
HCV Hepatitis C Virus
HIV Human Immunodeficiency Virus
HPLC High Performance Liquid Chromatography
HSV Herpes Simplex Virus
$IC_{50}$ value The concentration of an inhibitor that causes a 50% reduction in a measured activity.
IFN Interferon
IL Interleukin
IMS Immunomagnetic separation
IPV Inactivated polio virus
LCMS Liquid Chromatography/Mass Spectroscopy
LPS Lipid polysaccharide
MAb or mAb Monoclonal Antibody
Men A *Neisseria Meningitidis* Type A
Men C *Neisseria Meningitidis* Type C
Men B *Neisseria Meningitidis* Type B
Men W *Neisseria Meningitidis* Type W
Men Y *Neisseria Meningitidis* Type Y
MeOH Methanol
MW Molecular Weight
NANB Non-A, non-B hepatitis
NMR Nuclear magnetic resonance
OMV Outer membrane vesicle
PBMC Peripheral blood mononuclear cells
PT *Pertussis* holotoxin
Rt Room temperature (25° C.)
SMIP Small Molecule Immune Potentiator
tBOK Potassium Tertiary Butoxide
TEA Triethylamine
OTf Triflate
THF Tetrahydrofuran
TLC Thin Layer Chromatography and/or Tender Loving Care
TMS Trimethylsilyl
TNF-α Tumour necrosis factor-alpha The term "SMIP" refers to a small molecule immunopotentiating compound, including small molecule compounds, generally below about MW 800 g/mol, capable of stimulating or modulating a pro-inflammatory response in a patient. In some embodiments, the SMIP compounds are able to stimulate human peripheral blood mononuclear cells to produce cytokines. More particularly, preferred SMIPs include Imidazopyridines and those compounds encompassed by Formula (I) or (II) described herein, or contained within any reference cited herein.

The term "SMIS" refers to a small molecule immunosuppressant compound, including small molecule compounds, generally below about MW 800 g/mol, capable of suppressing or modulating an immune response in a patient. In some embodiments, the SMIS compounds are able to inhibit human peripheral blood mononuclear cell's ability to produce cytokines, chemokines, and/or growth factors. In other embodiments, the SMIS compounds are able to induce TGF-beta production, thereby suppressing an immune response.

Reference to "imidazopyridine" (as pertaining to imidazopyridine compounds and imidazopyridines of the present invention), indicates compounds having the general structure of Formula (I) as described herein. In some embodiments, $R^4$ and $R^5$ of the general structure of Formula (I) are independently selected from H, aryl, heteroaryl, —$NHR^8$ and —$OR^9$. In some embodiments, $R^4$ and $R^5$ of the general structure of Formula (I) together with the two carbon atoms to which they are attached form an optionally substituted 5-6 membered heteroaryl group [i.e., the imidazopyridine ring of the Formula (I) can further be fused with an additional heteroaryl ring, such as in the compound of Formula (II) described herein]. Some preferred imidazopyridines and derivatives thereof include compounds of Formulas:

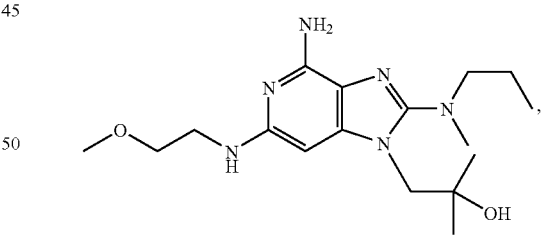

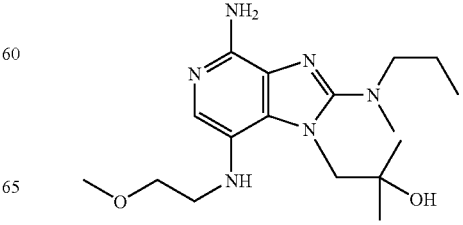

-continued

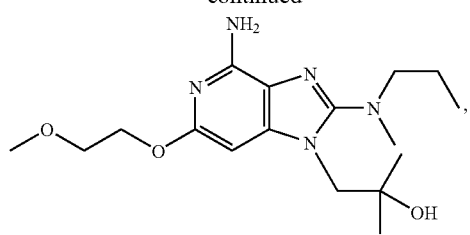,

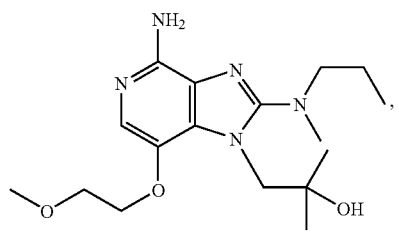,

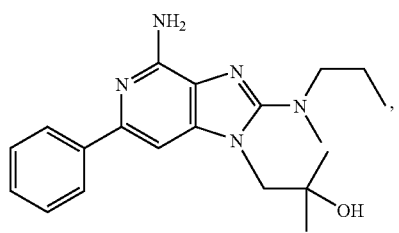,

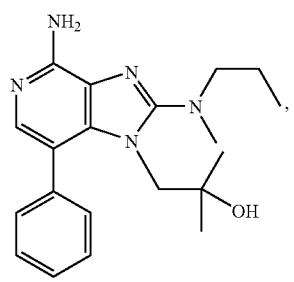,

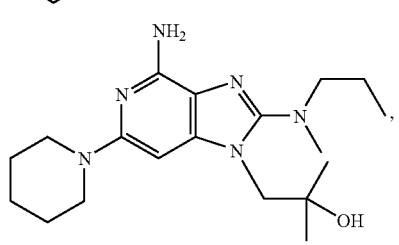,

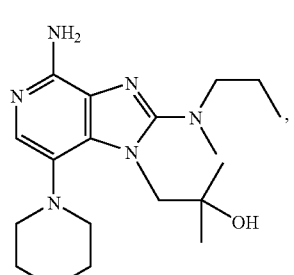,

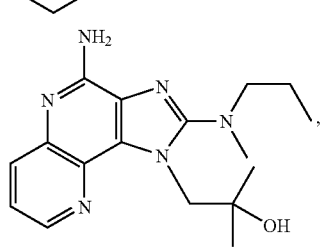,

-continued

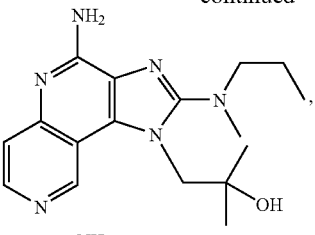,

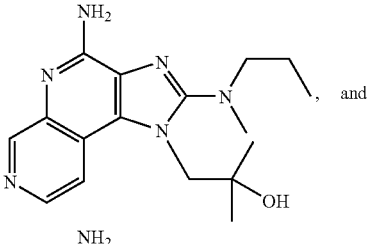, and

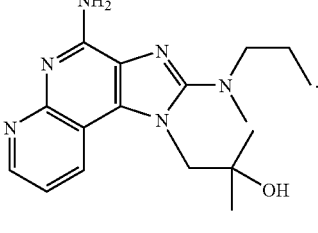.

The term "refractory cancer cells" refers to cancer cell lines that are resistant to preexisting therapeutics or treatment regimens, including prescribed dosing schedules.

The methods of the invention are useful in treating "allergic diseases," which may be accomplished in the same manner as the other immunotherapeutic methods described herein.

An "allergen" refers to a substance (antigen) that can induce an allergic or asthmatic response in a susceptible subject. The list of allergens is enormous and can include pollens, insect venoms, animal dander, dust, fungal spores, and drugs (e.g., penicillin).

"Asthma" refers to a disorder of the respiratory system characterized by inflammation, narrowing of the airways, and increased reactivity of the airways to inhaled agents. Asthma is frequently, although not exclusively, associated with atopic or allergic symptoms.

The term "leukotriene inhibitor" includes any agent or compound that inhibits, restrains, retards, or otherwise interacts with the action or activity of leukotrienes, such as, but not limited to, 5-lipoxygenase ("5-LO") inhibitors, 5-lipoxygenase activating protein ("FLAP") antagonists, and leukotriene D4 ("LTD4") antagonists.

"Modulating" refers to inducing or suppressing.

"Immune-stimulation" or "immune potentiation" of "immune response" refers to activation of the immune system, including humoral or cellular activation, for example, activation of a cell, such as a killer (T or NK) or dendritic cell of the immune system, for example, causing the increase in cytokine production from a dendritic cell leading to an overall enhancement of host defense.

"Modulating an immune response" refers to either immune potentiation or immune suppression as defined herein.

An "immunogenic composition" refers to a composition capable of stimulating an immune response. In some embodiments, "immunogenic compositions" are compositions capable of stimulating an immune response in a subject. In some embodiments, the immunogenic composition is capable of modulating the production of cytokines in a subject, thereby effecting immune potentiation in that subject.

"Immune suppression" or "immunosuppression" refers to deactivation of the immune system, for example, preventing or lessening cytokine production from a dendritic cell leading to an overall attenuation of host defense (immune response).

An "immune-stimulatory effective amount" is an amount effective for activating the immune system, for example, causing an increase in cytokine production from a dendritic cell leading to an overall enhancement of host defense (immune response).

"Enhancing the immune response to an antigen" by a compound refers to enhancement of the immune response in comparison to that in the absence of the compound. An enhanced immune-response eliciting composition is a composition generally comprising an antigen and a small molecule immune potentiator compound that elicits an immune response greater than a composition comprising an antigen and not containing one or more small molecule immune potentiator compounds. In such embodiments, the compound acts as an adjuvant, for example, for use in vaccine compositions and methods.

A "disease associated with cellular proliferation" includes, but is not limited to neuro-fibromatosis, atherosclerosis, pulmonary fibrosis, arthritis, psoriasis, glomerulonephritis, restenosis, proliferative diabetic retinopathy (PDR), hypertrophic scar formation, inflammatory bowel disease, transplantation rejection, angiogenesis, and endotoxic shock.

The term "effective amount" is an amount necessary or sufficient to realize a desired biological effect. For example, an effective amount of a compound to treat an infectious disorder may be an amount necessary to cause an antigen specific immune response upon exposure to an infectious agent. The effective amount may vary, depending, for example, upon the condition treated, weight of the subject and severity of the disease. One of skill in the art can readily determine the effective amount empirically without undue experimentation.

As used herein "an effective amount for treatment" refers to an amount sufficient to palliate, ameliorate, stabilize, reverse, slow or delay progression of a condition such as a disease state.

Reference to "metronomic administration" or "administered metronomically" refers to increasingly frequent dosing regimens, at lower drug concentrations, as compared with known dosing regimens for an existing therapeutic. Metronomic administration varies from the typical dosing of cytotoxic drugs, which involves episodic (less frequent) administration at maximum tolerated doses (MTDs).

A "subject" or "patient" is meant to describe a human or vertebrate animal including a dog, cat, pocket pet, marmoset, horse, cow, pig, sheep, goat, elephant, giraffe, chicken, lion, monkey, owl, rat, squirrel, slender loris, and mouse.

A "pocket pet" refers to a group of vertebrate animals capable of fitting into a commodious coat pocket such as, for example, hamsters, chinchillas, ferrets, rats, guinea pigs, gerbils, rabbits and sugar gliders. Further description is provided by Mackay, B., *Pocket Pets*, Animal Issues, 32(1) 2001.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The compounds of the present invention can be used in the form of salts as in "pharmaceutically acceptable salts" derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, sulfate, 3-phenylpropionate, picrate, pivalate, propionate, succinate, tartrate, thiocyanate, p-toluenesulfonate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above Formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987. Prodrugs as described in U.S. Pat. No. 6,284,772 for example may be used.

The symbol  is meant to indicate the point of attachment of an appendage.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. The phrase "$C_{1-6}$ alkyl" has the same meaning as alkyl, except that it is limited to alkyl groups of six carbons or less. The phrase $C_{1-6}$ alkyl also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$C(CH$_3$)$_3$, —CH(CH$_3$)CH$_2$CH(CH$_3$)$_2$, —CH(CH$_3$)CH(CH$_3$)CH(CH$_3$), and others.

As used herein, "alkenyl" refers to an alkyl group having one or more double carbon-carbon bonds. Example alkenyl groups include ethenyl, propenyl, and the like. The term "alkenylenyl" or "alkenylene" refers to a linking alkenyl group between two moieties in a molecule. The alkenylenyl groups, like all other groups, can further be substituted as described herein. The phrase "C$_{2-6}$ alkenyl" has the same meaning as alkenyl, except that it is limited to alkenyl groups of two to six carbons. Examples include, but are not limited to, vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, butadienyl, pentadienyl, hexadienyl, and the like.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group. The phrase "C$_{2-6}$ alkynyl" has the same meaning as alkynyl, except that it is limited to alkynyl groups of two to six carbons. Examples include, but are not limited to, —C≡C(H), —C≡C(CH$_3$), —C≡C(CH$_2$CH$_3$), —C(H$_2$)C≡C(H), —C(H)$_2$C≡C(CH$_3$), —C(H)$_2$C≡C(CH$_2$CH$_3$), —CH(CH$_3$)C≡C(H), and the like.

As used herein, "haloalkyl" refers to an alkyl group having one or more halogen substituents. Example haloalkyl groups include CF$_3$, C$_2$F$_5$, CHF$_2$, CCl$_3$, CHCl$_2$, C$_2$Cl$_5$, CH$_2$CF$_3$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. The ring-forming atoms of aryl groups are carbon atoms, and do not contain heteroatoms. The phrase "C$_{6-10}$ aryl" has the same meaning as aryl, except that it is limited to aryl groups of six to ten carbon ring-forming atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as spiroring systems. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like.

The phrase "alkoxy" refers to groups having the Formula —O-alkyl, wherein the point of attachment is the oxy group and the alkyl group is as defined above. The phrase "C$_{1-6}$ alkoxy" has the same meaning as alkoxy, except that it is limited to alkoxy groups having from one to six carbon atoms.

The phrase "aryloxy" refers to groups having the Formula —O-aryl, wherein the point of attachment is the oxy group and the aryl group is as defined above. The phrase "C$_{6-10}$ aryloxy" has the same meaning as aryloxy, except that it is limited to aryloxy groups of six to ten carbon atoms.

The phrase "C$_{1-6}$ alkoxy-C$_{1-6}$ alkyl" refers to a C$_{1-6}$ alkyl group substituted by C$_{1-6}$ alkoxy (i.e., ether groups with as many as 12 carbon atoms). One example of a C$_{1-6}$ alkoxy-C$_{1-6}$ alkyl group is —CH$_2$—O—CH$_2$CH$_3$.

The phrase "C$_{6-10}$ aryloxy-C$_{1-6}$ alkyl" refers to C$_{1-6}$ alkyl substituted by C$_{6-10}$ aryloxy, i.e., aryl ether groups of 16 carbon atoms or less, especially of 10 carbon atoms or less bound at the C$_{1-6}$ alkyl group. One example of a C$_{6-10}$ aryloxy-C$_{1-6}$ alkyl group is propoxybenzene.

The phrase "C$_{6-10}$ aryl-C$_{1-6}$ alkyl" refers to arylalkyl groups of 16 carbon atoms or less, especially of 10 carbon atoms or less bound at the C$_{1-6}$ alkyl group. One example of a C$_{6-10}$ aryl-C$_{1-6}$ alkyl group is toluene.

The phrase "trihalomethyl" refers to a methyl group in which the three H atoms of the methyl group are substituted with three halogens which may be same or different. One example of such a group is a —CF$_3$ group in which all three H atoms of the methyl group are substituted with F atoms.

For clarification, —CH$_2$C(CH$_3$)$_2$(OH) refers to 2-hydroxyl-2-methyl-propyl (i.e., 2-hydroxy-2-methyl-propyl) or 2-hydroxyl-isobutyl(i.e., 2-hydroxy-isobutyl).

The phrase "heterocyclyl" refers to both aromatic and non-aromatic ring compounds including monocyclic, bicyclic, and polycyclic ring compounds such as, but not limited to, quinuclidyl, containing 3 or more ring members of which one or more is a heteroatom such as, but not limited to, N, O, and S. Examples of heterocyclyl groups include, but are not limited to: unsaturated 3 to 8 membered rings containing 1 to 4 nitrogen atoms such as, but not limited to pyrrolyl, pyrrolinyl (e.g., pyrrolidin-1-yl, pyrrolidin-2-yl and pyrrolidin-3-yl,), imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms such as, but not limited to furanyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran. "Heterocyclyl" also refers to those groups as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others. Heterocyclyl groups are those limited to having 2 to 15 carbon atoms and as many as 6 additional heteroatoms as described above. More preferred heterocyclyl groups have from 3 to 5 carbon atoms and as many as 2 heteroatoms. Most preferred heterocyclyl groups include piperidinyl, pyrrolidinyl, azetidinyl, and aziridinyl groups.

As used herein, "heteroaryl" groups refer to an aromatic heterocycle having at least one heteroatom ring member (i.e, ring-forming atom) such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom.

Heterocycloalkyl groups can be mono or polycyclic (e.g., both fused and spiro systems). Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl (e.g., piperidin-1-yl, piperidin-2-yl, piperidin-3-yl and piperidin-4-yl), pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

Reference to "heterocyclylalkyl" refers to a heterocyclyl group as defined herein attached to an alkyl group, wherein the heterocyclylalkyl group is appended through the alkyl group. Accordingly, heterocycloalkyl and heterocyclylalkyl have different meanings and should not be used interchangeably.

As used herein, "halo" or "halogen" includes fluoro, chloro, bromo, and iodo.

As used herein, "haloalkoxy" refers to an —O-haloalkyl group. An example haloalkoxy group is $OCF_3$.

As used herein, "alkoxyalkyl" refers to an alkyl group substituted by an alkoxy group. One example of alkoxyalkyl is —$CH_2$—$OCH_3$.

As used herein, "arylalkyl" refers to alkyl substituted by aryl and "cycloalkylalkyl" refers to alkyl substituted by cycloalkyl. An example arylalkyl group is benzyl. An example cycloalkylalkyl group is 2-cyclohexyl-ethyl. As used herein, "arylalkenyl" refers to alkenyl substituted by aryl and "arylalkynyl" refers to alkynyl substituted by aryl.

As used herein, "heterocyclylalkyl" refers to an alkyl group substituted by a heterocyclyl group. One example of heterocyclylalkyl is (piperidin-1-yl)methyl. Another example of heterocyclylalkyl is 2-(pyridin-3-yl)-ethyl.

As used herein, "heteroarylalkyl" refers to an alkyl group substituted by a heteroaryl group, and "heterocycloalkylalkyl" refers to alkyl substituted by heterocycloalkyl.

As used herein, "heteroarylalkenyl" refers to alkenyl substituted by heteroaryl and "heteroarylalkynyl" refers to alkynyl substituted by heteroaryl. One example of heteroarylalkyl is 2-(pyridin-3-yl)-ethyl and one example of heterocycloalkylalkyl is (piperidin-1-yl)methyl.

As used herein, "amino" refers to $NH_2$.
As used herein, "oxo" refers to =O.
As used herein, "imino" refers to =NH.
As used herein, "guanidino" refers to —NHC(=NH)$NH_2$.
As used herein, "amidino" refers to —C(=NH)$NH_2$.

The term "substituted" refers to the replacement of one or more hydrogen atom with a monovalent or divalent radical. Suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, heterocyclyl, aryl, haloalkyl, alkoxy, alkoxyalkyl, alkylcarbonyl, arylcarbonyl, aralkylcarbonyl, alkylthio, aminoalkyl, alkylamino, cyanoalkyl, and the like. For example, one preferred "substituted $C_{1-6}$ alkyl" is 2-hydroxy-2-methyl-propyl. Other preferred substituted $C_{1-6}$ alkyl groups include alkoxyalkyl groups (i.e., groups of Formula -alkyl-O-alkyl).

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., $CH_3$) is optionally substituted, then upto 3 hydrogens on the carbon atom can be replaced with substituent groups.

The substitution group can itself be further substituted one or more times. For example, an alkoxy substituent of an alkyl group may be substituted with a halogen, and oxo group, an aryl group, or the like. The group substituted onto the substitution group can be carboxyl, halo, nitro, oxo, amino, cyano, hydroxyl, $C_{1-6}$ alkyl, $C_{1-6}$ alkoxy, $C_{6-10}$ aryl, aminocarbonyl, —SR, thioamido, —$SO_3H$, —$SO_2R$ or cycloalkyl, wherein R is typically hydrogen, hydroxyl or $C_{1-6}$ alkyl.

As used herein, "hydroxy" or "hydroxyl" refers to OH.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon atoms or heteroatoms.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, cyclohexyl is an example of a 6-membered cycloalkyl group, pyridinyl is an example of a 6-membered heteroaryl ring, and phenyl is an example of a 6-membered aryl group. The term "n-m membered" where n and m are integers typically describes the number of ring-forming atoms in a moiety where the number of ring-forming atoms is an interger selected from n, n+1, . . . and m (inclusive).

The term "protected" or a "protecting group" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W., John Wiley & Sons, New York, N.Y., (1st Edition, 1981) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, benzyl or dibenzyl, amides such as, formamide, acetamide, trifluoroacetamide, and benzamide; imides, such as phthalimide, and dithiosuccinimide; and others. In some embodiments, a protecting group for amines is a benzyl group. Examples of protected sulfhydryl groups include, but are not limited to, thioethers such as S-benzyl thioether, and S-4-picolyl thioether; substituted S-methyl derivatives such as hemithio, dithio and aminothio acetals; and others.

Imidazopyridine compounds or derivatives thereof of Formula (I) may exhibit the phenomenon of tautomerism, and the Formula drawings within this specification can represent only one of the possible tautomeric forms (such as keto-enol tautomers). It is to be understood that the invention encompasses any tautomeric form which possesses immunomodulatory activity and is not to be limited merely to any one tautomeric form utilized within the Formula drawings.

Imidazopyridines of Formula (I) also may exist in solvated as well as unsolvated forms such as, for example, hydrated forms. The invention encompasses both solvated and unsolvated forms which possess immunomodulatory activity.

The invention also includes isotopically-labeled imidazopyridine compounds or derivatives thereof, that are structurally identical to those disclosed above, except that one or more atom is/are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, tautomers thereof, prodrugs thereof, and pharmaceutically acceptable salts of the compounds and of the prodrugs that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

The foregoing may be better understood by reference to the following Examples that are presented for illustration and not to limit the scope of the inventive concepts. The Example compounds and their analogs are easily synthesized by one skilled in the art from procedures described herein, as well as in patents or patent applications listed herein which are all hereby incorporated by reference in their entireties and for all purposes as if fully set forth herein.

EXAMPLES

The compounds of the present invention may be generally made in accordance with the following reaction Schemes 1-8, which are described in detail below. Further, compounds of the embodiments may generally be prepared using a number of methods familiar to one of skill in the art, such as the methods of literature publications and those described herein.

The examples herein are prophetic in nature and are illustrated to provide exemplification as to how to prepare compounds of this invention.

Example 1

General Preparative Routes for the Synthesis of Selected Compounds of the Invention Schemes 1-8 illustrate general methods for the preparation of intermediates and compounds of the present invention.

These compounds are prepared from starting materials either known in the art for commercially available. The specific compounds are for illustrative purposes only.

As shown in Scheme 1, intermediates of Formula 1.1 (wherein P is H or an amine protecting group such as optionally substituted benzyl or tert-butyloxycarbonyl (Boc), and P' is an amine protecting group such as optionally substituted benzyl or tert-butyloxycarbonyl (Boc); or P and P' together with the N atom to which they are attached form a protecting group such as phthalimido), which have precedence in the literature or have preparations described herein, can be used to prepare compounds of the embodiment of Formula (I). Treatment of intermediates of Formula 1.1 with a compound having the Formula of $X=C(Cl)NR^1R^2$ (a carbamoyl chloride wherein X is O, or a thiocarbamoyl chloride wherein X is S) in the presence or absence of a suitable base (such as triethylamine) in a suitable solvent (such as dichloromethane, dichloroethane, or dioxane) at temperatures typically between, but not limited to, 0-100° C. provides intermediates of Formula 1.2. Intermediates of Formula 1.2 wherein X is O can be transformed to intermediates of Formula 1.3 by several methods including, but not limited to, heating in an appropriate solvent such as, for example, dioxane, toluene or xylene with or without the addition of stoichiometric or catalytic acid such as, for example, HCl or p-toluenesulfonic acid. Alternatively, intermediates of Formula 1.2 wherein X is sulfur can be transformed to intermediates of Formula 1.3 by treatment with reagents such as, for example, $FeCl_3$, $Hg(OAc)_2$ or equivalent reagents.

Intermediates of Formula 1.3 can then be treated in an appropriate fashion to remove protecting groups P and P' to provide compounds of the embodiment of Formula 1.4. For example when one or both of P and P' are substituted or unsubstituted benzyl groups, treatment with hydrogen in the presence of an appropriate transition metal catalyst such as, for example, palladium on carbon in a solvent such as, for example, methanol or tetrahydrofuran can provide compounds of the embodiment of Formula 1.4. In another example, treatment of intermediates of formula 1.3 (wherein one or both of P and P' are substituted or unsubstituted benzyl groups or Boc groups) with an acid such as HCl, HBr or TFA can provide compounds of Formula 1.4. In yet another example, an intermediate of Formula 1.3, wherein P and P' together with the N atom to which they are attached form a phthalimido group, can be treated with a suitable reagent such as hydrazine in a suitable solvent such as methanol, tetrahydrofuran or dimethylformamide to provide compounds of Formula 1.4.

Alternatively, treatment of intermediates of Formula 1.1 with a compound having the Formula of $X=C=NR^1$ (an isocyanate compound wherein X is O, or an isothiocyanate compound wherein X is S) in the presence or absence of a suitable base (such as triethylamine) in a suitable solvent (such as dichloromethane, dichloroethane, or dioxane) at temperatures typically between, but not limited to, 0-100° C. provides intermediates of Formula 1.5. Intermediates of Formula 1.5 can undergo similar chemical transformations to provide compounds of the embodiment of Formula 1.7.

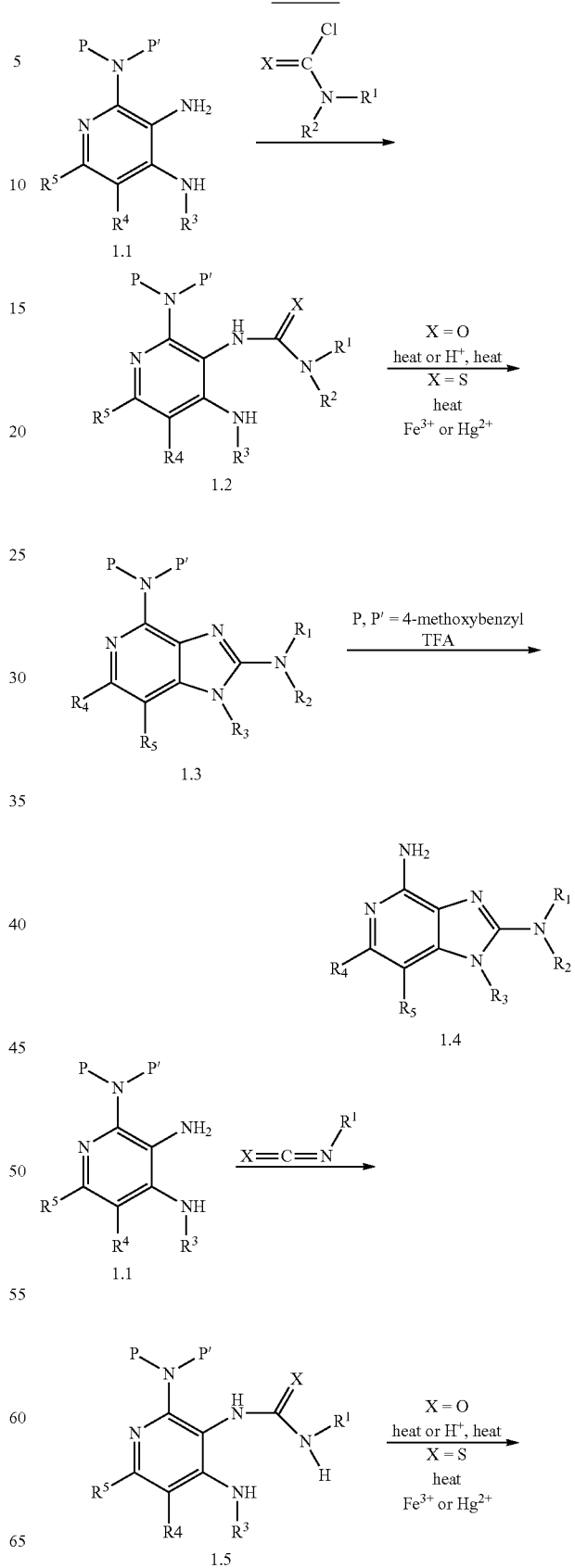

Scheme 1

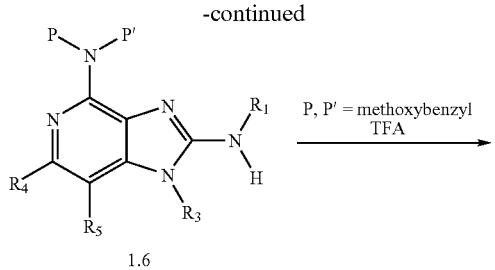

1.6

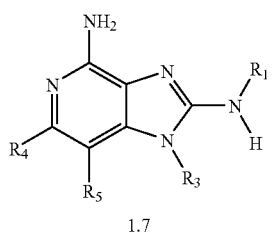

1.7

As shown in Scheme 2, intermediates of Formula 2.1 (wherein P is H or an amine protecting group such as optionally substituted benzyl or tert-butyloxycarbonyl (Boc), and P' is an amine protecting group such as optionally substituted benzyl or tert-butyloxycarbonyl (Boc); or P and P' together with the N atom to which they are attached form a protecting group such as phthalimido), which have precedence in the literature, can be used to prepare compounds of Formula (I). Treatment of intermediates of Formula 2.1 with a compound having the formula of $X=C(Cl)NR^1R^2$ (a carbamoyl chloride wherein X is O, or a thiocarbamoyl chloride wherein X is S) in the presence or absence of a suitable base (such as triethylamine) in a suitable solvent (such as dichloromethane, dichloroethane, or dioxane) at temperatures typically between, but not limited to, 0-100° C. provides intermediates of Formula 2.2. Intermediates of Formula 2.2 wherein X is O can be transformed to intermediates of Formula 2.3 by several methods including, but not limited to, heating in an appropriate solvent such as, for example, dioxane, toluene or xylene with or without the addition of stoichiometric or catalytic acid such as, for example, HCl or p-toluenesulfonic acid. Alternatively, intermediates of Formula 2.2 wherein X is sulfur can be transformed to intermediates of Formula 2.3 by treatment with reagents such as, for example, $FeCl_3$, $Hg(OAc)_2$ or equivalent reagents.

Intermediates of Formula 2.3 can then be treated in an appropriate fashion to remove protecting groups P and P' to provide compounds of the embodiment of Formula 2.4. For example when one or both of P and P' are substituted or unsubstituted benzyl groups, treatment with hydrogen in the presence of an appropriate transition metal catalyst such as, for example, palladium on carbon in a solvent such as, for example, methanol or tetrahydrofuran can provide compounds of the embodiment of Formula 2.4. In another example, treatment of intermediates of Formula 2.3 (wherein one or both of P and P' are substituted or unsubstituted benzyl groups or Boc groups) with an acid such as HCl, HBr or TFA can provide compounds of Formula 2.4. In yet another example, an intermediate of Formula 2.3, wherein P and P' together with the N atom to which they are attached form a phthalimido group, can be treated with a suitable reagent such as hydrazine in a suitable solvent such as methanol, tetrahydrofuran or dimethylformamide to provide compounds of Formula 2.4.

Alternatively, treatment of intermediates of Formula 2.1 with a compound having the Formula of $X=C=NR^1$ (an isocyanate compound wherein X is O, or an isothiocyanate compound wherein X is S) in the presence or absence of a suitable base (such as triethylamine) in a suitable solvent (such as dichloromethane, dichloroethane, or dioxane) at temperatures typically between, but not limited to, 0-100° C. provides intermediates of Formula 2.5. Intermediates of Formula 2.5 can undergo similar chemical transformations to provide compounds of the embodiment of Formula 2.7.

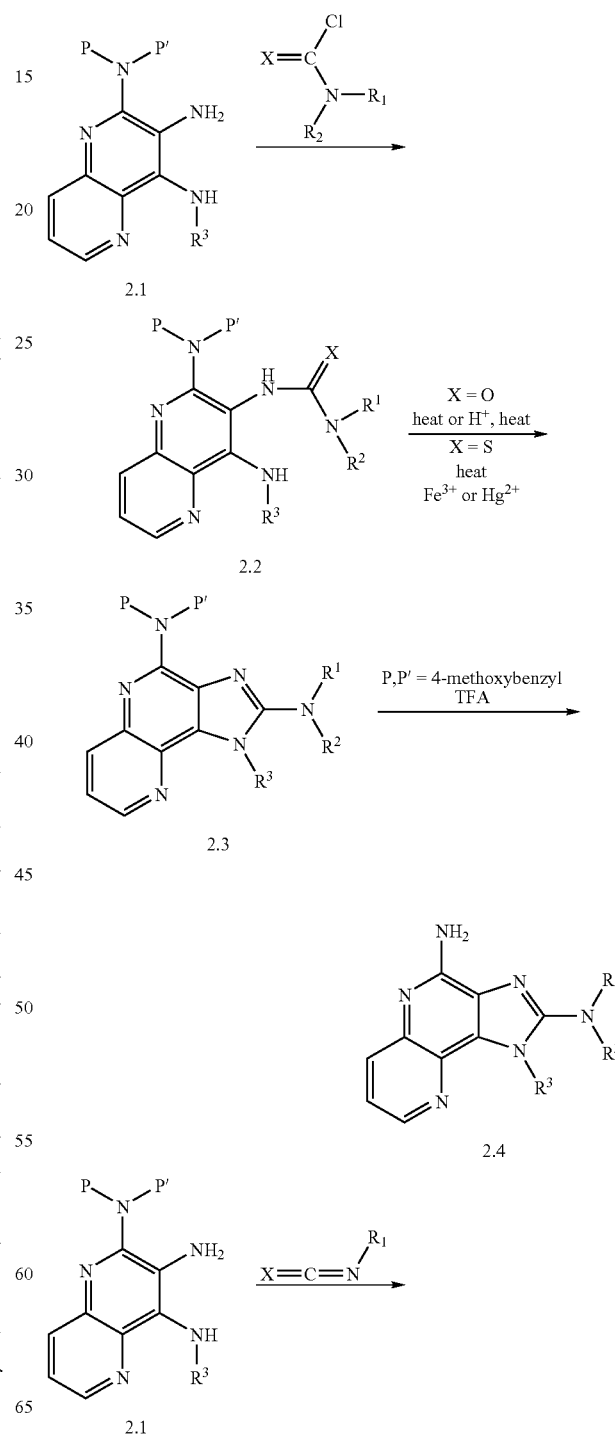

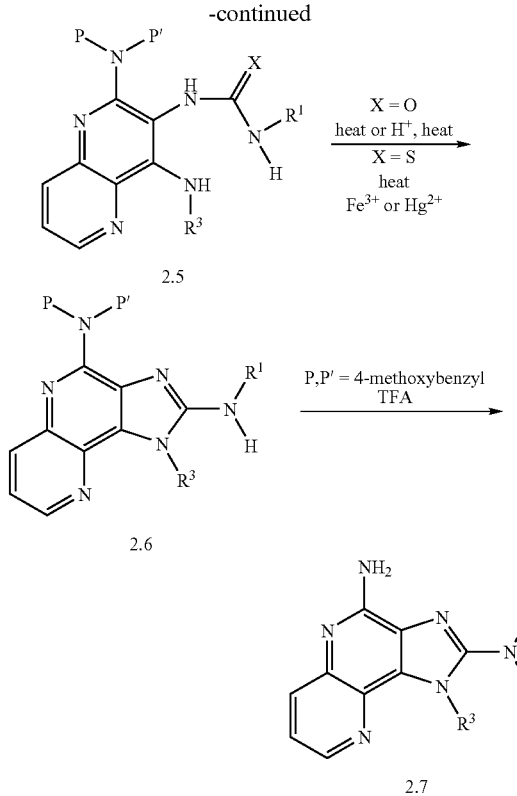

As shown in Scheme 3, a chloro-nitro-compound 3.1, which have precedence in the literature, can be used to prepare a compound of Formula (I) [as well as Formula (II)]. Treatment of the chloro-nitro compound 3.1 with a primary amine $NH_2R^3$ in a suitable solvent such as a polar aprotic organic solvent (e.g., DMF) at a temperature typically, but not limited to, 0-100° C. provides an amine-nitro-compound 3.2. Reduction of the nitro group of compound 3.2 to provide a diamine 3.3 can be accomplished by treating the compound 3.2 with a metal such as, for example, Zn or Fe in the presence of an acid such as, for example, HCl or in the presence of a reagent such as $NH_4Cl$, or equivalent, in a solvent such as, for example, methanol. Alternately, reduction of the nitro group can be accomplished by methods known to one skilled in the art of organic synthesis including, but not limited to, treatment with dithionate in a solvent such as methanol; sodium borohydride in a solvent such as methanol or tetrahydrofuran; or hydrogen with a transition metal catalyst such as palladium on carbon in a solvent such as methanol or tetrahydrofuran. The diamine compound 3.3 can be transformed in a similar fashion as described in Schemes 1 and 2 to provide compound 3.5 or 3.6. Treatment of compound 3.5 or 3.6 with a reagent such as, for example, meta-chloroperbenzoic acid followed by addition of ammonium chloride and then benzenesulfonyl chloride (similar to that described in WO 2005123080) provides compound 3.7 or 3.8 respectively.

Scheme 3

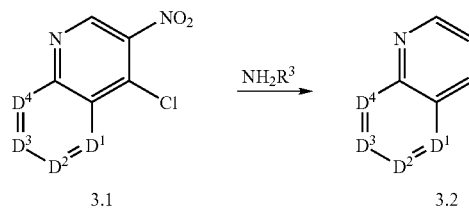

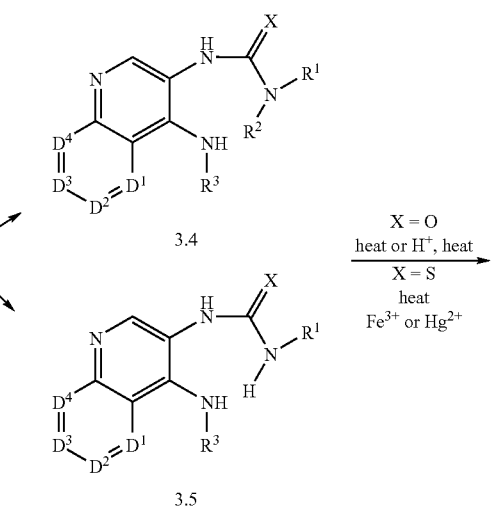

-continued

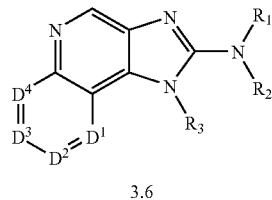
3.6

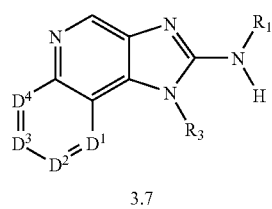
3.7

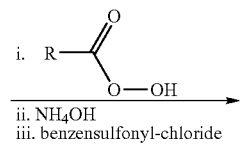
i. R—C(=O)—O—OH
ii. NH₄OH
iii. benzensulfonyl-chloride

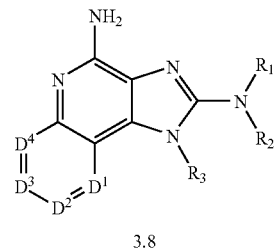
3.8

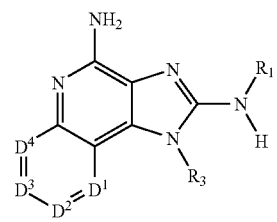
3.9

As shown in Scheme 4, intermediates of chloro-nitro compounds 4.2 can be prepared from hydroxyl-nitro-compounds 4.1 which can be prepared from starting materials either known in the art for commercially available. Also described in Scheme 4 are commercially available or literature precedent bicyclic compounds of Formula 4.3-4.6 which can be transformed to compounds of Formula 4.7-4.10 respectively following transformations similar to those described in Scheme 3.

Scheme 4

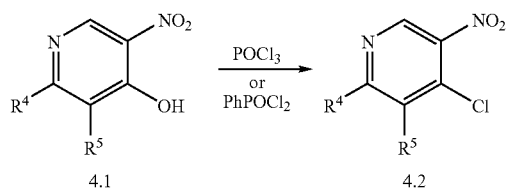

-continued

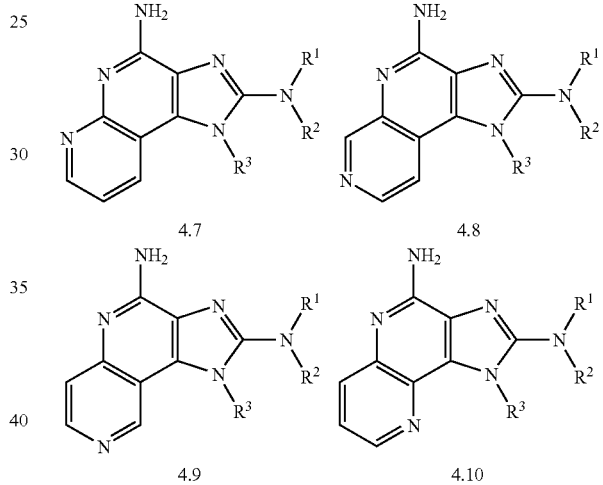

4.7    4.8

4.9    4.10

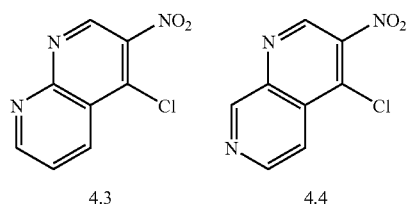
4.3    4.4

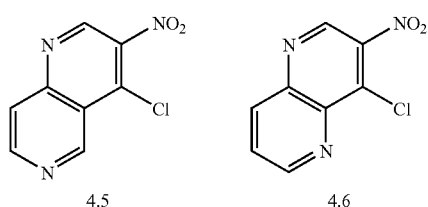
4.5    4.6

As shown in Scheme 5, a guanidino compound 5.1, which have precedence in the literature, can be used to prepare a compound of Formula (I). Treatment of a guanidino compound 5.1 with an alpha-halo ketone 5.2 (wherein R is halo such as bromo and R' is alkyl such as methyl or ethyl) such as, for example, methyl 3-bromo-2-oxopropanoate in a solvent such as, for example, ethanol in the presence or absence of a base such as, for example, triethylamine, DBU or 2,6-lutidine at temperatures typically, but not limited to, 0-100° C. provides an imidazole 5.3. Treatment of the imidazole 5.3 with a halogenating agent such as N-bromosuccinimide (NBS) can afford a halogenated imidazole 5.4. Coupling of the halogenated imidazole 5.4 with an olefinic tin compound 5.4.1 through transition metal mediate methods as described in "Palladium Reagents and Catalysts: Innovations in Organic Chemistry" by Jiro Tsuji. John Wiley & Sons Ltd., West Susses, England, 1995; "Oranopalladium Chemistry for Organic Synthesis" by E. Negishi. John Wiley & Sons Ltd., New York, N.Y., 2002; and references therein, provides an olefinic compound 5.5. Hydroboration of the olefinic compound 5.5 with reagents BR"₂H (wherein R" can be H, alkoxy, and the like; or two R" together with the boron atom form a heterocyclic ring) such as $BH_3$ or catacholborane followed by oxidation with an oxidizing reagent such as, for example, hydrogen peroxide in the presence or absence of a base such as, for example, sodium hydroxide provides intermediates of Formula 5.6. Oxidation of intermediates of Formula 5.6 with a reagent such as SO$_3$-pyridine in a suitable organic solvent such as DMSO provides an aldehyde or ketone 5.7. Treatment of the compound 5.7 with an ammonia-producing reagent such as ammonia (either gaseous or in aqueous solution), ammonium acetate, or ammonium hydroxide in a solution containing, for example, one or more of the solvents such as methanol, water and tetrahydrofuran at temperatures typically, but not limited to, 0-100° C. provides a bicyclic compound 5.8. Treatment of the compound 5.8 with a halogenating reagent such as POCl$_3$, provides a halogenated intermediate 5.9. Treatment of the halogenated intermediate 5.9 with ammonia-producing reagent such as ammonia (either gaseous or in aqueous solution), ammonium acetate, or ammonium hydroxide at temperatures typically, but not limited to, 0-200° C. provides a compound of Formula 5.10. Alternately, the halogenated intermediate 5.9 can be treated with ammonia equivalents such as, for example, azides, hydrazide or hydroxylamine followed by appropriate transformation (such as reduction of azide to amino), which is readily apparent to one skilled in the art of organic synthesis, to provide a compounds of Formula 5.10.

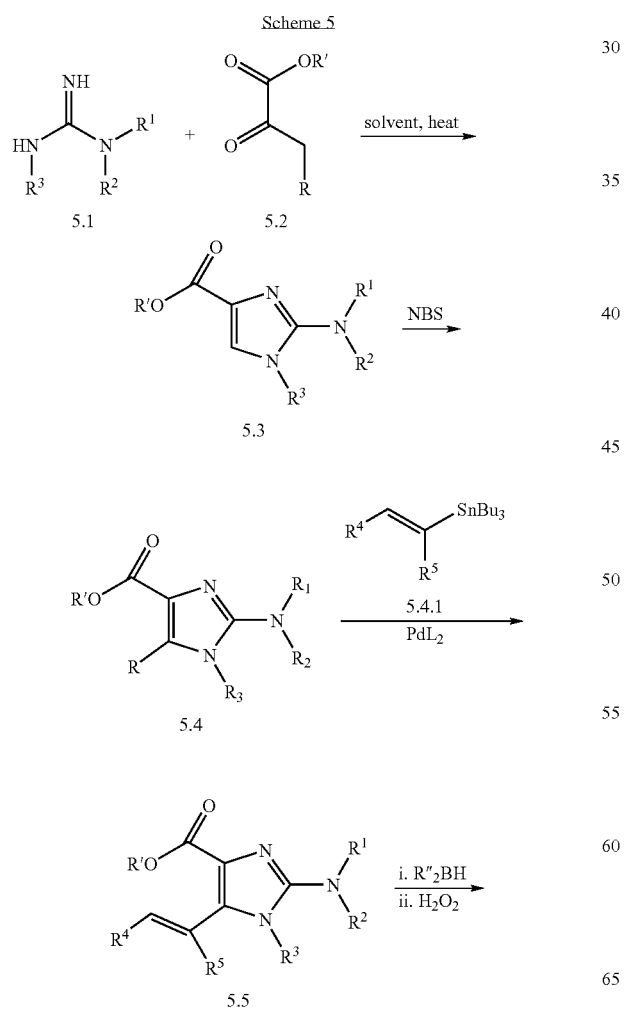

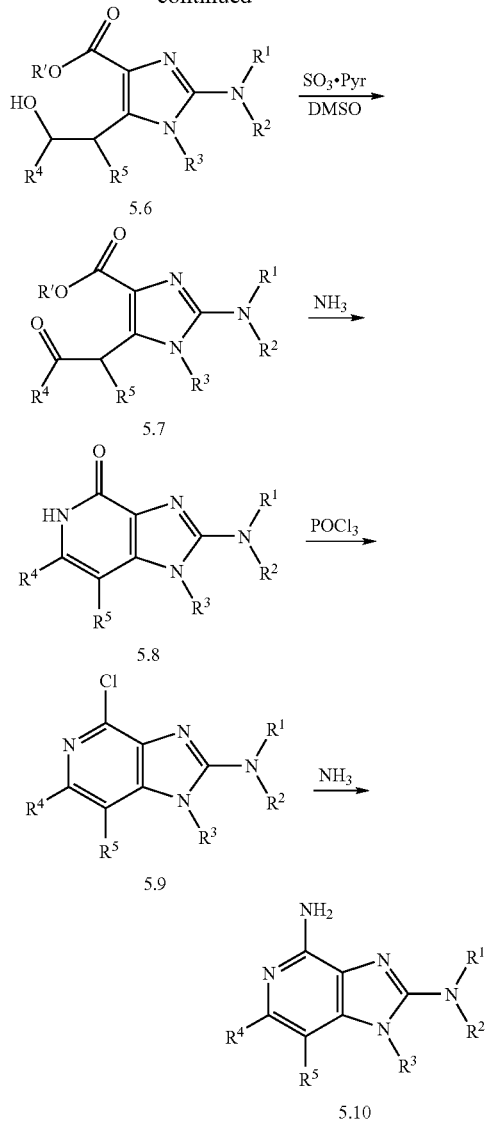

As shown in Scheme 6, an ester 6.1 (wherein R is halo such as bromo and R' is alkyl such as methyl or ethyl), which have precedence in the literature or can be prepared through methods described herein, can be used to prepare a compound of Formula (I). Treatment of the ester 6.1 with a base such as, for example, sodium hydroxide in a solvent mixture including, for example, one or more of methanol, water or tetrahydrofuran provides a carboxylic acid 6.2. Treatment of acid 6.2 with a reagent such as, for example, thionyl chloride followed by treatment with an ammonia-producing reagent (or equivalent) such as ammonia provides an amide 6.3. Coupling of the amide 6.3 (wherein R is halo such as bromo) with an acetylinic compound (alkyne) 6.3.1 through transition metal mediate methods as described in "Palladium Reagents and Catalysts: Innovations in Organic Chemistry" by Jiro Tsuji. John Wiley & Sons Ltd., West Susses, England, 1995; "Oranopalladium Chemistry for Organic Synthesis" by E. Negishi. John Wiley & Sons Ltd., New York, N.Y., 2002; and references therein, provide an acetylinic 6.4. Treatment of the acetylinic 6.4 following methods similar to those described in "Nucleosides and nucleotides. 116. Convenient syntheses of 3-deazaadenosine, 3-deazaguanosine, and 3-deazainosine via ring closure of 5-ethynyl-1-β-D-ribofuranosylimidazole-4-carboxamide or -carbonitrile." Minakawa, Moriaki; Matsuda, Akira; *Tetrahedron* 1993, 49(3), pp. 557-70 and "Nucleosides and Nucleotides. 184. Synthesis and Conformational Investigation of Anti-Fixed 3-Deaza-3-halopurine Ribonucleosides." Minakawa, Noriaki; Kojima, Naoshi; Matsuda, Akira. *Journal of Organic Chemistry* 1999, 64(19), pp. 7158-7172 provides a bicyclic compound 6.5. The bicyclic compound 6.5 can be treated with a halogenating reagent such as NBS to provide a halogenated compound 6.6. The 6.6 halogenated compound can be treated with a borate compound of $R^5B(OR'')_2$ or a tin compound $R^5Sn(R'')_3$ (wherein R'' can be alkyl or the like; or two OR'' together with the boron atom form a heterocyclic ring) under transition metal mediated methodology to provide an intermediate 6.7. The compounds 6.5-6.7 can be transformed using methods similarly to those described for compound 5.8 in Scheme 5 to provide imidazopyridine compounds such as a compound of Formula 6.8.

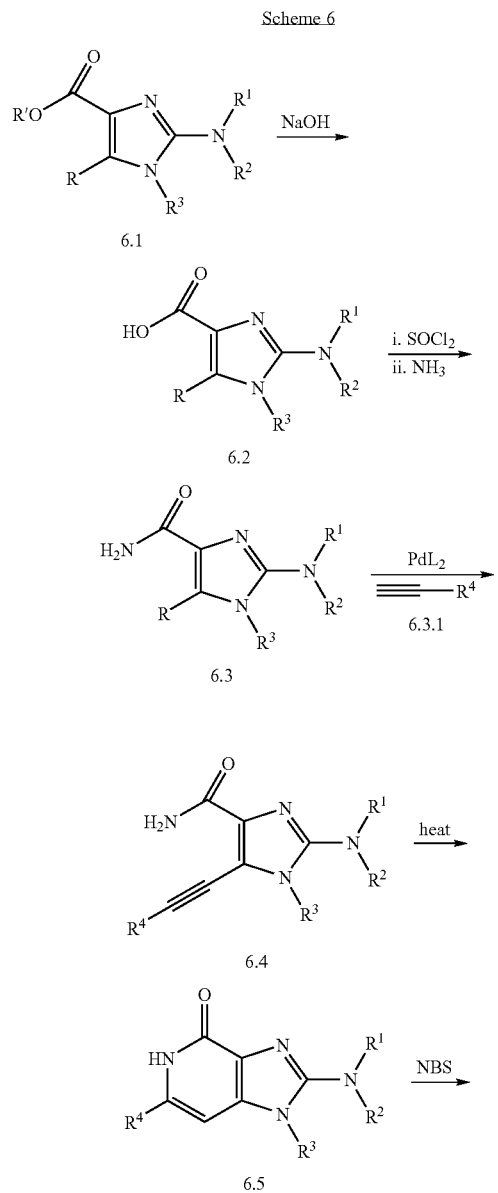

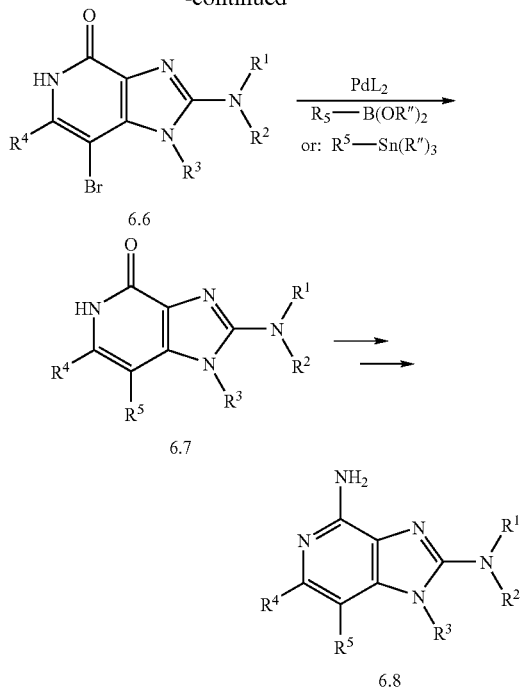

As shown in Scheme 7, an ester 7.1 (wherein R is halo such as bromo and R' is alkyl such as methyl or ethyl), which have precedence in the literature or can be prepared through methods described herein, can be used to prepare a compound of Formula (I). Treatment of the ester 7.1 in a fashion similar to that described for intermediates 5.4 in Scheme 5 or 6.1 in Scheme 6 can provide an amine 7.1.1. The amine 7.1.1 can be protected by appropriate amine protecting groups apparent to those skilled in the art to afford protected amine 7.2 (wherein P is H or an amine protecting group such as optionally substituted benzyl or tert-butyloxycarbonyl (Boc), and P' is an amine protecting group such as optionally substituted benzyl or tert-butyloxycarbonyl (Boc); or P and P' together with the N atom to which they are attached form a protecting group such as phthalimido). Treatment of the protected amine 7.2 with a base such as butyllithium in a solvent such as tetrahydrofuran at temperatures typically, but not limited to, −100-50° C. followed by addition of a reagent such as, for example, diphenyl disulfide and subsequent oxidation with an oxidizing reagent such as mCPBA provides an intermediate 7.3. Treatment of the intermediate 7.3 with a suitably substituted amine $HNR^1R^2$ in a solvent such as methanol, tetrahydrofuran, dimethylformamide or toluene at temperatures typically, but not limited to, 0-250° C. provides a protected diamine 7.4 which can be deprotected according to the nature of the protecting groups P and P' such as described in the schemes herein. Alternatively, a compound of Formula 7.6, which have precedence in the literature or can be prepared through methods described herein, can be reacted with a reagent such as trialkyl orthoformate or its equivalent (e.g., triethyl orthoformate) in a solvent such as toluene at temperatures typically, but not limited to, 0-150° C. to provide an imidazopyridine 7.2. Furthermore, a diamine 7.7 can be treated in a similar fashion to obtain an imidazopyridine 7.8. which can be transformed to an imidazopyridine 7.9 following transformations similar to those described for compound 7.2 to compound 7.5. The imidazopyridine 7.9 can be transformed to a 4-aminoimidazopyridine 7.10 following transformations similar to those described for compound 3.6 to compound 3.8 in Scheme 3.

Scheme 7

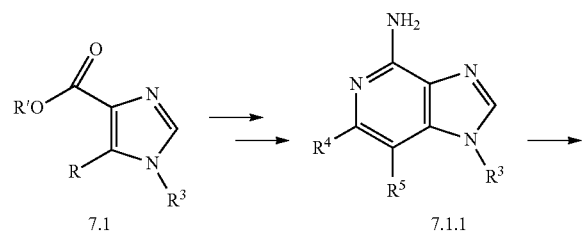

7.1 → 7.1.1

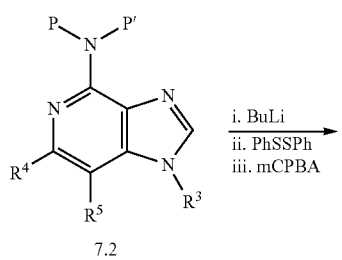

7.2 i. BuLi
ii. PhSSPh
iii. mCPBA

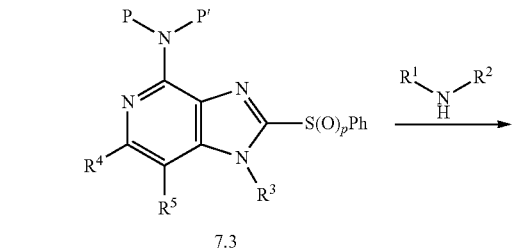

7.3

$R^1R^2NH$ →

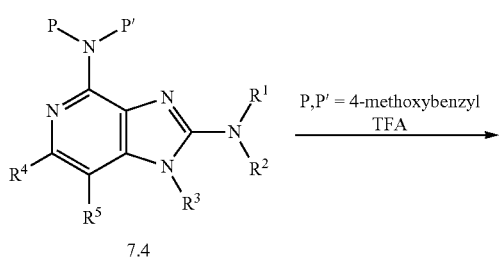

7.4

P,P' = 4-methoxybenzyl
TFA
→

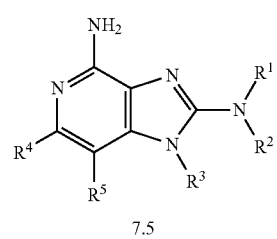

7.5

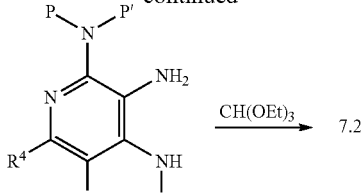

7.6

$CH(OEt)_3$ → 7.2

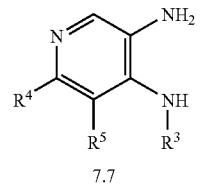

7.7

$CH(OEt)_3$ →

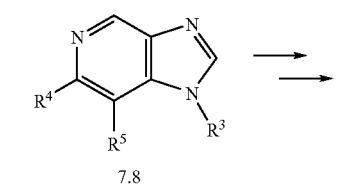

7.8 →

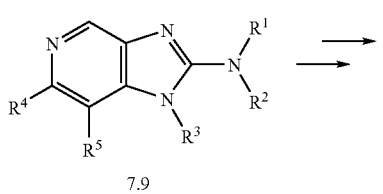

7.9 →

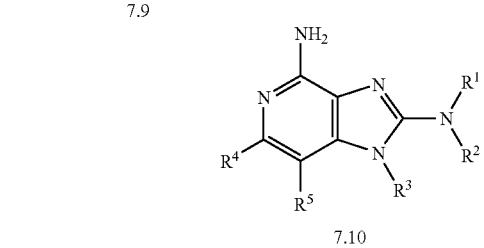

7.10

As shown in Scheme 8, Compounds 8.1-8.3 (wherein P and P' are the same as those described in Scheme 7), which are precedent in the literature or can be prepared following procedures described herein, can be transformed to imidazopyridines 8.5-8.7 respectively, by treating the compounds 8.1-8.3 with an iminium reagent such as the intermediate of Formula 8.4, which are precedent in the literature or can be prepared following procedures described herein. Imidazopyridines 8.5-8.7 can be transformed to 4-amino-imidazopyridine compounds through methods described herein with. For example, imidazopyridine 8.6 can be transformed into 4-amino-imidazopyridine 8.8 by a similar method to that describe for compound 5.9 to 5.10, such as treatment of the imidazopyridine 8.6 with ammonia; ammonium acetate; ammonium hydroxide; or sodium azide followed by reduction.

Scheme 8

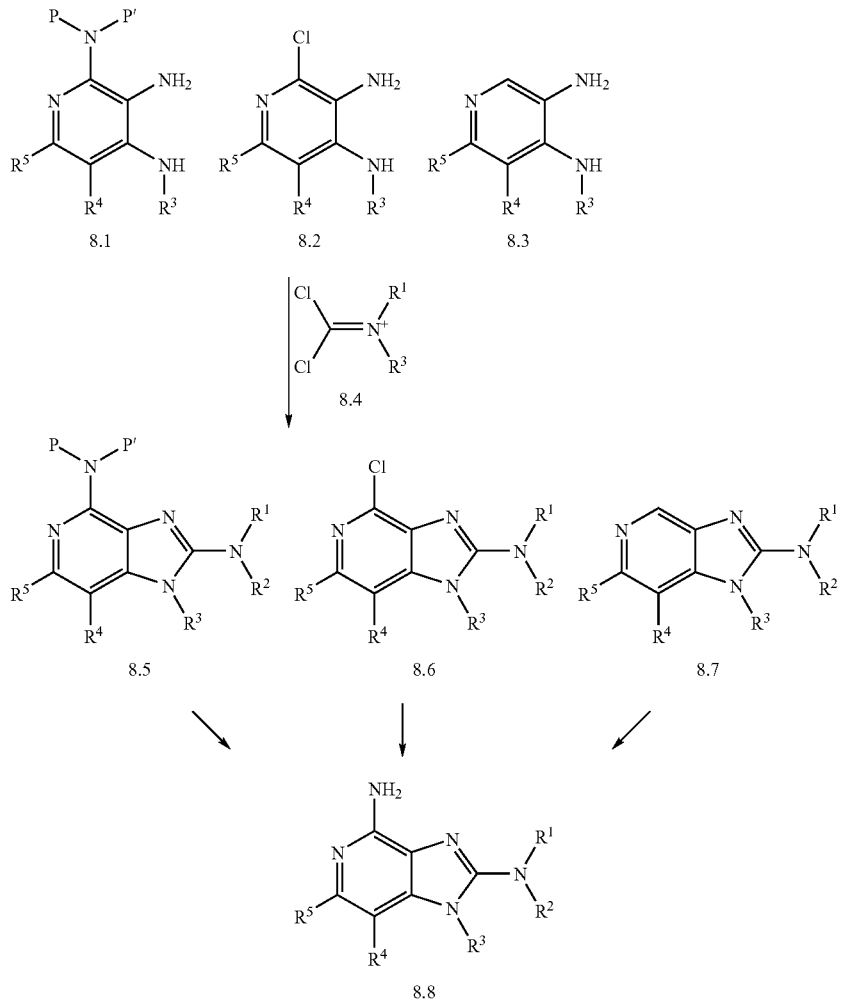

Biological Assays

The biological assays described herein provide contemplated methods for assaying the compounds of this invention for biological activity.

Candidate small molecule immunopotentiators can be identified in vitro. Compounds are screened in vitro for their ability to activate immune cells. One marker of such activation is the induction of cytokine production, for example TNF-α production. Apoptosis inducing small molecules may be identified having this activity. These small molecule immuno-potentiators have potential utility as adjuvants and immuno-therapeutics.

In an assay procedure (High Throughput Screening (HTS)) for imidazopyridine small molecule immune potentiators (SMIPs), human peripheral blood mononuclear cells (PBMC), 500,000 per mL in RPMI 1640 medium with 10% FCS, are distributed in 96 well plates (100,000 per well) already containing 5 μM of compound in DMSO. The PBMCs are incubated for 18 hours at 37° C. in 5% $CO_2$. Their ability to produce cytokines in response to the small molecule compounds is determined using a modified sandwich ELISA.

Briefly, supernatants from the PBMC cultures are assayed for secreted TNF using a primary plate bound antibody for capture followed by a secondary biotinylated anti-TNF antibody forming a sandwich. The biotinylated second antibody is then detected using streptavidin-europium, and the amount of bound europium is determined by time resolved fluorescence. Imidazopyridine compounds are confirmed by their TNF inducing activity that is measured in the assay as increased europium counts over cells incubated in RPMI medium alone. "Hits" are selected based on their TNF-inducing activity relative to an optimal dose of lipopolysaccharide LPS (1 μg/mL), a strong TNF inducer. The robustness of the assay and low backgrounds allows for the routine selection of hits with 10% of LPS activity that is normally between 5-10× background (cells alone). Selected hits are then subject to confirmation for their ability to induce cytokines from multiple donors at decreasing concentrations. Those compounds with consistent activity at or below 5 JM are considered confirmed for the purposes of this assay. The assay is readily modified for screening for compounds effective at higher or lower concentrations.

In addition to the procedure described above, methods of measuring other cytokines (e.g., IL1-beta, IL-12, IL-6, IFN-gamma, IL-10 etc.) are well known in the art and can be used to find active Imidazopyridine compounds of the present invention.

Qualitative and quantitative measurement of the immune response of a SMIP or composition comprising a SMIP of the preferred embodiments of the present invention can be implemented using methods known in the art, such as by measuring antigen specific antibody production, activation of specific populations of lymphocytes such as CD4+, CD8+ T cells or NK cells, and/or production of cytokines such as IFN, IL-2, IL-4 or IL-12. Methods for measuring specific antibody responses include enzyme-linked immunosorbent assay (ELISA) as known in the art. Measurement of numbers of specific types of lymphocytes such as CD4+ T cells can be achieved, for example, with fluorescence-activated cell sorting (FACS). Cytotoxicity assays can also be performed using methods known in the art, e.g., as described in Raz et al., (1994) Proc. Natl. Acad. Sci. USA 91:9519-9523. Serum concentrations of cytokines can be measured, for example, by ELISA. Such assays are described, e.g., in Selected Methods in Cellular Immunology (1980) Mishell and Shiigi, eds., W.H. Freeman and Co.

Additional Contemplated Biological Methods

I. Sample Preparations

Human PBMC Preparation

Human blood from one or multiple human donors are collected into the BD Vacutainer™ CPT tube with sodium citrate (BD, Franklin Lakes, N.J.), and spun for 20 minutes at 1600 g. After centrifugation, mononuclear cells in the top layer in the tubes are collected and then washed three times with PBS buffer. The washed cells are then reconstituted at a required cell concentration in complete RPMI containing 10% FBS plus 100 units/ml penicillin and 100 ug/ml streptomycin.

Mouse Spleen Cell Preparation

Spleens are isolated from Balbc mice and minced to release the splenocytes from the tissues. After the minced samples are treated ammonium salt to destroy the red blood cells, the rest of the spleenocytes are washed and reconstituted at a required cell concentration with completed RPMI medium.

Human THP-1 Cell Line

The human myelomonocytic transformed cell line is responsive to TLR8 agonists and weakly to TLR7 agonists. The cell line is cultured in RPMI medium supplemented with 10% FBS.

II. Contemplated Activity Measurement

Compound Stimulation and Multi-Cytokine Measurement

Human PBMC (hPBMC) (at 1 million cells/ml) or mouse spleen cells (at 5 million cells/ml) or human monocytic THP-1 cells (at 1 million cells/ml) are mixed with tested compounds such as imidazopyridines at titrated compound concentrations in the complete RPMI medium. After the cell cultures are incubated for 24 hours at 37° C., 5% $CO_2$, the culture supernatant is collected and assayed for the secreted cytokines in the presence of the compounds. Human or mouse Beadlyte multi-cytokine flex kits (Upstate, Lake Placid, N.Y.) are used to measure the amount of the following cytokines: TNF-α, IL-6, IL-1β, IL-8 and IL-12p40 according to the manufacturers instructions.

TLR Signaling

HEK293 cells (ATCC, CRL-1573) are seeded in a T75 flask at $3\times10^6$ in 20 ml of DMEM which is supplemented with 0.1 mM nonessential amino acid, 1 mM sodium pyruvate, 2 mM L-glutamine, penicillin-streptomycin, and 10% FCS. After overnight culturing, the cells are transfected with 1) pNFkB-TA-luciferase reporter (0.4 ug) (BD clontech, Palo Alto, Calif.), and with 2) with pGL4.74 (0.01 ug) that carries a TK promoter, not responsive to NF-kB stimulation, and carries a *Renilla* luciferase gene, used as an internal control (Promega, Wis.), and 3), separately with a following TLR construct (10 ug): human TLR (hTLR) 7, hTLR8, mouse TLR7 (mTLR7) puno constructs (Invivogene, Calif.), using Fugene 6 transfection reagent (Roche). The transfected cells after 24 hours transfection are collected and seeded in a 96-well and flat-bottom plate ($1\times10^4$ cell/well) plate, and stimulated with the test compounds at the following concentrations: 30, 10, 3, 1, 0.3, 0.1, 0.03 uM. After overnight compound stimulation, the cells are assayed for expression of fly and *renilla* luciferases using Dual-Luciferase Reporter Assay System (Promega, Wis.). NF-kb activation is directly proportional to relative fly luciferase units, which is measured against the internal control *renilla* luciferase units.

In Vivo Adjuvant Studies

In phosphate-buffered saline (PBS), 25 micrograms gp120dV2EnvSF162 antigen (recombinant gp120 protein derived from sequence of HIV-1 strain SF162—the V2 domain is deleted; Pharm Res. 2004 Dec. 21(12):2148-52) is mixed with 50 microliters of MF59 adjuvant, followed the by the addition of 0, 1, 5, or 25 micrograms of a small molecule immune potentiator (SMIP) and adjusted to 100 microliters with PBS. 50 microliters of the solution is subsequently injected into both the left and right tibialis anterior muscles of female BALB/c mice (Day 0), for a total volume of 100 microliters per mouse. Four weeks later (Day 28), 50 microliters of the solution is again injected into both the left and right tibialis anterior muscles of the mouse. Seven days after the second vaccination (Day 34), serum samples are collected, and a day later (day 35) spleens are removed. Serum samples are assayed by Env-specific serum IgG2a ELISA and Env-specific serum IgG1 ELISA. Spleen samples are assayed by Env-specific, cytokine-producing splenic CD4 and CD8 T cells.

Various modifications of the invention, in addition to those described herein, will be apparent to those skilled in the art from the foregoing description. Such modifications are also intended to fall within the scope of the appended claims. The contents of each of the patents, patent applications and journal articles cited above are hereby incorporated by reference herein and for all purposes as if fully set forth in their entireties. Additional embodiments, methods and compositions contemplated to be useful in the instant invention are disclosed in PCT/US2005/032721, PCT/US2005/022769, PCT/US2005/022520 and U.S. Ser. No. 10/814,480, 10/762,873, 60/582,654, 10/405,495, and 10/748,071 which are each hereby incorporated by reference in their entireties and for all purposes as if set forth fully herein.

What is claimed is:

1. A compound of Formula (I):

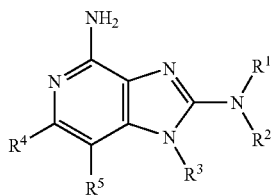

(I)

or a pharmaceutically acceptable salt thereof, a tautomer thereof, or a pharmaceutically acceptable salt of the tautomer, wherein:

$R^1$ and $R^2$ are each, independently selected from —$(CH_2)_m$CH=CH$(CH_2)_n R^6$ and $C_{1-6}$ alkyl, wherein the $C_{1-6}$ alkyl is optionally substituted by 1, 2, or 3 substituents independently selected from halo, OH, CN, $NO_2$, $C_{1-6}$ alkoxy and $C_{1-6}$ haloalkoxy;

$R^3$ is H, $C_{1-6}$ alkyl, $C_{6-10}$ aryl, heterocyclyl, $C_{3-14}$ cycloalkyl, —$(CH_2)_m$CH=CH$(CH_2)_n R^6$, —$(CH_2)_m$C≡C$(CH_2)_n R^6$, —C(=O)$NR^7 R^8$, —C(=O)$R^9$, —C(=O)$OR^9$, or —S(=O)$_q R^{10}$, wherein each of the $C_{1-6}$ alkyl, $C_{6-10}$ aryl, heterocyclyl, $C_{3-14}$ cycloalkyl is optionally substituted by 1, 2, 3, 4 or 5 substituents independently selected from halo, oxo, imino, guanidino, amidino, CN, $NO_2$, $C_{1-6}$ alkyl, $C_{1-6}$ haloalkyl, $C_{6-10}$ aryl, $C_{3-14}$ cycloalkyl, heterocyclyl, $OR^a$, $SR^a$, C(=O)$R^b$, C(=O)$NR^c R^d$, C(=O)$OR^a$, C(=S)$NR^c R^d$, OC(=O)$R^b$, OC(=O)$NR^c R^d$, $NR^c R^d$, $NR^c$C(=O)$R^b$, $NR^c$C(=O)$OR^a$, $NR^c$S(=O)$_2 R^b$, S(=O)$R^b$, S(=O)$NR^c R^d$, S(=O)$_2$OH, S(=O)$_2 R^b$, and S(=O)$_2 NR^c R^d$;

$R^4$ and $R^5$ are each, independently, selected from H, $C_{1-6}$ alkyl, $C_{1-6}$ alkoxy, halogen, trihalomethyl, —$NR^7 R^8$, —OR$^9$, —C(=O)R$^9$, —C(=O)OR$^9$, —C(=O)NR$^7$R$^8$, NR$^c$C(=O)R$^b$, NR$^c$C(=O)OR$^a$, NR$^c$S(=O)$_2$R$^b$, S(=O)R$^b$, S(=O)NR$^c$R$^d$, S(=O)$_2$OH, S(=O)$_2$R$^b$, and S(=O)$_2$NR$^c$R$^d$ wherein the C$_{1-6}$ alkyl or C$_{1-6}$ alkoxy is optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^{a'}$, SR$^{a'}$, C(=O)R$^{b'}$, C(=O)NR$^c$R$^{d'}$, C(=O)OR$^{a'}$, C(=S)NR$^c$R$^{d'}$, OC(=O)R$^{b'}$, OC(=O)NR$^c$R$^{d'}$, NR$^c$R$^{d'}$, NR$^c$C(=O)R$^{b'}$, NR$^c$C(=O)OR$^{a'}$, NR$^c$S(=O)$_2$R$^{b'}$, S(=O)R$^{b'}$, S(=O)NR$^c$R$^{d'}$, S(=O)$_2$OH, S(=O)$_2$R$^{b'}$, and S(=O)$_2$NR$^c$R$^{d'}$;

each R$^6$ is independently H, halo, C$_{1-6}$ alkyl, C$_{2-6}$ alkenyl, C$_{6-10}$ aryl, C(=O)OH, or C(=O)O—(C$_{1-6}$ alkyl), wherein each of the C$_{1-6}$ alkyl, C$_{2-6}$ alkenyl and C$_{6-10}$ aryl is optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^{a'}$, SR$^{a'}$, C(=O)R$^{b'}$, C(=O)NR$^c$R$^{d'}$, C(=O)OR$^{a'}$, C(=S)NR$^c$R$^{d'}$, OC(=O)R$^{b'}$, OC(=O)NR$^c$R$^{d'}$, NR$^c$R$^{d'}$, NR$^c$C(=O)R$^{b'}$, NR$^c$C(=O)OR$^{a'}$, NR$^c$S(=O)$_2$R$^{b'}$, S(=O)R$^{b'}$, S(=O)NR$^c$R$^{d'}$, S(=O)$_2$OH, S(=O)$_2$R$^{b'}$, and S(=O)$_2$NR$^c$R$^{d'}$;

R$^7$ and R$^8$ are each, independently, selected from H, C$_{1-6}$ alkyl, C$_{1-6}$ alkoxy-C$_{1-6}$ alkyl, C$_{6-10}$ aryl, C$_{6-10}$ aryl-C$_{1-6}$ alkyl, C$_{6-10}$ aryloxy-C$_{1-6}$ alkyl, —(CH$_2$)$_m$CH=CH(CH$_2$)$_n$R$^{11}$, and —(CH$_2$)$_m$C≡C(CH$_2$)$_n$R$^{11}$, wherein each of the C$_{1-6}$ alkyl, C$_{1-6}$ alkoxy, C$_{1-6}$ alkoxy-C$_{1-6}$ alkyl, C$_{6-10}$ aryl, C$_{6-10}$ aryl-C$_{1-6}$ alkyl and C$_{6-10}$ aryloxy-C$_{1-6}$ alkyl is optionally substituted by up to 10 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^{a'}$, SR$^{a'}$, C(=O)R$^{b'}$, C(=O)NR$^c$R$^{d'}$, C(=O)OR$^{a'}$, C(=S)NR$^c$R$^{d'}$, OC(=O)R$^{b'}$, OC(=O)NR$^c$R$^{d'}$, NR$^c$R$^{d'}$, NR$^c$C(=O)R$^{b'}$, NR$^c$C(=O)OR$^{a'}$, NR$^c$S(=O)$_2$R$^{b'}$, S(=O)R$^{b'}$, S(=O)NR$^c$R$^{d'}$, S(=O)$_2$OH, S(=O)$_2$R$^{b'}$, and S(=O)$_2$NR$^c$R$^{d'}$;

or R$^7$ and R$^8$ together with the N atom to which they are attached form a heterocyclyl group optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^{a'}$, SR$^{a'}$, C(=O)R$^{b'}$, C(=O)NR$^c$R$^{d'}$, C(=O)OR$^{a'}$, C(=S)NR$^c$R$^{d'}$, OC(=O)R$^{b'}$, OC(=O)NR$^c$R$^{d'}$, NR$^c$R$^{d'}$, NR$^c$C(=O)R$^{b'}$, NR$^c$C(=O) OR$^{a'}$, NR$^c$S(=O)$_2$R$^{b'}$, S(=O)R$^{b'}$, S(=O)NR$^c$R$^{d'}$, S(=O)$_2$OH, S(=O)$_2$R$^{b'}$, and S(=O)$_2$NR$^c$R$^{d'}$;

each R$^9$ is independently H, C$_{6-10}$ aryl, C$_{3-14}$ cycloalkyl, heterocyclyl, or C$_{1-6}$ alkyl optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^{a'}$, SR$^{a'}$, C(=O)R$^{b'}$, C(=O)NR$^c$R$^{d'}$, C(=O)OR$^{a'}$, C(=S)NR$^c$R$^{d'}$, OC(=O)R$^{b'}$, OC(=O)NR$^c$R$^{d'}$, NR$^c$R$^{d'}$, NR$^c$C(=O)R$^{d'}$, NR$^c$C(=O)OR$^{a'}$, NR$^c$S(=O)$_2$R$^{b'}$, S(=O)R$^{b'}$, S(=O)NR$^c$R$^{d'}$, S(=O)$_2$OH, S(=O)$_2$R$^{b'}$, and S(=O)$_2$NR$^c$R$^{d'}$;

each R$^{10}$ is independently C$_{1-6}$ alkyl, C$_{2-6}$ alkenyl, C$_{6-10}$ aryl, C$_{3-14}$ cycloalkyl, heterocyclyl, C$_{6-10}$ aryl-C$_{1-6}$ alkyl, trihalomethyl, or —NR$^7$R$^8$, wherein each of the C$_{1-6}$ alkyl, C$_{2-6}$ alkenyl, C$_{6-10}$ aryl, C$_{3-14}$ cycloalkyl, heterocyclyl, and C$_{6-10}$ aryl-C$_{1-6}$ alkyl is optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^{a'}$, SR$^{a'}$, C(=O)R$^{b'}$, C(=O)NR$^c$R$^{d'}$, C(=S)NR$^c$R$^{d'}$, OC(=O)R$^{b'}$, OC(=O)NR$^c$R$^{d'}$, NR$^c$R$^{d'}$, NR$^c$C(=O)R$^{b'}$, NR$^c$C(=O)OR$^{a'}$, NR$^c$S(=O)$_2$R$^{b'}$, S(=O)R$^{b'}$, S(=O)NR$^c$R$^{d'}$, S(=O)$_2$OH, S(=O)$_2$R$^{b'}$, and S(=O)$_2$NR$^c$R$^{d'}$;

each R$^{11}$ is independently H, halo, C$_{1-6}$ alkyl, C$_{2-6}$ alkenyl, C$_{6-10}$ aryl, C(=O)OH, or C(=O)O—(C$_{1-6}$ alkyl), wherein each of the C$_{1-6}$ alkyl, C$_{2-6}$ alkenyl and C$_{6-10}$ aryl is optionally substituted by 1, 2, 3, 4 or 5 substituents independently selected from halo, oxo, imino, guanidino, amidino, CN, NO$_2$, C$_{1-6}$ alkyl, C$_{1-6}$ haloalkyl, C$_{6-10}$ aryl, C$_{3-14}$ cycloalkyl, heterocyclyl, OR$^{a''}$, SR$^{a''}$, C(=O)R$^{b''}$, C(=O)NR$^{c''}$R$^{d''}$, C(=O)OR$^{a''}$, C(=S)NR$^{c''}$R$^{d''}$, OC(=O)R$^{b''}$, OC(=O)NR$^{c''}$R$^{d''}$, NR$^{c''}$R$^{d''}$, NR$^{c''}$C(=O)R$^{b''}$, NR$^{c''}$C(=O)OR$^{a''}$, NR$^{c''}$S(=O)$_2$R$^{b''}$, S(=O)R$^{b''}$, S(=O)NR$^{c''}$R$^{d''}$, S(=O)$_2$OH, S(=O)$_2$R$^{b''}$, and S(=O)$_2$NR$^{c''}$R$^{d''}$;

R$^a$, R$^{a'}$ and R$^{a''}$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocycloalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

R$^b$, R$^{b'}$ and R$^{b''}$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

R$^c$ and R$^d$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

or R$^c$ and R$^d$ together with the N atom to which they are attached form a 4-, 5-, 6- or 7-membered heterocycloalkyl group;

R$^{c'}$ and R$^{d'}$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

or R$^{c'}$ and R$^{d'}$ together with the N atom to which they are attached form a 4-, 5-, 6- or 7-membered heterocycloalkyl group;

R$^{c''}$ and R$^{d''}$ are each, independently, selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl, wherein each of the C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, heterocyclyl, C$_{6-10}$ aryl-C$_{1-6}$ alkyl, cycloalkylalkyl and heterocyclylalkyl is optionally substituted by 1, 2 or 3 substituents independently selected from OH, CN, NO$_2$, oxo, C$_{1-6}$ alkoxy, amino, halo, C$_{1-6}$ alkyl, C$_{1-6}$ haloalkyl, C$_{1-6}$ haloalkoxy, aryl, arylalkyl, heteroaryl, heteroarylalkyl, cycloalkyl and heterocycloalkyl;

or R$^{c''}$ and R$^{d''}$ together with the N atom to which they are attached form a 4-, 5-, 6- or 7-membered heterocycloalkyl group;

m and n are each, independently, selected from 0, 1, 2 and 3; and each q is independently 0, 1 or 2.

2. The compound of claim 1, wherein R$^1$ and R$^2$ are each, independently, C$_{1-4}$ alkyl, wherein the C$_{1-4}$ alkyl is optionally substituted by 1, 2, or 3 substituents independently selected from OH and C$_{1-4}$ alkoxy.

3. The compound of claim 1, wherein R$^1$ is methyl and R$^2$ is n-propyl.

4. The compound of claim 1, wherein R$^3$ is C$_{1-6}$ alkyl optionally substituted by 1, 2 or 3 substituents independently selected from halo, CN, NO$_2$, C$_{1-6}$ haloalkyl, C$_{6-10}$ aryl, C$_{3-14}$ cycloalkyl, heterocyclyl, OR$^a$, SR$^a$, C(=O)R$^b$, C(=O)NR$^c$R$^d$, C(=O)OR$^a$, C(=S)NR$^c$R$^d$, OC(=O)R$^b$, OC(=O)NR$^c$R$^d$, NR$^c$R$^d$, NR$^c$C(=O)R$^b$, NR$^c$C(=O)OR$^a$, NR$^c$S(=O)$_2$R$^b$, S(=O)R$^b$, S(=O)NR$^c$R$^d$, S(=O)$_2$OH, S(=O)$_2$R$^b$, and S(=O)$_2$NR$^c$R$^d$.

5. The compound of claim 1, wherein R$^3$ is C$_{1-6}$ alkyl optionally substituted by 1 or 2 OH.

6. The compound of claim 1 wherein:

R$^4$ and R$^5$ are each, independently, selected from H, C$_{1-6}$ alkyl, C$_{6-10}$ aryl, —NR$^7$R$^8$, and —OR$^9$, wherein each of the C$_{1-6}$ alkyl and C$_{6-10}$ aryl is optionally substituted by 1, 2 or 3 substituents independently selected from halo, OH, CN, NO$_2$, C$_{1-6}$ alkyl, C$_{1-6}$ haloalkyl, C$_{6-10}$ aryl, C$_{3-14}$ cycloalkyl, heterocyclyl, C$_{6-10}$ aryloxy, C$_{1-6}$ alkoxy and C$_{1-6}$ haloalkoxy;

R$^7$ and R$^8$ are each, independently, selected from H, C$_{1-6}$ alkyl, C$_{1-6}$ alkoxy, C$_{1-6}$ alkoxy-C$_{1-6}$ alkyl, C$_{6-10}$ aryl, C$_{6-10}$ aryl-C$_{1-6}$ alkyl, C$_{6-10}$ aryloxy-C$_{1-6}$ alkyl;

or R$^7$ and R$^8$ together with the N atom to which they are attached form a heterocyclyl group optionally substituted by 1, 2, 3, 4 or 5 substituents independently selected from halo, OH, CN, NO$_2$, C$_{1-6}$ alkyl, C$_{1-6}$ haloalkyl, C$_{6-10}$ aryloxy, C$_{1-6}$ alkoxy and C$_{1-6}$ haloalkoxy; and R$^9$ is C$_{1-6}$ alkyl, C$_{1-6}$ alkoxy-C$_{1-6}$ alkyl, C$_{6-10}$ aryl, C$_{6-10}$ aryl-C$_{1-6}$ alkyl, or C$_{6-10}$ aryloxy-C$_{1-6}$ alkyl.

7. The compound of claim 1 wherein:

R$^4$ and R$^5$ are each, independently, selected from H, C$_{6-10}$ aryl, azepanyl, morpholino, piperazinyl, piperidinyl, pyrrolidinyl, azetidinyl, aziridinyl, —NHR$^8$, and —OR$^9$; and R$^8$ and R$^9$ are each, independently, selected from C$_{1-6}$ alkyl, C$_{1-6}$ alkoxy-C$_{1-6}$ alkyl, C$_{6-10}$ aryl, C$_{6-10}$ aryl-C$_{1-6}$ alkyl and C$_{6-10}$ aryloxy-C$_{1-6}$ alkyl.

8. The compound of claim 1 wherein:

R$^1$ is methyl;

R$^2$ is n-propyl;

R$^3$ is C$_{3-6}$ alkyl optionally substituted by OH;

one of R$^4$ and R$^5$ is H and the other is selected from C$_{6-10}$ aryl, azepanyl, piperidinyl, pyrrolidinyl, azetidinyl, aziridinyl, —NHR$^8$, and —OR$^9$; and R$^8$ and R$^9$ are each, independently, C$_{1-6}$ alkoxy-C$_{1-6}$ alkyl.

9. A compound of claim 1 wherein the compound is selected from the group consisting of:

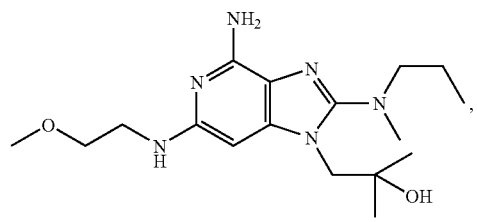

,

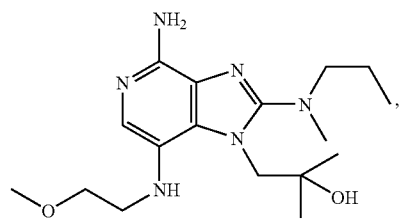

,

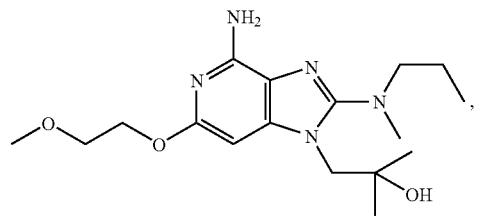

,

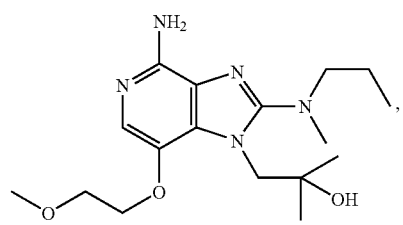

,

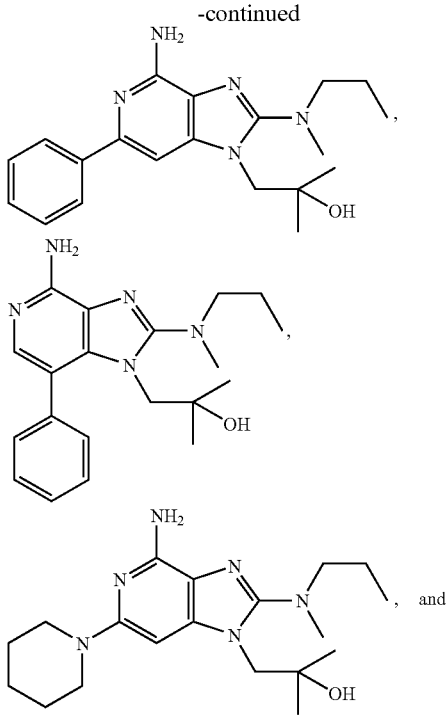
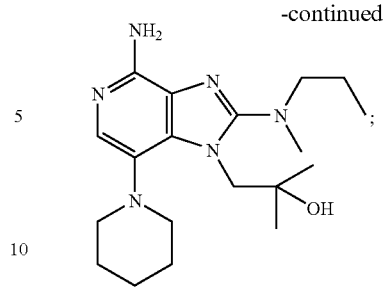
and the pharmaceutically acceptable salts thereof, tautomers thereof, and pharmaceutically acceptable salts of the tautomers.
10. A pharmaceutical composition, comprising: the compound of claim 1 and a pharmaceutically acceptable excipient.
* * * * *

SEQUENCE LISTING

<160> NUMBER OF SEQ ID NOS: 5

<210> SEQ ID NO 1
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 1
tccatgacgt tcctgacgtt                                                    20

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
tctcccagcg tgcgccat                                                      18

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
accgatgacg tcgccggtga cggcaccacg                                         30

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
tcgtcgtttt gtcgttttgt cgtt                                               24

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tccatgacgt tcctgatgct                                                    20
```